(12) United States Patent
Simon-Loriere et al.

(10) Patent No.: US 11,911,462 B2
(45) Date of Patent: *Feb. 27, 2024

(54) NUCLEIC ACID VACCINE AGAINST THE SARS-COV-2 CORONAVIRUS

(71) Applicant: INSTITUT PASTEUR, Paris (FR)

(72) Inventors: Etienne Simon-Loriere, Paris (FR); Matthieu Prot, Paris (FR); Xavier Montagutelli, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/351,065

(22) Filed: Jul. 12, 2023

(65) Prior Publication Data

US 2024/0000922 A1     Jan. 4, 2024

Related U.S. Application Data

(63) Continuation of application No. 17/819,187, filed on Aug. 11, 2022, now Pat. No. 11,759,516, which is a continuation of application No. PCT/EP2021/025053, filed on Feb. 12, 2021.

(60) Provisional application No. 62/976,148, filed on Feb. 13, 2020.

(30) Foreign Application Priority Data

Feb. 13, 2020 (EP) .................................. 20305140

(51) Int. Cl.
| | |
|---|---|
| *C12N 15/63* | (2006.01) |
| *A61K 39/215* | (2006.01) |
| *C12P 19/34* | (2006.01) |
| *A61K 39/00* | (2006.01) |

(52) U.S. Cl.
CPC ............ *A61K 39/215* (2013.01); *C12N 15/63* (2013.01); *C12P 19/34* (2013.01); *A61K 2039/51* (2013.01)

(58) Field of Classification Search
None
See application file for complete search history.

(56) References Cited

U.S. PATENT DOCUMENTS

| | | | |
|---|---|---|---|
| 11,759,516 B2 * | 9/2023 | Simon-Loriere | ...... A61K 39/12 424/221.1 |
| 2012/0082693 A1 | 4/2012 | Sylvie et al. | |
| 2021/0246170 A1 * | 8/2021 | Langedijk | ............ C07K 14/005 |

FOREIGN PATENT DOCUMENTS

| | | |
|---|---|---|
| WO | 2019/092002 A1 | 5/2019 |
| WO | 2021/156267 A1 | 8/2021 |

OTHER PUBLICATIONS

DATABASE UniParc [Online], accession No. UPI00131F240A, Jan. 2020 (Jan. 15, 2020), retrieved from UniProtabstract Database.
(Continued)

*Primary Examiner* — Benjamin P Blumel
(74) *Attorney, Agent, or Firm* — Arrigo, Lee, Guttman & Mouta-Bellum LLP

(57) ABSTRACT

The invention relates to an immunogenic or vaccine composition against the 2019 novel coronavirus (SARS-CoV-2), comprising a nucleic acid construct encoding a SARS-CoV-2 coronavirus Spike (S) protein antigen or a fragment thereof comprising the receptor-binding domain, wherein the nucleic acid construct sequence is codon-optimized for expression in human.

Figure 1:
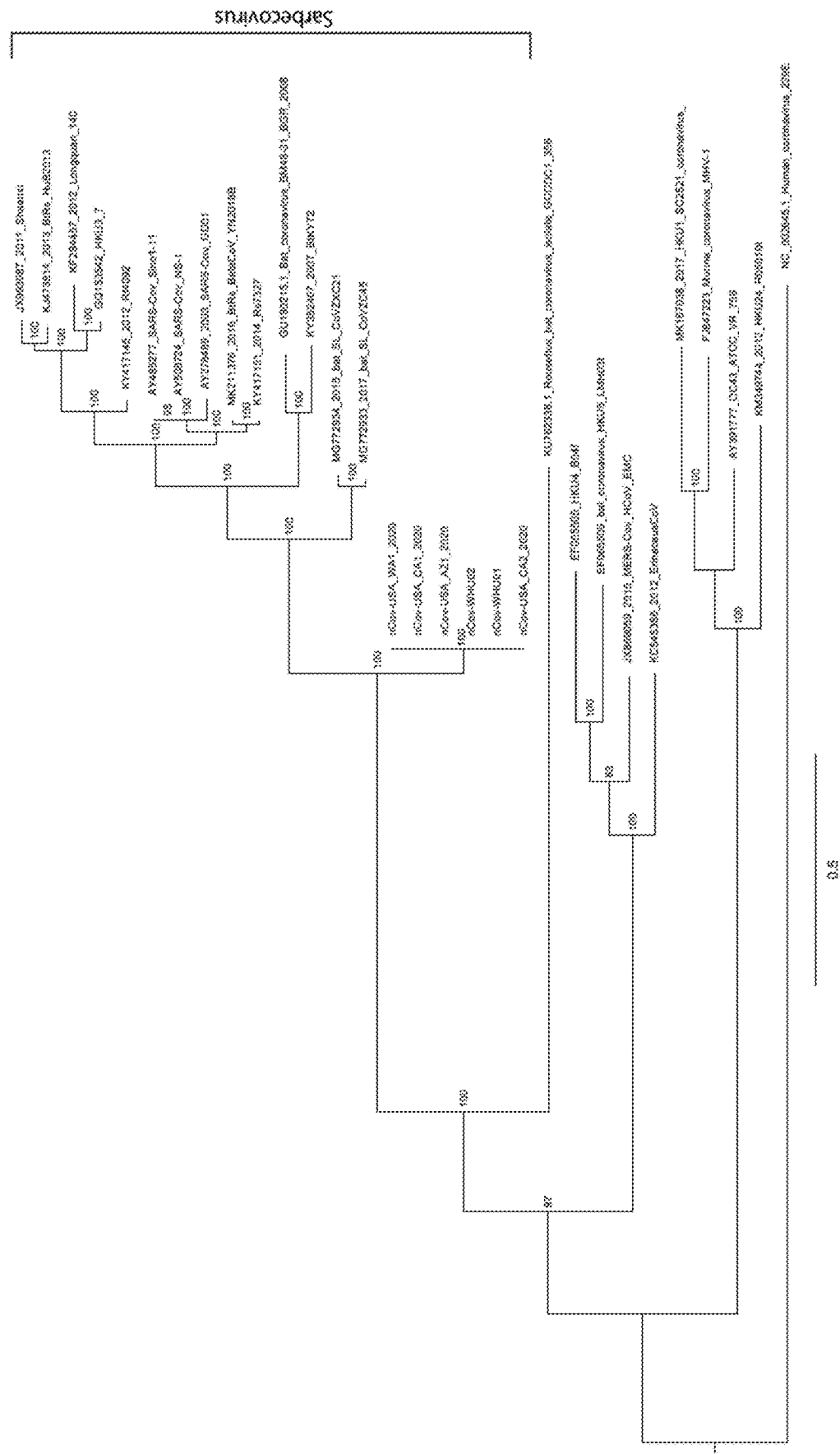

13 Claims, 9 Drawing Sheets
Specification includes a Sequence Listing.

(56) References Cited

OTHER PUBLICATIONS

DATABASE UniParc [Online], accession No. UPI0013753FF0, Jan. 2020 (Jan. 30, 2020), retrieved from UniProtabstract Database.
Du et al., Recombinant adeno-associated virus expressing the receptor-binding domain of severe acute respiratory syndrome coronavirus S protein elicits neutralizing antibodies: Implication for developing SARS vaccines, Virology, Elsevier, Amsterdam, , NL, vol. 353, No. 1, Sep. 15, 2006 (Sep. 15, 2006), pp. 6-16.
Zimmer: A Guide to Emerging SARS-CoV-2 Variants, Jan. 26, 2021 (Jan. 26, 2021), The Scientist, Retrieved from the Internet: URL:https://www.the-scientist.com/news-opinion/a-guide-to-emerging-sars-cov-2-variants-68387.
Rambaut et al: Preliminary genomic characterisation of an emergent SARS-CoV-2 lineage in the UK defined by a novel set of spike mutations , SARS-CoV-2 coronavirus / nCoV-2019 Genomic Epidemiology—Virological, pidemiology—Virological", pidemiology—Virological", Dec. 1, 2020 (Dec. 1, 2020), Retrieved from the Internet: URL:https://virological.org/t/preliminary-genomic-characterisation-of-an-emergent-sa rs-cov-2-lineage-in-the-uk-defined-by-a-novel-set-of-spike-mutations/563.
Faria et al: Genomic characterisation of an emergent SARS-CoV-2 lineage in Manaus: preliminary findings—SARS-CoV-2 coronavirus / nCoV-2019 Genomic Epidemiology—Virological, -Jan. 3, 2021 (Jan. 13, 2021), Retrieved from the Internet: URL:https://virological.org/t/genomic-characterisation-of-an-emergent-sars-cov-2lineage-in-manaus-preliminary-findings/586.
Hoffman et al: SARS-CoV-2 variants B.1.351 and B.1.1.248: Escape from therapeutic antibodies and antibodies induced by infection and vaccination, bioRxiv, Feb. 11, 2021 (Feb. 11, 2021), DOI: 10.1101/2021.02.11.430787 Retrieved from the Internet: URL:https://www.biorxiv.org/content/10.110 Jan. 2021.02.11.430787v1.full.pdf.
Ralph et al: 2019-nCOV (Wuhan virus), a novel Coronavirus: human-to-human transmission, travel-related, cases, and vaccine readiness, He Journal of Infection in Developing Countries, vol. 14, No. 01, Jan. 31, 2020 (Jan. 31, 2020), pp. 3-17.
Yu et al.: Measures for diagnosing and treating infections by a novel coronavirus responsible for a pneumonia, outbreak originating in Wuhan, China11 Microbes and Infection, Elsevier, Paris, FR, vol. 22, No. 2, Feb. 1, 2020 (Feb. 1, 2020), pp. 74-79.
Wang et al: mRNA vaccine-elicited antibodies , to SARS-CoV-2 and circulating variants, Nature, MacMillan Journals Ltd., Etc, London, vol. 592, No. 7855, Feb. 10, 2021 (Feb. 10, 2021), pp. 616-622.

* cited by examiner

Fig. 2A

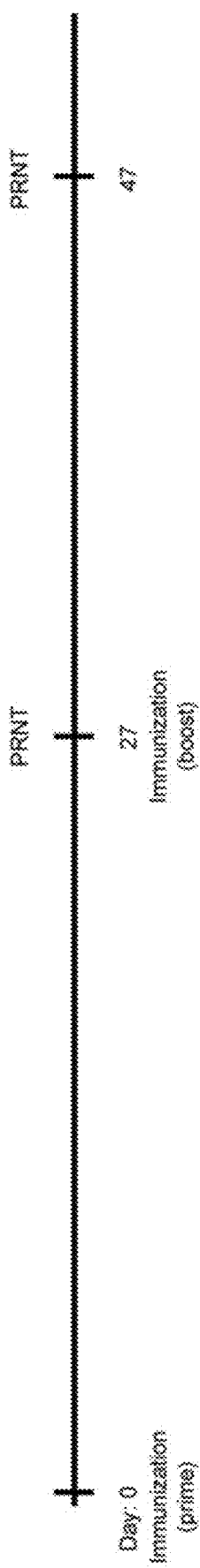
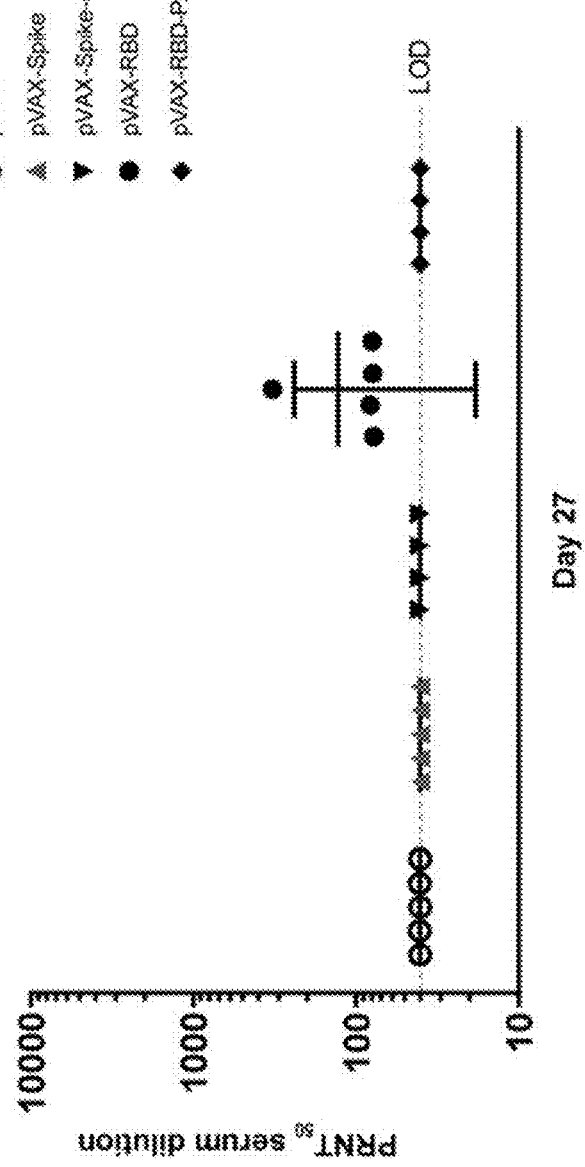
Fig. 4A
Fig. 4B

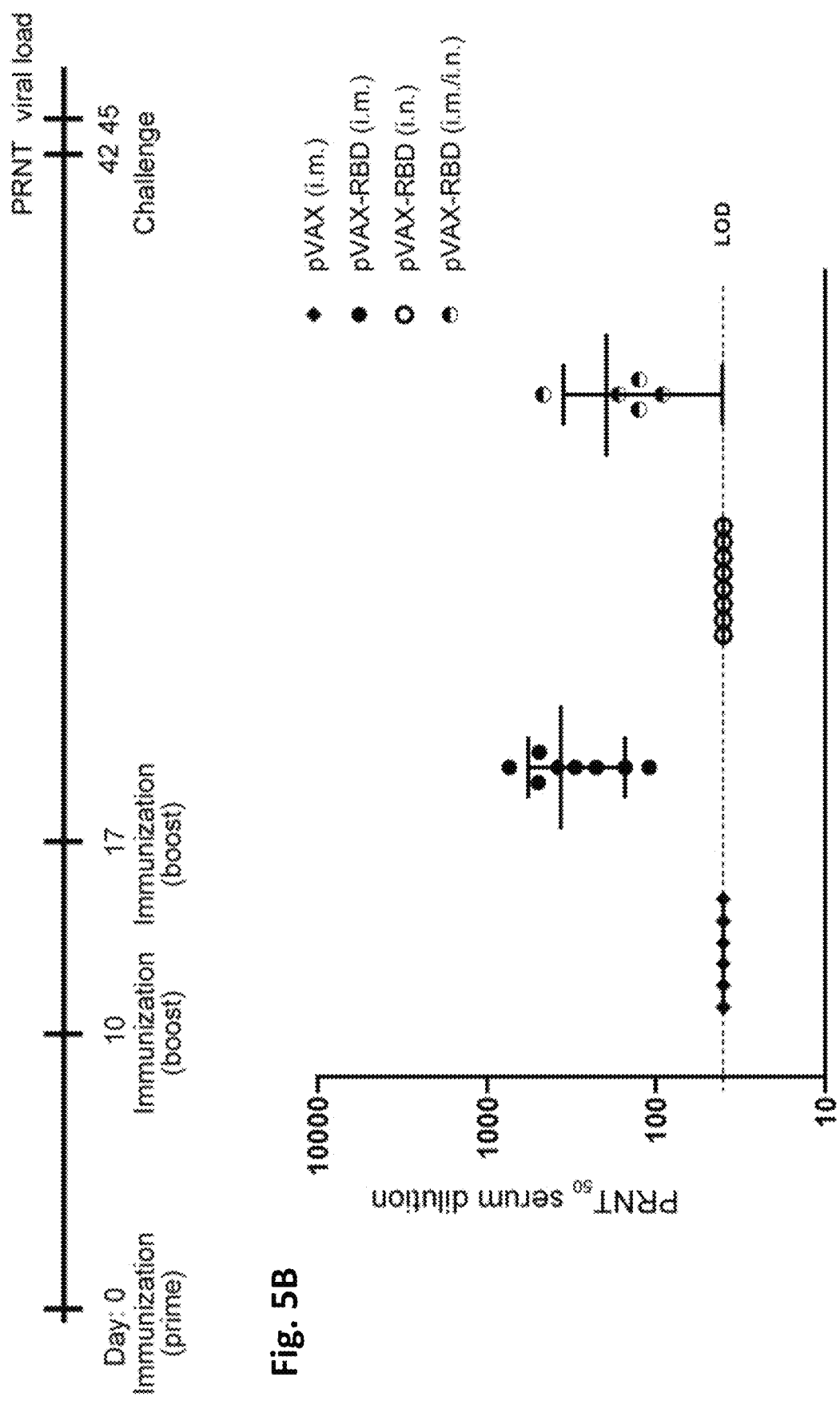

SEQUENCE LISTING

```
Sequence total quantity: 66
SEQ ID NO: 1            moltype = DNA  length = 3822
FEATURE                 Location/Qualifiers
misc_feature            1..3822
                        note = synthetic polynucleotide for
                        Antigen_1_nCov_Spike_full_opt_h.sapiens
source                  1..3822
                        mol_type = other DNA
                        organism = synthetic construct
CDS                     1..3822
SEQUENCE: 1
atgttcgtgt ttctggtgct gctgcctctg gtgtccagcc agtgtgtgaa cctgaccacc   60
agaacacagc tgcctccagc ctacaccaac agctttacca gaggcgtgta ctacccgac   120
aaggtgttca gatccagcgt gctgcactct acccaggacc tgttcctgcc tttcttcagc   180
aacgtgacct ggttccacgc catccacgtg tccggcacca atggcaccaa gagattcgac   240
aaccccgtgc tgcccttcaa cgacggggtg tactttgcca gcaccgagaa gtccaacatc   300
atcagaggct ggatcttcgg caccacactg gacagcaaga cccagagcct gctgatcgtg   360
aacaacgcca ccaacgtggt catcaaagtg tgcgagttcc agttctgcaa cgacccttc    420
ctgggcgtct actaccacaa gaacaacaag agctggatgg aaagcgagtt ccgggtgtac   480
agcagcgcca acaactgcac cttcgagtac gtgtcccagc ctttcctgat ggacctggaa   540
ggcaagcagg gcaacttcaa gaacctgcgc gagttcgtgt tcaagaacat cgacggctac   600
ttcaagatct acagcaagca caccctatc aacctcgtgc gggatctgcc tcagggcttc   660
tctgctctgg aaccccctgt ggatctgccc atcggcatca acatcaccg gtttcagaca   720
ctgctggccc tgcacagaag ctacctgaca cctggcagta gcagcaggcg atggacagct   780
ggtgccgccg cttactatgt gggctacctg cagcctagaa ccttcctgct gaagtacaac   840
gagaacggca ccatcaccga cgccgtggat tgtgctctgg atcctctgag cgagacaaag   900
tgcaccctga agtccttcac cgtggaaaag ggcatctacc agaccagcaa cttccggtg    960
cagcccaccg aatccatcgt gcggttcccc aatatcacca atctgtgccc cttcggcgag  1020
gtgttcaatg ccaccagatt cgcctctgtg tacgcctgga accggaagcg gatcagcaat  1080
tgcgtggccg actactccgt gctgtacaac tccgccagct tcagcacctt caagtgctac  1140
ggcgtgtccc ctaccaagct gaacgacctg tgcttcacaa acgtgtacgc cgacagcttc  1200
gtgatccggg gagatgaagt gcggcagatt gcccctggac agacaggcaa gatcgccgac  1260
tacaactaca agctgcccga cgacttcacc ggctgtgtga ttgcctggaa cagcaacaac  1320
ctggactcca agtcggcgg caactacaat tacctgtacc ggctgttccg gaagtccaat  1380
ctgaagccct tcgagcggga catctccacc gagatctatc aggccggcag cacccccttgt  1440
aacggcgtgg aaggcttcaa ctgctacttc ccactgcagt cctacggctt tcagcccaca  1500
aatggcgtgg gctatcagcc ctacagagtg gtggtgctga gcttcgaact gctgcatgcc  1560
cctgccacag tgtgcggccc taagaaagc accaatctct gaagaacaa atgcgtgaac  1620
ttcaacttca acggcctgac cggcaccggc gtgctgacag agagcaacaa gaagttcctg  1680
ccattccagc agtttggccg ggatatcgcc gataccacag acgccgttag agatccccag  1740
acactggaaa tcctggacat caccccttgc agcttcggcg gagtgtctgt gatcacccct  1800
ggcaccaaca ccagcaatca ggtggcagtg ctgtaccagg acgtgaactg taccgaagtg  1860
cccgtggcca ttcacgccga tcagctgaca cctacatggc gggtgtactc caccggcagc  1920
aatgtgttc agaccagagc cggctgtctg atcggagccg agcacgtgaa caatagctac  1980
gagtgcgaca tccccatcgg cgctggcatc tgtgccagct accagacaca gacaaacagc  2040
cccagacggg ccagatctgt ggccagccag agcatcattg cctacacaat gtctctgggc  2100
gccgagaaca gcgtggccta ctccaacaac tctatcgcta tccccaccaa cttcaccatc  2160
agcgtgacca cagagatcct gcctgtgtcc atgaccaaga ccagcgtgga ctgcaccatg  2220
tacatctgcg gcgattccac cgagtgctcc aacctgctgc tgcagtacgg cagcttctgc  2280
acccagctga atagagccct gacagggatc gccgtggaac aggacaagaa cacccaagag  2340
gtgttcgccc aagtgaagca gatctacaag acccctccta tcaaggactt cggcggcttc  2400
aatttcagcc agattctgcc cgatcctagc aagcccagca gcggagctt catcgaggac  2460
ctgctgttca acaaagtgac actggccgac gccggcttca tcaagcagta tggcgattgt  2520
ctgggcgaca ttgccgccag ggatctgatt tgcgcccaga gtttaacgg actgacagtg  2580
ctgcctctc tgctgaccga tgagatgatc gcccagtaca catctgccct gctggccggc  2640
acaatcacaa gcggctggac atttggagct ggcgccgctc tgcagatccc ctttgctatg  2700
cagatggcct accggttcaa cggcatcgga gtgacccaga atgtgctgta cgagaaccag  2760
aagctgatcg ccaaccagtt caacagcgcc atcggcaaga tccaggacag cctgagcagc  2820
acagcaagcg ccctgggaaa gctgcaggac gtggtcaacc agaatgccca ggcactgaac  2880
accctggtca agcagctgtc ctccaacttc ggcgccatca gctctgtgct gaacgatatc  2940
ctgagcagac tggacaaggt ggaagccgag gtgcagatcg acagactgat caccggaagg  3000
ctgcagtccc tgcagaccta cgttacccag cagctgatca gagccgccga gattagagcc  3060
tctgccaatc tggccgccac caagatgtct gagtgtgtgc tgggccagag caagagagtg  3120
gacttttgcg gcaagggcta ccacctgatg agcttccctc agtctgcccc tcacggcgtg  3180
gtgttctgc acgtgacata cgtgcccgct caagagaaga atttcaccac cgctccagcc  3240
atctgccacg acggcaaagc ccacttccct agagaaggcg tgttcgtgtc caacggcacc  3300
```

-continued

```
cattggttcg tgacccagcg gaacttctac gagccccaga tcatcaccac cgacaacacc  3360
ttcgtgtctg gcaactgcga cgtcgtgatc ggcattgtga acaataccgt gtacgaccct  3420
ctgcagcccg agctggacag cttcaaagag aactggata  agtactttaa gaaccacaca  3480
agccccgacg tggacctggg cgatatcagc ggaatcaatg ccagcgtcgt gaacatccag  3540
aaagagatcg accggctgaa cgaggtggcc aagaatctga acgagagcct gatcgacctg  3600
caagaactgg ggaagtacga gcagtacatc aagtggccct ggtacatctg gctgggcttt  3660
atcgccggac tgattgccat cgtgatggtc acaatcatgc tgtgttgcat gaccagctgc  3720
tgtagctgcc tgaagggctg ttgtagctgt ggcagctgct gcaagttcga cgaggacgat  3780
tctgagcccg tgctgaaggg cgtgaaactg cactacacct ga                     3822
```

```
SEQ ID NO: 2           moltype = AA  length = 1273
FEATURE                Location/Qualifiers
REGION                 1..1273
                       note = Synthetic Construct
source                 1..1273
                       mol_type = protein
                       organism = synthetic construct
SEQUENCE: 2
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT                                                   1273
```

```
SEQ ID NO: 3           moltype = DNA  length = 585
FEATURE                Location/Qualifiers
misc_feature           1..585
                       note = synthetic polynucleotide for RBD
source                 1..585
                       mol_type = other DNA
                       organism = synthetic construct
CDS                    1..585
SEQUENCE: 3
aatatcacca atctgtgccc cttcggcgag gtgttcaatg ccaccagatt cgcctctgtg   60
tacgcctgga accggaagcg gatcagcaat tgcgtggccg actactccgt gctgtacaac  120
tccgccagct tcagcacctt caagtgctac ggcgtgtccc ctaccaagct gaacgacctg  180
tgcttcaaca acgtgtacgc cgacagcttc gtgatccggg gagatgaagt gcggcagatt  240
gccccctgga agacaggcaa gatcgccgac tacaactaca gctgcccga cgacttcacc  300
ggctgtgtga ttgcctggaa cagcaacaac ctggactcca agtcggcgg caactacaat  360
tacctgtacc ggctgttccg gaagtccaat ctgaagccct cgagcggga catctccacc  420
gagatctatc aggccggcag caccccttgt aacggcgtgg aaggcttcaa ctgctacttc  480
ccactgcagt cctacggctt tcagcccaca aatggcgtgg gctatcagcc ctacagagtg  540
gtggtgctga gcttcgaact gctgcatgcc cctgccacag tgtga                  585
```

```
SEQ ID NO: 4           moltype = AA  length = 194
FEATURE                Location/Qualifiers
REGION                 1..194
                       note = Synthetic Construct
source                 1..194
                       mol_type = protein
                       organism = synthetic construct
SEQUENCE: 4
NITNLCPFGE VFNATRFASV YAWNRKRISN CVADYSVLYN SASFSTFKCY GVSPTKLNDL   60
CFTNVYADSF VIRGDEVRQI APGQTGKIAD YNYKLPDDFT GCVIAWNSNN LDSKVGGNYN  120
YLYRLFRKSN LKPFERDIST EIYQAGSTPC NGVEGFNCYF PLQSYGFQPT NGVGYQPYRV  180
VVLSFELLHA PATV                                                   194
```

```
SEQ ID NO: 5           moltype = AA  length = 18
FEATURE                Location/Qualifiers
REGION                 1..18
                       note = synthetic peptide (2019-nCoV signal peptide)
source                 1..18
```

-continued

```
                      mol_type = protein
                      organism = synthetic construct
SEQUENCE: 5
MFVFLVLLPL VSSQCVNL                                            18

SEQ ID NO: 6          moltype = AA  length = 26
FEATURE               Location/Qualifiers
REGION                1..26
                      note = synthetic peptide (CD5 signal peptide)
source                1..26
                      mol_type = protein
                      organism = synthetic construct
SEQUENCE: 6
MPMGSLQPLA TLYLLGMLVA SCLGRL                                   26

SEQ ID NO: 7          moltype = AA  length = 19
FEATURE               Location/Qualifiers
REGION                1..19
                      note = synthetic peptide (IL2 signal peptide)
source                1..19
                      mol_type = protein
                      organism = synthetic construct
SEQUENCE: 7
MYRMQLLSCI ALSLALVTN                                           19

SEQ ID NO: 8          moltype = AA  length = 13
FEATURE               Location/Qualifiers
REGION                1..13
                      note = synthetic peptide (PADRE epitope)
source                1..13
                      mol_type = protein
                      organism = synthetic construct
SEQUENCE: 8
AKFVAAWTLK AAA                                                 13

SEQ ID NO: 9          moltype = AA  length = 4
FEATURE               Location/Qualifiers
REGION                1..4
                      note = synthetic peptide (linker)
source                1..4
                      mol_type = protein
                      organism = synthetic construct
SEQUENCE: 9
SGSG                                                           4

SEQ ID NO: 10         moltype = DNA  length = 3828
FEATURE               Location/Qualifiers
misc_feature          1..3828
                      note = synthetic polynucleotide for
                       Antigen_1_nCov_Spike_full_opt_h.sapiens_koz
source                1..3828
                      mol_type = other DNA
                      organism = synthetic construct
CDS                   7..3828
SEQUENCE: 10
gccaccatgt tcgtgtttct ggtgctgctg cctctggtgt ccagccagtg tgtgaacctg  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgacaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaacgac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgcgcgagt tcgtgttcaa gaacatcgac  600
ggctacttca agatctacag caagcacacc cctatcaacc tcgtgcggga tctgcctcag  660
ggcttctctg ctctggaacc cctggtggat ctgcccatcg gcatcaacat cacccggttt  720
cagacactgc tggccctgca cagaagctac ctgacacctg gcgatagcag cagcggatgg  780
acagctggtg ccgccgctta ctatgtgggc tacctgcagc ctagaacctt cctgctgaag  840
tacaacgaga acggcaccat caccgacgcc gtggattgtg ctctggatcc tctgagcgag  900
acaaagtgca ccctgaagtc cttcaccgtg gaaaagggca tctaccagac cagcaacttc  960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtcccctac caagctgaac gacctgtgct tcacaaacgt gtacgccgac  1200
agcttcgtga tccggggaga tgaagtgcgg cagattgccc ctggacagac aggcaagatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga agcccttcga gcgggacatc tccaccgaga tctatcaggc cggcagcacc  1440
```

```
cccttgtaacg gcgtggaagg cttcaactgc tacttcccac tgcagtccta cggctttcag    1500
cccacaaatg gcgtgggcta tcagccctac agagtggtgg tgctgagctt cgaactgctg    1560
catgcccctg ccacagtgtg cggccctaag aaaagcacca atctcgtgaa gaacaaatgc    1620
gtgaacttca acttcaacgg cctgaccggc accggcgtgc tgacagagag caacaagaag    1680
ttcctgccat tccagcagtt tggccgggat atcgccgata ccacagacac cgttagagat    1740
ccccagacac tggaaatcct ggacatcacc ccttgcagct tcggcggagt gtctgtgatc    1800
acccctggca ccaacaccag caatcaggtg gcagtgctgt accaggacgt gaactgtacc    1860
gaagtgcccg tggccattca cgccgatcag ctgacaccta catggcgggt gtactccacc    1920
ggcagcaatg tgtttcagac cagagccggc tgtctgatcg gagccgagca cgtgaacaat    1980
agctacgagt gcgacatccc catcggcgct ggcatctgtg ccagctacca gacacagaca    2040
aacagcccca cagggccag atctgtggcc agcagagca tcattgccta cacaatgtct    2100
ctgggcgccg agaacagcgt ggcctactcc aacaactcta tcgctatccc caccaacttc    2160
accatcagcg tgaccacaga gatcctgcct gtgtccatga ccaagaccag cgtggactgc    2220
accatgtaca tctgcggcga ttccaccgag tgctccaacc tgctgctgca gtacggcagc    2280
ttctgcaccc agctgaatag agccctgaca gggatcgccg tggaacagga caagaacacc    2340
caagaggtgt tcgcccaagt gaagcagatc tacaagaccc ctcctatcaa ggacttcggc    2400
ggcttcaatt tcagccagat tctgcccgat cctagcaagc ccagcaagcg gagccttcatc    2460
gaggacctgc tgttcaacaa agtgacactg gccgacgccg gcttcatcaa gcagtatgcc    2520
gattgtctgg gcgacattgc cgccaggga ctgatttgcg cccagaagtt taacggactg    2580
acagtgctgc ctcctctgct gaccgatgag atgatcgccc agtacacatc tgccctgctg    2640
gccggcacaa tcacaagcgg ctggacattt ggagctggcg ccgctctgca gatcccctg    2700
gctatcgaa tggcctaccg gttcaacggc atcggagtga cccagaatgt gctgtacgag    2760
aaccagaagc tgatcgccaa ccagttcaac agcgccatcg gcaagatcca ggacagcctg    2820
agcagcacag caagcgccct gggaaagctg caggacgtgg tcaaccagaa tgcccaggca    2880
ctgaacaccc tggtcaagca gctgtcctcc aacttcggcg ccatcagctc tgtgctgaac    2940
gatatcctga gcagactgga caaggtggaa gccgaggtgc agatcgacag actgatcacc    3000
ggaaggctgc agtccctgca gacctacgtt acccagcagc tgatcagagc cgccgagatt    3060
agagcctctg ccaatctggc cgccaccaag atgtctgagt gtgtgctggg ccagagcaag    3120
agagtggact tttgcggcaa gggctaccac ctgatgagct ccctcagtc tgcccctcac    3180
ggcgtggtgt ttctgcacgt gacatacgtg cccgctcaag agaagaattt caccaccgct    3240
ccagccatct gccacgacgg caaagcccac tttcctagaa aaggcgtgtt cgtgtccaac    3300
ggcacccatt ggttcgtgac ccagcggaac ttctacgagc cccagatcat caccaccgac    3360
aacaccttcg tgtctggcaa ctgcgacgtc gtgatcggca ttgtgaacaa taccgtgtac    3420
gaccctctgc agcccgagct ggacagcttc aaagaggaac tggataagta cttcaagaac    3480
cacacaagcc ccgacgtgga cctgggcgat atcagcggaa tcaatgccag cgtcgtgaac    3540
atccagaaag agatcgaccg gctgaacgag gtggccaaga atctgaacga gagcctgatc    3600
gacctgcaag aactggggaa gtacgagcag tacatcaagt ggccctggta catctggctg    3660
ggctttatcg ccggactgat tgccatcgtg atggtcacaa tcatgctgtg ttgcatgacc    3720
agctgctgta gctgcctgaa gggctgttgt agctgtggca gctgctgcaa gttcgacgag    3780
gacgattctg agcccgtgct gaagggcgtg aaactgcact acacctga                 3828
```

```
SEQ ID NO: 11          moltype = AA  length = 1273
FEATURE                Location/Qualifiers
REGION                 1..1273
                       note = Synthetic Construct
source                 1..1273
                       mol_type = protein
                       organism = synthetic construct
SEQUENCE: 11
MFVFLVLLPL VSSQCVNLTT RTQLPPAYTN SFTRGVYYPD KVFRSSVLHS TQDLFLPFFS      60
NVTWFHAIHV SGTNGTKRFD NPVLPFNDGV YFASTEKSNI IRGWIFGTTL DSKTQSLLIV     120
NNATNVVIKV CEFQFCNDPF LGVYYHKNNK SWMESEFRVY SSANNCTFEY VSQPFLMDLE     180
GKQGNFKNLR EFVFKNIDGY FKIYSKHTPI NLVRDLPQGF SALEPLVDLP IGINITRFQT     240
LLALHRSYLT PGDSSSGWTA GAAAYYVGYL QPRTFLLKYN ENGTITDAVD CALDPLSETK     300
CTLKSFTVEK GIYQTSNFRV QPTESIVRFP NITNLCPFGE VFNATRFASV YAWNRKRISN     360
CVADYSVLYN SASFSTFKCY GVSPTKLNDL CFTNVYADSF VIRGDEVRQI APGQTGKIAD     420
YNYKLPDDFT GCVIAWNSNN LDSKVGGNYN YLYRLFRKSN LKPFERDIST EIYQAGSTPC     480
NGVEGFNCYF PLQSYGFQPT NGVGYQPYRV VVLSFELLHA PATVCGPKKS TNLVKNKCVN     540
FNFNGLTGTG VLTESNKKFL PFQQFGRDIA DTTDAVRDPQ TLEILDITPC SFGGVSVITP     600
GTNTSNQVAV LYQDVNCTEV PVAIHADQLT PTWRVYSTGS NVFQTRAGCL IGAEHVNNSY     660
ECDIPIGAGI CASYQTQTNS PRRARSVASQ SIIAYTMSLG AENSVAYSNN SIAIPTNFTI     720
SVTTEILPVS MTKTSVDCTM YICGDSTECS NLLLQYGSFC TQLNRALTGI AVEQDKNTQE     780
VFAQVKQIYK TPPIKDFGGF NFSQILPDPS KPSKRSFIED LLFNKVTLAD AGFIKQYGDC     840
LGDIAARDLI CAQKFNGLTV LPPLLTDEMI AQYTSALLAG TITSGWTFGA GAALQIPFAM     900
QMAYRFNGIG VTQNVLYENQ KLIANQFNSA IGKIQDSLSS TASALGKLQD VVNQNAQALN     960
TLVKQLSSNF GAISSVLNDI LSRLDKVEAE VQIDRLITGR LQSLQTYVTQ QLIRAAEIRA    1020
SANLAATKMS ECVLGQSKRV DFCGKGYHLM SFPQSAPHGV VFLHVTYVPA QEKNFTTAPA    1080
ICHDGKAHFP REGVFVSNGT HWFVTQRNFY EPQIITTDNT FVSGNCDVVI GIVNNTVYDP    1140
LQPELDSFKE ELDKYFKNHT SPDVDLGDIS GINASVVNIQ KEIDRLNEVA KNLNESLIDL    1200
QELGKYEQYI KWPWYIWLGF IAGLIAIVMV TIMLCCMTSC CSCLKGCCSC GSCCKFDEDD    1260
SEPVLKGVKL HYT                                                      1273

SEQ ID NO: 12          moltype = DNA  length = 3882
FEATURE                Location/Qualifiers
misc_feature           1..3882
                       note = synthetic polynucleotide for
                       Antigen_1_nCov_Spike_full_opt_h.sapiens_koz_with_nonnatural
                        pan DR epitope (PADRE)
source                 1..3882
```

|  |  |
|---|---|
| | mol_type = other DNA |
| | organism = synthetic construct |
| CDS | 7..3882 |

SEQUENCE: 12

```
gccaccatgt tcgtgtttct ggtgctgctg cctctggtgt ccagccagtg tgtgaacctg    60
accaccagaa cacagctgcc tccagcctac accaacagct ttaccagagg cgtgtactac   120
cccgacaagg tgttcagatc cagcgtgctg cactctaccc aggacctgtt cctgcctttc   180
ttcagcaacg tgacctggtt ccacgccatc cacgtgtccg gcaccaatgg caccaagaga   240
ttcgacaacc ccgtgctgcc cttcaacgac ggggtggtac ttgccagcac cgagaagtcc   300
aacatcatca gaggctggat cttcggcacc acactggaca gcaagaccca gagcctgctg   360
atcgtgaaca acgccaccaa cgtggtcatc aaagtgtgcg agttccagtt ctgcaacgac   420
cccttcctgg gcgtctacta ccacaagaac aacaagagct ggatggaaag cgagttccgg   480
gtgtacagca gcgccaacaa ctgcaccttc gagtacgtgt cccagccttt cctgatggac   540
ctggaaggca gcagggcaa cttcaagaac ctgcgcgagt tcgtgttcaa gaacatcgat   600
ggctacttca agatctacag caagcacacc cctatcaacc tcgtgcggga tctgcctcag   660
ggcttctctg ctctggaacc cctggtggat ctgcccatcg gcatcaacat cacccggttt   720
cagacactgc tggccctgca cagaagctac ctgacacctg gcgatagcag cagcggatgg   780
acagctggtg ccgccgctta ctatgtgggc tacctgcagc ctagaacctt cctgctgaag   840
tacaacgaga acggcaccat caccgacgcc gtggattgtg ctctggatcc tctgagcgag   900
acaaagtgca ccctgaagtc cttcaccgtg gaaaagggca tctaccagac cagcaacttc   960
cgggtgcagc ccaccgaatc catcgtgcgg ttccccaata tcaccaatct gtgcccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtccctac caagctgaac gacctgtgct tcacaaacgt gtacgccgac  1200
agcttcgtga tccggggaga tgaagtgcgg cagattgccc tggacagac aggcaagatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga agcccttcga gcgggacatc tccaccgaga tctatcaggc cggcagcacc  1440
ccttgtaacg gcgtggaagg cttcaactgc tacttcccac tgcagtccta cggctttcag  1500
cccacaaatg gcgtgggcta tcagccctac agagtggtgg tgctgagctt cgaactgctg  1560
catgcccctg ccacagtgtg cggccctaag aaaagcacca atctcgtgaa gaacaaatgc  1620
gtgaacttca acttcaacgg cctgaccggc accggcgtgc tgacagagag caacaagaag  1680
ttcctgccat tccagcagtt tggccgggat atcgccgata ccacagacgc cgttagagat  1740
ccccagacac tggaaatcct ggacatcacc ccttgccttc tcggcggagt gtctgtgatc  1800
accccctggca ccaacaccag caatcaggtg gcagtgctgt accaggacgt gaactgtacc  1860
gaagtgcccg tggccattca cgccgatcag ctgacaccta tggcgggt gtactccacc  1920
ggcagcaatg tgtttcagac cagagccggc tgtctgatcg gagccgagca cgtgaacaat  1980
agctacgagt gcgacatccc catcggcgct ggcatctgtg ccagctacca gacacagaca  2040
aacagccgca gacgggccag atctgtggcc agcagagca tcattgccta caatgtctt  2100
ctgggcgccg agaacagcgt ggcctactcc aacaactcta tcgctatccc caccaacttc  2160
accatcagcg tgaccacaga gatcctgcct gtgtccatga ccaagaccag cgtggactgc  2220
accatgtaca tctgcggcga ttccaccgag tgctccaacc tgctgctgca gtacggcagc  2280
ttctgcaccc agctgaatag agccctgaca gggatccgcc tggaacagga caagaacacc  2340
caagaggtgt tcgcccaagt gaagcagatc tacaagaccc ctcctatcaa ggacttcggc  2400
ggcttcaatt tcagccagat tctgcccgat cctagcaagc ccagcaagcg gagcttcatc  2460
gaggacctgc tgttcaacaa agtgacactg gccgacgcc gcttcatcaa gcagtatggc  2520
gattgtctgg gcgacattgc gccagggat ctgatttgcg cccagaagtt taacggactg  2580
acagtgctgc ctcctctgct gaccgatgag atgatcgccc agtacacatc tgccctgctg  2640
gccggcacaa tcacaagcgg ctggacattt ggagctggcg ccgctctgca gatccccttt  2700
gctatgcaga tggcctaccg gttcaacggc atcggagtga cccagaatgt gctgtacgag  2760
aaccagaaga tgatcgccaa ccagttcaac agcgccatcg gcaagatcca ggacagcctg  2820
agcagcacag caagcgccct ggggaaagct caggacgtgg tcaaccagaa tgcccaggca  2880
ctgaacaccc tggtcaagca gctgtcctcc aacttcggcg ccatcagctc tgtgctgaac  2940
gatatcctga gcagactgga caaggtggaa gccgaggtgc agatcgacag actgatcacc  3000
ggaaggctgc agtccctgca gacctacgtt acccagcagc tgatcagagc cgccgagatt  3060
agagcctctg ccaatctggc cgccaccaag atgtctgagt gtgtgctggg ccagagcaag  3120
agagtggact tttgcggcaa gggctaccac ctgatgagct tccctcagtc tgcccctcac  3180
ggcgtggtgt tctgcacgt gacatacgtg cccgctcaag aagaatt caccaccgct  3240
ccagccatct gccacgacgg caaagcccac tttcctagag aaggcgtgtt cgtgtccaac  3300
ggcacccatt ggttcgtgac ccagcggaac ttctacgagc cccagatcat caccaccgac  3360
aacaccttcg tgtctggcaa ctgcgacgtc gtgatcggca ttgtgaacaa taccgtgtac  3420
gaccctctgc agcccgagct ggacagcttc aagaggaac tggataagta ctttaagaac  3480
cacacaagcc ccgacgtgga cctgggcgat atcagcggaa tcaatgccag cgtcgtgaac  3540
atccagaaag atcgaccg gctgaacgga gtggccaaga tctgaacga agcctgctg  3600
gacctgcaag aactgggaa gtacgagcag tacatcaagt ggcctggta catctggctg  3660
ggctttatcg ccggactgat tgccatcgtg atggtcacaa tcatgctgtg ttgcatgacc  3720
agctgctgta gctgcctgaa gggctgttgt agctgtggca gctgctgcaa gttcgacgag  3780
gacgattctg agccgtgct gaaggcgtg aaactgcact acacctctgg aagcggcgcc  3840
aagtttgtgg ctgcctggac actgaaagcc gccgcttgat ga                   3882
```

| SEQ ID NO: 13 | moltype = AA length = 1290 |
|---|---|
| FEATURE | Location/Qualifiers |
| REGION | 1..1290 |
| | note = Synthetic Construct |
| source | 1..1290 |
| | mol_type = protein |
| | organism = synthetic construct |

SEQUENCE: 13

```
MFVFLVLLPL VSSQCVNLTT RTQLPPAYTN SFTRGVYYPD KVFRSSVLHS TQDLFLPFFS    60
```

-continued

```
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYTSGSGAKF VAAWTLKAAA                                  1290

SEQ ID NO: 14          moltype = DNA  length = 651
FEATURE                Location/Qualifiers
misc_feature           1..651
                       note = synthetic polynucleotide for
                        Antigen_2a_nCovRDB_SPnCov_OPT_koz
source                 1..651
                       mol_type = other DNA
                       organism = synthetic construct
CDS                    7..651
SEQUENCE: 14
gccaccatgt tcgtgtttct ggtgctgctg cctctggtgt ccagccagtg tgtgaacctg  60
gtcgctaata tcaccaatct gtgccccttc ggcgaggtgt tcaatgccac cagattcgcc  120
tctgtgtacg cctggaaccg gaagcggatc agcaattgcg tggccgacta ctccgtgctg  180
tacaactccg ccagcttcag caccttcaag tgctacggcg tgtcccctac caagctgaac  240
gacctgtgct tcacaaacgt gtacgccgac agcttcgtga tccggggaga tgaagtgcgg  300
cagattgccc ctggacagac aggcaagatc gccgactaca actacaagct gcccgacgac  360
ttcaccggct gtgtgattgc ctggaacagc aacaacctgg actccaaagt cggcggcaac  420
tacaattacc tgtaccggct gttccggaag tccaatctga agcccttcga gcgggacatc  480
tccaccgaga tctatcaggc cggcagcacc ccttgtaacg gcgtggaagg cttcaactgc  540
tacttcccac tgcagtccta cggctttcag cccacaaatg gcgtgggcta tcagccctac  600
agagtggtgg tgctgagctt cgaactgctg catgcccctg ccacagtgtg a          651

SEQ ID NO: 15          moltype = AA  length = 214
FEATURE                Location/Qualifiers
REGION                 1..214
                       note = Synthetic Construct
source                 1..214
                       mol_type = protein
                       organism = synthetic construct
SEQUENCE: 15
MFVFLVLLPL VSSQCVNLVA NITNLCPFGE VFNATRFASV YAWNRKRISN CVADYSVLYN  60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATV                             214

SEQ ID NO: 16          moltype = DNA  length = 705
FEATURE                Location/Qualifiers
misc_feature           1..705
                       note = synthetic polynucleotide for
                        Antigen_2a_nCovRDB_SPnCov_OPT_koz_withPADRE
source                 1..705
                       mol_type = other DNA
                       organism = synthetic construct
CDS                    7..705
SEQUENCE: 16
gccaccatgt tcgtgtttct ggtgctgctg cctctggtgt ccagccagtg tgtgaacctg  60
gtcgctaata tcaccaatct gtgccccttc ggcgaggtgt tcaatgccac cagattcgcc  120
tctgtgtacg cctggaaccg gaagcggatc agcaattgcg tggccgacta ctccgtgctg  180
tacaactccg ccagcttcag caccttcaag tgctacggcg tgtcccctac caagctgaac  240
gacctgtgct tcacaaacgt gtacgccgac agcttcgtga tccggggaga tgaagtgcgg  300
cagattgccc ctggacagac aggcaagatc gccgactaca actacaagct gcccgacgac  360
ttcaccggct gtgtgattgc ctggaacagc aacaacctgg actccaaagt cggcggcaac  420
tacaattacc tgtaccggct gttccggaag tccaatctga agcccttcga gcgggacatc  480
tccaccgaga tctatcaggc cggcagcacc ccttgtaacg gcgtggaagg cttcaactgc  540
tacttcccac tgcagtccta cggctttcag cccacaaatg gcgtgggcta tcagccctac  600
agagtggtgg tgctgagctt cgaactgctg catgcccctg ccacagtgtc tggaagcggc  660
gccaagtttg tggctgcctg gacactgaaa gccgccgctt gatga                 705
```

```
SEQ ID NO: 17              moltype = AA   length = 231
FEATURE                    Location/Qualifiers
REGION                     1..231
                           note = Synthetic Construct
source                     1..231
                           mol_type = protein
                           organism = synthetic construct
SEQUENCE: 17
MFVFLVLLPL VSSQCVNLVA NITNLCPFGE VFNATRFASV YAWNRKRISN CVADYSVLYN    60
SASFSTFKCY GVSPTKLNDL CFTNVYADSF VIRGDEVRQI APGQTGKIAD YNYKLPDDFT   120
GCVIAWNSNN LDSKVGGNYN YLYRLFRKSN LKPFERDIST EIYQAGSTPC NGVEGFNCYF   180
PLQSYGFQPT NGVGYQPYRV VVLSFELLHA PATVSGSGAK FVAAWTLKAA A           231

SEQ ID NO: 18              moltype = DNA   length = 675
FEATURE                    Location/Qualifiers
misc_feature               1..675
                           note = synthetic polynucleotide for
                            Antigen_2b_nCovRDB_SP-CD5_OPT_koz
source                     1..675
                           mol_type = other DNA
                           organism = synthetic construct
CDS                        7..675
SEQUENCE: 18
gccaccatgc ccatggggtc tctgcaaccg ctggccacct tgtacctgct ggggatgctg    60
gtcgcttcct gcctcggacg gctggtcgct aatatcacca cgctctgtgc cttcggcgag   120
gtgttcaatg ccaccagatt cgcctctgtg tacgcctgga accggaagcg gatcagcaat   180
tgcgtggccg actactccgt gctgtacaac tccgccagct tcagcacctt caagtgctac   240
ggcgtgtccc ctaccaagct gaacgacctg tgcttcacaa acgtgtacgc cgacagcttc   300
gtgatccggg gagatgaagt gcggcagatt gcccctggac agacaggcaa gatcgccgac   360
tacaactaca agctgcccga cgacttcacc ggctgtgtga ttgcctggaa cagcaacaac   420
ctggactcca agtcggcgg caactacaat tacctgtacc ggctgttccg gaagtccaat   480
ctgaagccct cgagcggga catctccacc gagatctatc aggccggcag cacccccttgt   540
aacggcgtgg aaggcttcaa ctgctacttc ccactgcagt cctacggctt tcagcccaca   600
aatggcgtgg gctatcagcc ctacagagtg gtggtgctga gcttcgaact gctgcatgcc   660
cctgccacag tgtga                                                   675

SEQ ID NO: 19              moltype = AA   length = 222
FEATURE                    Location/Qualifiers
REGION                     1..222
                           note = Synthetic Construct
source                     1..222
                           mol_type = protein
                           organism = synthetic construct
SEQUENCE: 19
MPMGSLQPLA TLYLLGMLVA SCLGRLVANI TNLCPFGEVF NATRFASVYA WNRKRISNCV    60
ADYSVLYNSA SFSTFKCYGV SPTKLNDLCF TNVYADSFVI RGDEVRQIAP GQTGKIADYN   120
YKLPDDFTGC VIAWNSNNLD SKVGGNYNYL YRLFRKSNLK PFERDISTEI YQAGSTPCNG   180
VEGFNCYFPL QSYGFQPTNG VGYQPYRVVV LSFELLHAPA TV                     222

SEQ ID NO: 20              moltype = DNA   length = 729
FEATURE                    Location/Qualifiers
misc_feature               1..729
                           note = synthetic polynucleotide for
                            Antigen_2b_nCovRDB_SP-CD5_OPT_koz_withPADRE
source                     1..729
                           mol_type = other DNA
                           organism = synthetic construct
CDS                        7..729
SEQUENCE: 20
gccaccatgc ccatggggtc tctgcaaccg ctggccacct tgtacctgct ggggatgctg    60
gtcgcttcct gcctcggacg gctggtcgct aatatcacca atctgtgccc cttcggcgag   120
gtgttcaatg ccaccagatt cgcctctgtg tacgcctgga accggaagcg gatcagcaat   180
tgcgtggccg actactccgt gctgtacaac tccgccagct tcagcacctt caagtgctac   240
ggcgtgtccc ctaccaagct gaacgacctg tgcttcacaa acgtgtacgc cgacagcttc   300
gtgatccggg gagatgaagt gcggcagatt gcccctggac agacaggcaa gatcgccgac   360
tacaactaca agctgcccga cgacttcacc ggctgtgtga ttgcctggaa cagcaacaac   420
ctggactcca agtcggcgg caactacaat tacctgtacc ggctgttccg gaagtccaat   480
ctgaagccct cgagcggga catctccacc gagatctatc aggccggcag cacccccttgt   540
aacggcgtgg aaggcttcaa ctgctacttc ccactgcagt cctacggctt tcagcccaca   600
aatggcgtgg gctatcagcc ctacagagtg gtggtgctga gcttcgaact gctgcatgcc   660
cctgccacag tgtctggaag cggcgccaag tttgtggctg cctggacact gaaagccgcc   720
gcttgatga                                                          729

SEQ ID NO: 21              moltype = AA   length = 239
FEATURE                    Location/Qualifiers
REGION                     1..239
                           note = Synthetic Construct
source                     1..239
```

```
                        mol_type = protein
                        organism = synthetic construct
SEQUENCE: 21
MPMGSLQPLA TLYLLGMLVA SCLGRLVANI TNLCPFGEVF NATRFASVYA WNRKRISNCV    60
ADYSVLYNSA SFSTFKCYGV SPTKLNDLCF TNVYADSFVI RGDEVRQIAP GQTGKIADYN   120
YKLPDDFTGC VIAWNSNNLD SKVGGNYNYL YRLFRKSNLK PFERDISTEI YQAGSTPCNG   180
VEGFNCYFPL QSYGFQPTNG VGYQPYRVVV LSFELLHAPA TVSGSGAKFV AAWTLKAAA    239

SEQ ID NO: 22           moltype = DNA  length = 654
FEATURE                 Location/Qualifiers
misc_feature            1..654
                        note = synthetic polynucleotide for
                         Antigen_2c_nCovRDB_SP-IL2_OPT_koz
source                  1..654
                        mol_type = other DNA
                        organism = synthetic construct
CDS                     7..654
SEQUENCE: 22
gccaccatgt acaggatgca actcctgtct tgcattgcac taagtcttgc acttgtcaca    60
aacagtgcaa atatcaccaa tctgtgcccc ttcggcgagg tgttcaatgc caccagattc   120
gcctctgtgt acgcctggaa ccggaagcgg atcagcaatt gcgtggccga ctactccgtg   180
ctgtacaact ccgccagctt cagcaccttc aagtgctacg gcgtgtcccc taccaagctg   240
aacgacctgt gcttcacaaa cgtgtacgcc gacagcttcg tgatccgggg agatgaagtg   300
cggcagattg cccctggaca gacaggcaag atcgccgact acaactacaa gctgcccgac   360
gacttcaccg gctgtgtgat tgcctggaac agcaacaacc tggactccaa agtcggcggc   420
aactacaatt acctgtaccg gctgttccgg aagtccaatc tgaagccctt cgagcgggac   480
atctccaccg agatctatca ggccggcagc acccccttgta acggcgtgga aggcttcaac   540
tgctacttcc cactgcagtc ctacggcttt cagcccacaa atggcgtggg ctatcagccc   600
tacagagtgg tggtgctgag cttcgaactg ctgcatgccc ctgccacagt gtga          654

SEQ ID NO: 23           moltype = AA  length = 215
FEATURE                 Location/Qualifiers
REGION                  1..215
                        note = Synthetic Construct
source                  1..215
                        mol_type = protein
                        organism = synthetic construct
SEQUENCE: 23
MYRMQLLSCI ALSLALVTNS ANITNLCPFG EVFNATRFAS VYAWNRKRIS NCVADYSVLY    60
NSASFSTFKC YGVSPTKLND LCFTNVYADS FVIRGDEVRQ IAPGQTGKIA DYNYKLPDDF   120
TGCVIAWNSN NLDSKVGGNY NYLRLFRKS NLKPFERDIS TEIYQAGSTP CNGVEGFNCY    180
FPLQSYGFQP TNGVGYQPYR VVVLSFELLH APATV                              215

SEQ ID NO: 24           moltype = DNA  length = 708
FEATURE                 Location/Qualifiers
misc_feature            1..708
                        note = synthetic polynucleotide for
                         Antigen_2c_nCovRDB_SP-IL2_OPT_kozwithPADRE
source                  1..708
                        mol_type = other DNA
                        organism = synthetic construct
CDS                     7..708
SEQUENCE: 24
gccaccatgt acaggatgca actcctgtct tgcattgcac taagtcttgc acttgtcaca    60
aacagtgcaa atatcaccaa tctgtgcccc ttcggcgagg tgttcaatgc caccagattc   120
gcctctgtgt acgcctggaa ccggaagcgg atcagcaatt gcgtggccga ctactccgtg   180
ctgtacaact ccgccagctt cagcaccttc aagtgctacg gcgtgtcccc taccaagctg   240
aacgacctgt gcttcacaaa cgtgtacgcc gacagcttcg tgatccgggg agatgaagtg   300
cggcagattg cccctggaca gacaggcaag atcgccgact acaactacaa gctgcccgac   360
gacttcaccg gctgtgtgat tgcctggaac agcaacaacc tggactccaa agtcggcggc   420
aactacaatt acctgtaccg gctgttccgg aagtccaatc tgaagccctt cgagcgggac   480
atctccaccg agatctatca ggccggcagc acccccttgta acggcgtgga aggcttcaac   540
tgctacttcc cactgcagtc ctacggcttt cagcccacaa atggcgtggg ctatcagccc   600
tacagagtgg tggtgctgag cttcgaactg ctgcatgccc ctgccacagt gtctggaagc   660
ggcgccaagt ttgtggctgc ctggacactg aaagccgccc ttgatga                 708

SEQ ID NO: 25           moltype = AA  length = 232
FEATURE                 Location/Qualifiers
REGION                  1..232
                        note = Synthetic Construct
source                  1..232
                        mol_type = protein
                        organism = synthetic construct
SEQUENCE: 25
MYRMQLLSCI ALSLALVTNS ANITNLCPFG EVFNATRFAS VYAWNRKRIS NCVADYSVLY    60
NSASFSTFKC YGVSPTKLND LCFTNVYADS FVIRGDEVRQ IAPGQTGKIA DYNYKLPDDF   120
TGCVIAWNSN NLDSKVGGNY NYLRLFRKS NLKPFERDIS TEIYQAGSTP CNGVEGFNCY    180
FPLQSYGFQP TNGVGYQPYR VVVLSFELLH APATVSGSGA KFVAAWTLKA AA           232
```

-continued

```
SEQ ID NO: 26           moltype = DNA  length = 51
FEATURE                 Location/Qualifiers
misc_feature            1..51
                        note = ynthetic polynucleotide for padre_seq_OPT_nt
source                  1..51
                        mol_type = other DNA
                        organism = synthetic construct
CDS                     1..51
SEQUENCE: 26
tctggaagcg gcgccaagtt tgtggctgcc tggacactga aagccgccgc t          51

SEQ ID NO: 27           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 27
SGSGAKFVAA WTLKAAA                                                17

SEQ ID NO: 28           moltype = AA  length = 1196
FEATURE                 Location/Qualifiers
REGION                  1..1196
                        note = synthetic polypeptide (6acd.1.A)
source                  1..1196
                        mol_type = protein
                        organism = synthetic construct
SEQUENCE: 28
MFIFLLFLTL TSGSDLDRCT TFDDVQAPNY TQHTSSMRGV YYPDEIFRSD TLYLTQDLFL  60
PFYSNVTGFH TINHTFGNPV IPFKDGIYFA ATEKSNVVRG WVFGSTMNNK SQSVIIINNS  120
TNVVIRACNF ELCDNPFFAV SKPMGTQTHT MIFDNAFNCT FEYISDAFSL DVSEKSGNFK  180
HLREFVFKNK DGFLYVYKGY QPIDVVRDLP SGFNTLKPIF KLPLGINITN FRAILTAFSP  240
AQDIWGTSAA AYFVGYLKPT TFMLKYDENG TITDAVDCSQ NPLAELKCSV KSFEIDKGIY  300
QTSNFRVVPS GDVVRFPNIT NLCPFGEVFN ATKFPSVYAW ERKKISNCVA DYSVLYNSTF  360
FSTFKCYGVS ATKLNDLCFS NVYADSFVVK GDDVRQIAPG QTGVIADYNY KLPDDFMGCV  420
LAWNTRNIDA TSTGNYNYKY RYLRHGKLRP FERDISNVPF SPDGKPCTPP ALNCYWPLND  480
YGFYTTTGIG YQPYRVVVLS FELLNAPATV CGPKLSTDLI KNQCVNFNFN GLTGTGVLTP  540
SSKRFQPFQQ FGRDVSDFTD SVRDPKTSEI LDISPCSFGG VSVITPGTNA SSEVAVLYQD  600
VNCTDVSTAI HADQLTPAWR IYSTGNNVFQ TQAGCLIGAE HVDTSYECDI PIGAGICASY  660
HTVSLLRSTS QKSIVAYTMS LGADSSIAYS NNTIAIPTNF SISITTEVMP VSMAKTSVDC  720
NMYICGDSTE CANLLLQYGS FCTQLNRALS GIAAEQDRNT REVFAQVKQM YKTPTLKYFG  780
GFNFSQILPD PLKPTKRSFI EDLLFNKVTL ADAGFMKQYG ECLGDINARD LICAQKFNGL  840
TVLPPLLTDD MIAAYTAALV SGTATAGWTF GAGAALQIPF AMQMAYRFNG IGVTQNVLYE  900
NQKQIANQFN KAISQIQESL TTTSTALGKL QDVVNQNAQA LNTLVKQLSS NFGAISSVLN  960
DILSRLDKVE AEVQIDRLIT GRLQSLQTYV TQQLIRAAEI RASANLAATK MSECVLGQSK  1020
RVDFCGKGYH LMSFPQAAPH GVVFLHVTYV PSQERNFTTA PAICHEGKAY FPREGVFVFN  1080
GTSWFITQRN FFSPQIITTD NTFVSGNCDV VIGIINNTVY DPLQPELDSF KEELDKYFKN  1140
HTSPDVDLGD ISGINASVVN IQKEIDRLNE VAKNLNESLI DLQELGKYEQ YIKWPW      1196

SEQ ID NO: 29           moltype = DNA  length = 3828
FEATURE                 Location/Qualifiers
misc_feature            1..3828
                        note = synthetic polynucleotide encoding
                         antigen_XXX_nCov_Spike_full_opt_h.sapiens_koz_deltaFurin
source                  1..3828
                        mol_type = other DNA
                        organism = synthetic construct
CDS                     7..3828
SEQUENCE: 29
gccaccatgt tcgtgtttct ggtgctgctg cctctggtgt ccagccagtg tgtgaacctg  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgacaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaacgac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgcgcgagt tcgtgttcaa gaacatcgac  600
ggctacttca agatctacag caagcacacc cctatcaacc tcgtgcggga tctgcctcag  660
ggcttctctg ctctggaacc cctggtggat ctgcccatcg gcatcaacat cacccggttt  720
cagacactgc tggccctgca cagaagctac ctgacacctg gcgatagcag cagcggatgg  780
acagctggtg ccgccgctta ctatgtgggc tacctgcagc ctagaacctt cctgctgaag  840
tacaacgaga acggcaccat caccgacgcc gtggattgtg ctctggatcc tctgagcgag  900
acaaagtgca ccctgaagtc cttcaccgtg gaaaagggca tctaccagac cagcaacttc  960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
```

```
tgctacggcg tgtcccctac caagctgaac gacctgtgct tcacaaacgt gtacgccgac   1200
agcttcgtga tccggggaga tgaagtgcgg cagattgccc ctggacagac aggcaagatc   1260
gccgactaca actacaagct gcccgacgag ttcaccggct gtgtgattgc ctggaacagc   1320
aacaacctgg actccaaagt cggcggcaac tacaattacc tgtaccggct gttccggaag   1380
tccaatctga agcccttcga gcgggacatc tccaccgaga tctatcaggc cggcagcacc   1440
ccttgtaacg gcgtgaagg cttcaactgc tacttcccac tgcagtccta cggctttcag   1500
cccacaaatg gcgtgggcta tcagccctac agagtggtgg tgctgagctt cgaactgctg   1560
catgcccctg ccacagtgtg cggccctaag aaaagcacca atctcgtgaa gaacaaatgc   1620
gtgaacttca acttcaacgg cctgaccggc accggcgtgc tgacagagag caacaagagg   1680
ttcctgccat tccagcagtt tggccgggat atccgccgata ccacagacgc cgttagagat   1740
ccccagacac tggaaatcct ggacatcacc ccttgcagct tcggcggagt gtctgtgatc   1800
accccctggca ccaacaccag caatcaggtg gcagtgctgt accaggacgt gaactgtacc   1860
gaagtgcccg tggccattca cgccgatcag ctgacaccta catggcgggt gtactccacc   1920
ggcagcaatg tgtttcagac cagagccggc tgtctgatcg gagccgagca cgtgaacaat   1980
agctacgagt gcgacatccc catcggcgct ggcatctgtg ccagctacca gacacagaca   2040
aacagccccg gaagcgccag ctctgtggcc agcagagca tcattgccta cacaatgtct   2100
ctgggcgccg agaacagcgt ggcctactcc aacaactcta tcgctatccc caccaacttc   2160
accatcagcg tgaccacaga gatcctgcct gtgtccatga ccaagaccag cgtggactgc   2220
accatgtaca tctgcggcga ttccaccgag tgctccaacc tgctgctgca gtacggcagc   2280
ttctgcaccc agctgaatag agccctgaca gggatcgccg tggaacagga caagaacacc   2340
caagaggtgt tcgcccaagt gaagcagatc tacaagaccc ctcctatcaa ggacttcggc   2400
ggcttcaatt tcagccagat tctgcccgat cctagcaagc ccaagtccag gagcttcatc   2460
gaggacctgc tgttcaacaa agtgacactg gccgacgccg gcttcatcaa gcagtatggc   2520
gattgtctgg gcgacattgc cgccagggat ctgatttgcg cccagaagtt taacggactg   2580
acagtgctgc ctcctctgct gaccgatgag atgatcgccc agtacacatc tgccctgctg   2640
gccggcacaa tcacaagcgg ctggacattt ggagctggcg ccgctctgca gatcccctt   2700
gctatgcaga tggcctaccg gttcaacggc atcggagtga cccagaatgt gctgtacgag   2760
aaccagaagc tgatcgccaa ccagttcaac agcgccatcg gcaagatcca ggacagcctg   2820
agcagcacag caagcgccct gggaaagctg caggacgtgg tcaaccagaa tgcccaggca   2880
ctgaacaccc tggtcaagca gctgtcctcc aacttcggcg ccatcagctc tgtgctgaac   2940
gatatcctga gcagactgga caaggtggaa gccgaggtgc agatcgacag actgatcacc   3000
ggaaggctgc agtccctgca gacctacgtt acccagcagc tgatcagagc cgccgagatt   3060
agagcctctg ccaatctggc cgccaccaag atgtctgagt gtgtgctggg ccagagcaag   3120
agagtggact tttgcggcaa gggctaccac ctgatgagct tccctcagtc tgcccctcac   3180
ggcgtggtgt ttctgcacgt gacatacgtg cccgctcaag agaagaattt caccaccgct   3240
ccagccatct gccacgacgg caaagcccac tttcctagag aaggcgtgtt cgtgtccaac   3300
ggcacccatt ggttcgtgac ccagcggaac ttctacgagc cccagatcat caccaccgac   3360
aacaccttcg tgtctggcaa ctgcgacgtc gtgatcggca ttgtgaacaa taccgtgtac   3420
gaccctctgc agcccgagct ggacagcttc aaagaggaac tggataagta ctttaagaac   3480
cacacaagcc ccgacgtgga cctgggcgat atcagcggaa tcaatgccag cgtcgtgaac   3540
atccagaaag agatcgaccg gctgaacgag gtggccaaga atctgaacga gagcctgatc   3600
gacctgcaag aactggggaa gtacgagcag tacatcaagt ggccctggta catctggctg   3660
ggctttatcg ccggactgat tgccatcgtg atggtcacaa tcatgctgtg ttgcatgacc   3720
agctgctgta gctgcctgaa gggctgttgt agctgtggca gctgctgcaa gttcgacgag   3780
gacgattctg agcccgtgct gaagggcgtg aaactgcact acacctga                3828

SEQ ID NO: 30        moltype = AA   length = 1273
FEATURE              Location/Qualifiers
REGION               1..1273
                     note = Synthetic Construct
source               1..1273
                     mol_type = protein
                     organism = synthetic construct
SEQUENCE: 30
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PGSASSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 31        moltype = DNA   length = 651
FEATURE              Location/Qualifiers
```

```
misc_feature            1..651
                        note = synthetic polynucleotide encoding
                          antigen_2a_nCovRDB_SPnCov_OPT_koz_Var1
source                  1..651
                        mol_type = other DNA
                        organism = synthetic constru

```
gtcgctaata tcaccaatct gtgccccttc ggcgaggtgt tcaatgccac cagattcgcc    120
tctgtgtacg cctggaaccg gaagcggatc agcaattgcg tggccgacta ctccgtgctg    180
tacaactccg ccagcttcag caccttcaag tgctacggcg tgtccnctac caagctgaac    240
gacctgtgct tcacaaacgt atacgccgac agcttcgtga tccggggaga tgaagtgcgg    300
cagattgccc ctggacagac aggcaatatc gccgactaca actacaagct gcccgacgac    360
ttcaccggct gtgtgattgc ctggaacagc aagaacctgg actccaaagt cggcggcaac    420
tacaattacc tgttccggct gttccggaag tccaatctga gcccttcga gcgggacatc    480
tccaccgaga tctatcaggc cggcaacacc ccttgtaacg gcgtgaaagg cttcaactgc    540
tactccccac tgcagtccta cggctttcag cccacatatg gcgtgggcta tcagccctac    600
agagtggtgg tgctgagctt cgaactgctg catgcccctg ccacagtgtg a             651
```

```
SEQ ID NO: 36             moltype = AA  length = 214
FEATURE                   Location/Qualifiers
REGION                    1..214
                          note = Synthetic Construct
source                    1..214
                          mol_type = protein
                          organism = synthetic construct
SEQUENCE: 36
MFVFLVLLPL VSSQCVNLVA NITNLCPFGE VFNATRFASV YAWNRKRISN CVADYSVLYN    60
SASFSTFKCY GVSPTKLNDL CFTNVYADSF VIRGDEVRQI APGQTGNIAD YNYKLPDDFT   120
GCVIAWNSKN LDSKVGGNYN YLFRLFRKSN LKPFERDIST EIYQAGNTPC NGVKGFNCYS   180
PLQSYGFQPT YGVGYQPYRV VVLSFELLHA PATV                               214
```

```
SEQ ID NO: 37             moltype = DNA  length = 651
FEATURE                   Location/Qualifiers
misc_feature              1..651
                          note = synthetic polynucleotide coding for
                            Antigen_2a_nCovRDB_SPnCov_OPT_koz_Var4
source                    1..651
                          mol_type = other DNA
                          organism = synthetic construct
CDS                       7..651
SEQUENCE: 37
gccaccatgt tcgtgtttct ggtgctgctg cctctggtgt ccagccagtg tgtgaacctg     60
gtcgctaata tcaccaatct gtgccccttc ggcgaggtgt tcaatgccac cagattcgcc    120
tctgtgtacg cctggaaccg gaagcggatc agcaattgcg tggccgacta ctccgtgctg    180
tacaactccg ccagcttcag caccttcaag tgctacggcg tgtcccctac caagctgaac    240
gacctgtgct tcacaaacgt atacgccgac agcttcgtga tccggggaga tgaagtgcgg    300
cagattgccc ctggacagac aggcaatatc gccgactaca actacaagct gcccgacgac    360
ttcaccggct gtgtgattgc ctggaacagc aagaacctgg actccaaagt cggcggcaac    420
tacaattacc ggtaccggct gttccggaag tccaatctga gcccttcga gcgggacatc    480
tccaccgaga tctatcaggc cggcaacacc ccttgtaacg gcgtgaaagg cttcaactgc    540
tactccccac tgcagtccta cggctttcag cccacatatg gcgtgggcta tcagccctac    600
agagtggtgg tgctgagctt cgaactgctg catgcccctg ccacagtgtg a             651
```

```
SEQ ID NO: 38             moltype = AA  length = 214
FEATURE                   Location/Qualifiers
REGION                    1..214
                          note = Synthetic Construct
source                    1..214
                          mol_type = protein
                          organism = synthetic construct
SEQUENCE: 38
MFVFLVLLPL VSSQCVNLVA NITNLCPFGE VFNATRFASV YAWNRKRISN CVADYSVLYN    60
SASFSTFKCY GVSPTKLNDL CFTNVYADSF VIRGDEVRQI APGQTGNIAD YNYKLPDDFT   120
GCVIAWNSKN LDSKVGGNYN YRYRLFRKSN LKPFERDIST EIYQAGNTPC NGVKGFNCYS   180
PLQSYGFQPT YGVGYQPYRV VVLSFELLHA PATV                               214
```

```
SEQ ID NO: 39             moltype = DNA  length = 3771
FEATURE                   Location/Qualifiers
misc_feature              1..3771
                          note = synthetic polynucleotide for
                            Antigen_1_nCov_Spike_full_opt_h.sapiens_koz_delta_Cter
source                    1..3771
                          mol_type = other DNA
                          organism = synthetic construct
CDS                       7..3771
SEQUENCE: 39
gccaccatgt tcgtgtttct ggtgctgctg cctctggtgt ccagccagtg tgtgaacctg     60
accaccagaa cacagctgcc tccagcctac accaacagct ttaccagagg cgtgtactac    120
cccgacaagg tgttcagatc cagcgtgctg cactctaccc aggacctgtt cctgcctttc    180
ttcagcaacg tgacctggtt ccacgccatc cacgtgtccg gcaccaatgg caccaagaga    240
ttcgacaacc ccgtgctgcc cttcaacgac ggggtgtact ttgccagcac cgagaagtcc    300
aacatcatca gaggctggat cttcggcacc acactggaca gcaagaccca gagcctgctg    360
atcgtgaaca acgccaccaa cgtggtcatc aaagtgtgcg agttccagtt ctgcaacgac    420
ccctttcctgg gcgtctacta ccacaagaac aacaagagct ggatggaaag cgagttccgg    480
gtgtacagca gcgccaacaa ctgcaccttc gagtacgtgt cccagccttt cctgatggac    540
ctggaaggca agcagggcaa cttcaagaac ctgcgcgagt tcgtgttcaa gaacatcgac    600
```

-continued

```
ggctacttca agatctacag caagcacacc cctatcaacc tcgtgcggga tctgcctcag  660
ggcttctctg ctctggaacc cctggtggat ctgcccatcg gcatcaacat cacccgtttt  720
cagcacactgc tggccctgca cagaagctac ctgacacctg gcgatagcag cagcggatgg  780
acagctggtg ccgccgctta ctatgtgggc tacctgcagc ctagaacctt cctgctgaag  840
tacaacgaga acggcaccat caccgacgcc gtggattgca tctctgatcc tctgagcgag  900
acaaagtgca ccctgaagtc cttcaccgtg aaaagggca tctaccagac cagcaacttc  960
cgggtgcagc ccaccgaatc catcgtgcgg ttccccaata tcaccaatct gtgccccttc 1020
ggcgaggtgt tcaatgccac cagattcgcc tctgtgtacg cctggaaccg aagcggatc  1080
agcaattgcg tggccgacta ctccgtgctg tacaactccg ccagcttcag cacctttcag 1140
tgctacggcg tgtcccctac caagctgaac gacctgtgct tcacaaacgt gtacgccgac 1200
agcttcgtga tccggggaga tgaagtgcgc cagattgccc ctggacagac aggcaagatc 1260
gccgactaca actacaagct gcccgacgac ttcaccggct gtgtgattgc ctggaacagc 1320
aacaacctgg actccaaagt cggcggcaac tacaattacc tgtaccggct gttccggaag 1380
tccaatctga agccttcga gcgggaacatc tccaccgaga tctatcaggc cggcagcacc 1440
ccttgtaacg gcgtgaagg cttcaactgc tacttccac tgcagtccta cggctttcag 1500
cccacaaatg gcgtgggcta tcagccctac agagtggtgg tgctgagctt cgaactgctg 1560
catgcccctg ccacagtgtg cggccctaag aaaagcacca atctcgtgaa gaacaaatgc 1620
gtgaacttca acttcaacgg cctgaccggc accggcgtgc tgacagagag caacaagaag 1680
ttcctgccat tccagcagtt tggccgggat atcgccgata ccacagacgc cgttagagat 1740
cccagacac tggaaatcct ggacatcacc ccttgcagct tcggcggagt gtctgtgatc 1800
acccctggca ccaacaccag caatcaggtg gcagtgctgt accaggacgt gaactgtacc 1860
gaagtgcccg tggccattca cgccgatcag ctgcacacta catggcgggt gtactccacc 1920
ggcagcaatg tgtttcagac cagagccggc tgtctgatcg gagccgagca cgtgaacaat 1980
agctacgagt gcgacatccc catcggcgct ggcatctgtg ccagctacca gacacagaca 2040
aacagcccca gacgggccag atctgtggcc agccagagca tcattgccta cacaatgtct 2100
ctgggcgccg agaacagcgt ggcctactcc aacaactcta tcgctatccc caccaacttc 2160
accatcagcg tgaccacaga gatcctgcct gtgtccatga ccaagaccag cgtggactgc 2220
accatgtaca tctgcggcga ttccaccgag tgctccaacc tgctgctgca gtacggcagc 2280
ttctgcaccc agctgaatag agccctgaca gggatcgccg tggaacagga caagaacacc 2340
caagagtgt tcgcccaagt gaagcagatc tacaagaccc ctcctatcaa ggacttcggc 2400
ggcttcaatt tcagccagat tctgcccgat cctagcaagc ccagcaagcg gagcttcatc 2460
gaggacctgc tgttcaacaa agtgacactg gccgacgccg gcttcatcaa gcagtatggc 2520
gattgtctgg gcgacattgc cgccaggat ctgatttgcg cccagaagtt taacggactg 2580
acagtgctgc ctcctctgct gaccgatgag atgatcgccc agtacactcc tgccctgctg 2640
gccggcacaa tcacaagcgg ctggacattt ggagctggcg ccgctctgca gatccccttt 2700
gctatgcaga tggcctaccg gttcaacggc atcggagtga cccagaatgt gctgtacgag 2760
aaccagaagc tgatcgccaa ccagttcaac agcgccatcg gcaagatcca ggacagcctg 2820
agcagcacag caagcgccct gggaaagctg caggacgtgg tcaaccagaa tgcccaggca 2880
ctgaacacc tggtcaagca gctgtcctcc aacttcggcg ccatcagctc tgtgctgaac 2940
gatatcctga gcagactgga caaggtggaa gccgaggtgc agatcgacag actgatcacc 3000
ggaaggctgc agtccctgca gacctacgtt acccagcagc tgatcagagc cgccgagatt 3060
agagcctctg ccaatctggc cgccaccaag atgtctgagt gtgtgctggg ccagagcaag 3120
agagtggact tttgcggcaa gggctaccac ctgatgagct tccctcagtc tgcccctcac 3180
ggcgtggtgt ttctgcacgt gacatacgtg cccgctcaag agaagaattt caccaccgct 3240
ccagccatct gccacgacgg caaagcccac tttcctagaa aggcgtgtt cgtgtccaac 3300
ggcacccatt ggttcgtgac ccagcggaac ttctacgagc ccagatcat caccaccgac 3360
aacaccttg tgtctggcaa ctgcgacgtc gtgatcggca ttgtgaacaa taccgtgtac 3420
gaccctctgc agcccgagct ggacagcttc aaagaggaac tggataagta ctttaagaac 3480
cacacaagcc ccgacgtgga cctgggcgat atcagcggaa tcaatgccag cgtcgtgaac 3540
atccagaaag agatcgaccg gctgaacgag gtggccaaga tctctgaacga gagcctgatc 3600
gacctgcaag aactgggaa gtacgagcag tacatcaagt ggccctggta catctgctg 3660
ggctttatcg ccggactgat tgccatcgtg atggtcacaa tcatgctgtg ttgcatgacc 3720
agctgctgta gctgcctgaa gggctgttgt agctgtggca gctgctgctg a         3771

SEQ ID NO: 40          moltype = AA   length = 1254
FEATURE                Location/Qualifiers
REGION                 1..1254
                       note = Synthetic Construct
source                 1..1254
                       mol_type = protein
                       organism = synthetic construct
SEQUENCE: 40
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
```

```
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCC        1254

SEQ ID NO: 41          moltype = DNA   length = 3828
FEATURE                Location/Qualifiers
misc_feature           1..3828
                       note = synthetic polynucleotide for
                       Antigen_1_nCov_Spike_full_opt_h.sapiens_koz_2P
source                 1..3828
                       mol_type = other DNA
                       organism = synthetic construct
CDS                    7..3828
SEQUENCE: 41
gccaccatgt tcgtgtttct ggtgctgctg cctctggtgt ccagccagtg tgtgaacctg    60
accaccagaa cacagctgcc tccagcctac accaacagct ttaccagagg cgtgtactac   120
cccgacaagg tgttcagatc cagcgtgctg cactctaccc aggacctgtt cctgcccttc   180
ttcagcaacg tgacctggtt ccacgccatc cacgtgtccg gcaccaatgg caccaagaga   240
ttcgacaacc ccgtgctgcc cttcaacgac ggggtgtact tgccagcac cgagaagtcc    300
aacatcatca gaggctggat cttcggcacc acactggaca gcaagaccca gagcctgctg   360
atcgtgaaca acgccaccaa cgtggtcatc aaagtgtgcg agttccagtt ctgcaacgac   420
cccttcctgg gcgtctacta ccacaagaac aacaagagct ggatggaaag cgagttccgc   480
gtgtacagca gcgccaacaa ctgcaccttc gagtacgtgt cccagccttt cctgatggac   540
ctggaaggca agcagggcaa cttcaagaac ctgcgcgagt tcgtgttcaa gaacatcgac   600
ggctacttca agatctacag caagcacacc cctatcaacc tcgtgcggga tctgcctcag   660
ggcttctctg ctctggaacc cctggtggat ctgcccatcg gcatcaacat cacccggttt   720
cagacactgc tggccctgca cagaagctac ctgacacctg gcgatagcag cagcggatgg   780
acagctggtg ccgccgctta ctatgtgggc tacctgcagc ctagaacctt cctgctgaag   840
tacaacgaga acggcaccat caccgacgcc gtggattgtg ctctggatcc tctgagcgag   900
acaaagtgca ccctgaagtc cttcaccgtg gaaagggca tctaccagac cagcaacttc   960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtccccta caagctgaac gacctgtgct tcacaaacgt gtacgccgac  1200
agcttcgtga tccggggaga tgaagtgcgc cagattgccc ctggacagac aggcaagatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga gccctctcga gcgggacatc tccaccgaga tctatcaggc cggcagcacc  1440
ccttgtaacg gcgtggaagg cttcaactgc tacttcccac tgcagtccta cggctttcag  1500
cccacaaatg gcgtgggcta tcagccctac agagtggtgg tgctgagctt cgaactgctg  1560
catgcccctg ccacagtgtg cggccctaag aaaagcacca atctcgtgaa gaacaaatgc  1620
gtgaacttca acttcaacgg cctgaccggc accggcgtgc tgacagagac caacaagaag  1680
ttcctgccat tccagcagtt tggccggat catcgccgata ccacagagcg cgttagagat  1740
ccccagacac tggaaatcct ggacatcacc ccttgcagct tcggcggagt gtctgtgatc  1800
accccctggc caacaccag caatcaggtg gcagtgctgt accaggacgt gaactgtacc  1860
gaagtgcccg tggccattca cgccgatcag ctgacaccca tgtggcggtt gtactccacc  1920
ggcagcaatg tgtttcagac cagagccggc tgtctgatcg gagccgagca cgtgaacaat  1980
agctacgagt gcgacatccc catcggcgct ggcatctgtg ccagctacca gacacagaca  2040
aacagcccca cgggccagat ctgtgggcc agccagagca tcattgccta caatgtgtct  2100
ctgggccgg agaacagcgt ggcctactcc aacaactcc tcgctatcc caccaacttc  2160
accatcagcg tgaccacaga gatcctgcct gtgtccatga ccaagaccag cgtggactgc  2220
accatgtaca tctgcggcga ttccaccgag tgctccaacc tgctgctgca gtacggcagc  2280
ttctgcaccc agctgaatag agccctgaca gggatcgccg tggaacagga caagaacacc  2340
caagaggtgt tcgcccaagt gaagcagatc tacaagacgc ctcctatcga ggacttcggc  2400
ggcttcaatt tcagccagat tctgcccgat cctagcaagc ccagcaagcg gagcttcatc  2460
gaggacctgc tgttcaacaa agtgacactg gccgacgccg gcttcatcaa gcagtatggc  2520
gattgtctgg gcgacattgc cgccaggat ctgatttgcg cccagaagtt taacggactg  2580
acagtgctgc ctcctctgct gaccgatgag atgatcgccc agtacacatc tgccctgctg  2640
gccggcacaa tcacaagcgg ctggacattt ggagctggcg ccgctctgca gatccccttt  2700
gctatgcaga tggcctaccg gttcaacggc atcggagtga cccagaatgt gctgtacgag  2760
aaccagaagc tgatcgccaa ccagttcaac agcgccatcg gcaagatcca ggacagcctg  2820
agcagcacag caagcgccct gggaaagctg caggacgtg tcaaccagaa tgcccaggca  2880
ctgaacaccc tggtcaagca gctgtcctcc aacttcggtg ccatcagctc tgtgctgaac  2940
gatatcctga gcagactgga cccgccgaa gccgaggtgc agatcgacag actgatcacc  3000
ggaaggctgc agtccctgca gacctacgtt acccagcagc tgatcagagc cgccgagatt  3060
agagcctctg ccaatctggc cgccaccaag atgtctgagt gtgtgctggg ccagagcaag  3120
agagtggact tttgcggcaa gggctaccac ctgatgagct tccctcagtc tgcccctcac  3180
ggcgtggtgt ttctgcacgt gacatacgtg cccgctcaga agaagatttt caccaccgct  3240
ccagccatct gccacgacgg caaagcccac tttcctagag aaggcgtgtt cgtgtccaac  3300
ggcacccatt ggttcgtgac ccagcggaac ttctacgagc cccagatcat caccaccgac  3360
aacaccttcg tgtctggcaa ctgcgacgtc gtgatcggca ttgtgaacaa taccgtgtac  3420
gacccttctg agcccgagct ggacagcttc aaggagaac tggataagta ctttaagaac  3480
cacacaagcc cggacgtgga cctgggcgat atcagcggaa tcaacgcctc tgtggtgaac  3540
atccagaaaa gatcgaccg gctgaacgag gtggccaaga tctgaacga gagcctgatc  3600
gacctgcaag aactggggaa gtacgagcag tacatcaagt ggccctggta catctggctg  3660
ggctttatcg ccggactgat tgccatcgtg atggtcacaa tcatgctgtg ttgcatgacc  3720
agctgctgta gctgcctgaa gggctgttgt agctgtggca gctgctgcaa gttcgacgag  3780
gacgattctg agcccgtgct gaagggcgtg aaactgcact acacctga              3828
```

```
SEQ ID NO: 42          moltype = AA  length = 1273
FEATURE                Location/Qualifiers
REGION                 1..1273
                       note = Synthetic Construct
source                 1..1273
                       mol_type = protein
                       organism = synthetic construct
SEQUENCE: 42
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 43          moltype = DNA  length = 3819
FEATURE                Location/Qualifiers
misc_feature           1..3819
                       note = synthetic polynucleotide for
                        Antigen_1_nCov_Spike_full_opt_h.sapiens_koz_UK
source                 1..3819
                       mol_type = other DNA
                       organism = synthetic construct
CDS                    7..3819
SEQUENCE: 43
gccaccatgt tcgtgtttct ggtgctgctg cctctggtgt ccagccagtg tgtgaacctg  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct accacaagaa caacaagagc tggatggaaa gcgagttccg ggtgtacagc  480
agcgccaaca actgcacctt cgagtacgtg tcccagcctt tcctgatgga cctggaaggc  540
aagcagggca acttcaagaa cctgcgcgag ttcgtgttca agaacatcga cggctacttc  600
aagatctaca gcaagcacac ccctatcaac ctcgtgcggg atctgcctca gggcttctct  660
gctctggaac ccctggtgga tctgcccatc ggcatcaaca tcacccggtt tcagacactg  720
ctggccctgc acagaagcta cctgacacct ggcgatagca gcagcggatg gacagctggt  780
gccgccgctt actatgtggg ctacctgcag cctagaacct tcctgctgaa gtacaacgag  840
aacggcacca tcaccgacgc cgtggattgt gctctggatc ctctgagcga gacaaagtgc  900
accctgaagt ccttcaccgt ggaaaagggc atctaccaga ccagcaactt ccgggtgcag  960
cccaccgaat ccatcgtgcg gttccccaat atcaccaatc tgtgcccctt cggcgaggtg  1020
ttcaatgcca ccagattcgc ctctgtgtac gcctggaacc ggaagcggat cagcaattgc  1080
gtggccgact actccgtgct gtacaactcc gccagcttca gcaccttcaa gtgctacggc  1140
gtgtccccta ccaagctgaa cgacctgtgc ttcacaaacg tgtacgccga cagcttcgtg  1200
atccggggag atgaagtgcg gcagattgcc cctggacaga caggcaagat cgccgactac  1260
aactacaagc tgcccgacga cttcaccggc tgtgtgattg cctggaacag caacaacctg  1320
gactccaaag tcggcggcaa ctacaattac ctgtaccggc tgttccggaa gtccaatctg  1380
aagcccttcg agcgggacat ctccaccgag atctatcagg ccggcagcac cccttgtaac  1440
ggcgtggaag gcttcaactg ctacttccca ctgcagtcct acggctttca gcccacatat  1500
ggcgtgggct atcagcccta cagagtggtg gtgctgagct tcgaactgct gcatgcccct  1560
gccacagtgt gcggccctaa gaaaagcacc aatctcgtga agaacaaatg cgtgaacttc  1620
aacttcaacg gcctgaccgg caccggcgtg ctgacagaga gcaacaagaa gttcctgcca  1680
ttccagcagt ttggccggga tatcgacgat accacagacg ccgttagaga tccccagaca  1740
ctggaaatcc tggacatcac cccttgcagc ttcggcggag tgtctgtgat cacccctggc  1800
accaacacca gcaatcaggt ggcagtgctg taccagggcg tgaactgtac cgaagtgccc  1860
gtggccattc acgccgatca gctgacacct acatggcggg tgtactccac cggcagcaat  1920
gtgtttcaga ccagagccgg ctgtctgatc ggagccgagc acgtgaacaa tagctacgag  1980
tgcgacatcc ccatcggcgc tggcatctgt gccagctacc agacacagac aaacagccac  2040
agacgggcca gatctgtggc cagccagagc atcattgcct acacaatgtc tctgggcgcc  2100
gagaacagcg tggcctactc caacaactct atcgctatcc ccatcaactt caccatcagc  2160
gtgaccacag agatcctgcc tgtgtccatg accaagacca gcgtggactg caccatgtac  2220
```

-continued

```
atctgcggcg attccaccga gtgctccaac ctgctgctgc agtacggcag cttctgcacc  2280
cagctgaata gagccctgac agggatcgcc gtggaacagg acaagaacac ccaagaggtg  2340
ttcgcccaag tgaagcagat ctacaagacc cctcctatca aggacttcgg cggcttcaat  2400
ttcagccaga ttctgcccga tcctagcaag cccagcaagc ggagcttcat cgaggacctg  2460
ctgttcaaca aagtgacact ggccgacgcc ggcttcatca agcagtatgg cgattgtctg  2520
ggcgacattg ccgccaggga tctgatttgc gcccagaagt ttaacggact gacagtgctg  2580
cctcctctgc tgaccgatga gatgatcgcc cagtacacat ctgccctgct ggccggcaca  2640
atcacaagcg gctggacatt tggagctggc gccgctctgc agatcccctt tgctatgcag  2700
atggcctacc ggttcaacgg catcggagtg acccagaatg tgctgtacga gaaccagaag  2760
ctgatcgcca accagttcaa cagcgccatc ggcaagatcc aggacagcct gagcagcaca  2820
gcaagcgccc tgggaaagct gcaggacgtg gtcaaccaga atgcccaggc actgaacacc  2880
ctggtcaagc agctgtcctc caacttcggc gccatcagct ctgtgctgaa cgatatcctg  2940
gccagactgg acaaggtgga agccgaggtg cagatcgaca gactgatcac cggaaggctg  3000
cagtccctgc agacctacgt tacccagcag ctgatcagag ccgccgagat tagagcctct  3060
gccaatctgg ccgccaccaa gatgtctgag tgtgtgctgg gccagagcaa gagagtggac  3120
ttttgcggca agggctacca cctgatgagc ttccctcagt ctgcccctca cggcgtggtg  3180
tttctgcacg tgacatacgt gcccgctcaa gagaagaatt tcaccaccgc tccagccatc  3240
tgccacgacg gcaaagccca ctttcctaga gaaggcgtgt tcgtgtccaa cggcacccat  3300
tggttcgtga cccagcggaa cttctacgag ccccagatca tcaccaccca caacaccttc  3360
gtgtctggca actgcgacgt cgtgatcggc attgtgaaca ataccgtgta cgaccctctg  3420
cagcccgagc tggacagctt caaagaggaa ctggataagt actttaagaa ccacacaagc  3480
cccgacgtgg acctgggcga tatcagcgga atcaatgcca gcgtcgtgaa catccagaaa  3540
gagatcgacc ggctgaacga ggtggccaag aatctgaacg agagcctgat cgacctgcaa  3600
gaactgggga agtacgagca gtacatcaag tggccctggt acatctggct gggctttatc  3660
gccggactga ttgccatcgt gatggtcaca atcatgctgt gttgcatgac cagctgctgt  3720
agctgcctga agggctgttg tagctgtggc agctgctgca agttcgacga ggacgattct  3780
gagcccgtgc tgaagggcgt gaaactgcac tacacctga                         3819

SEQ ID NO: 44           moltype = AA  length = 1270
FEATURE                 Location/Qualifiers
REGION                  1..1270
                        note = Synthetic Construct
source                  1..1270
                        mol_type = protein
                        organism = synthetic construct
SEQUENCE: 44
MFVFLVLLPL VSSQCVNLTT RTQLPPAYTN SFTRGVYYPD KVFRSSVLHS TQDLFLPFFS  60
NVTWFHAISG TNGTKRFDNP VLPFNDGVYF ASTEKSNIIR GWIFGTTLDS KTQSLLIVNN  120
ATNVVIKVCE FQFCNDPFLG VYHKNNKSWM ESEFRVYSSA NNCTFEYVSQ PFLMDLEGKQ  180
GNFKNLREFV FKNIDGYFKI YSKHTPINLV RDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGKIADYNY  420
KLPDDFTGCV IAWNSNNLDS KVGGNYNYLY RLFRKSNLKP FERDISTEIY QAGSTPCNGV  480
EGFNCYFPLQ SYGFQPTYGV GYQPYRVVVL SFELLHAPAT VCGPKKSTNL VKNKCVNFNF  540
NGLTGTGVLT ESNKKFLPFQ QFGRDIDDTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSHRR ARSVASQSII AYTMSLGAEN SVAYSNNSIA IPINFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILAR LDKVEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTHNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 45           moltype = DNA  length = 3762
FEATURE                 Location/Qualifiers
misc_feature            1..3762
                        note = synthetic polynucleotide for
                         Antigen_1_nCov_Spike_full_opt_h.sapiens_koz_UK_delta_Cter
source                  1..3762
                        mol_type = other DNA
                        organism = synthetic construct
CDS                     7..3762
SEQUENCE: 45
gccaccatgt tcgtgtttct ggtgctgctg cctctggtgt ccagccagtg tgtgaacctg  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct accacaagaa caacaagagc tggatggaaa gcgagttccg ggtgtacagc  480
agcgccaaca actgcacctt cgagtacgtg tcccagcctt tcctgatgga cctggaaggc  540
aagcagggca acttcaagaa cctgcgcgag ttcgtgttca agaacatcga cggctacttc  600
```

```
aagatctaca gcaagcacac ccctatcaac ctcgtgcggg atctgcctca gggcttctct   660
gctctggaac ccctggtgga tctgcccatc ggcatcaaca tcacccggtt tcagacactg   720
ctggccctgc acagaagcta cctgacacct ggcgatagca gcagcggatg gacagctggt   780
gccgccgctt actatgtggg ctacctgcag cctagaacct tcctgctgaa gtacaacgag   840
aacggcacca tcaccgacgc cgtggattgt gctctggatc ctctgagcga gacaaagtgc   900
accctgaagt ccttcaccgt ggaaaagggc atctaccaga ccagcaactt ccgggtgcag   960
cccaccgaat ccatcgtgcg gttccccaat atcaccaatc tgtgccccct cggcgaggtg  1020
ttcaatgcca ccagattcgc ctctgtgtac gcctggaacc ggaagcggat cagcaattgc  1080
gtggccgact actccgtgct gtacaactcc gccagcttca gcacctttaa gtgctacggc  1140
gtgtcccctca ccaagctgaa cgacctgtgc ttcacaaacg tgtacgccga cagcttcgtg  1200
atccggggag atgaagtgcg gcagattgcc cctggacaga caggcaagat cgccgactac  1260
aactacaagc tgcccgacga cttcaccggc tgtgtgattg cctggaacag caacaacctg  1320
gactccaaag tcggcggcaa ctacaattac ctgtaccggc tgttccggaa gtccaatctg  1380
aagcccttcg agcgggacat ctccaccgag atctatcagg ccggcagcac cccttgtaac  1440
ggcgtggaag gcttcaactg ctacttccca ctgcagtcct acggctttca gcccacatat  1500
ggcgtgggct atcagcccta cagagtggtg gtgctgagct tcgaactgct gcatgcccct  1560
gccacagtgt gcggccctaa gaaaagcacc aatctcgtga agaacaaatg cgtgaacttc  1620
aacttcaacg gcctgaccgg caccggcgtg ctgacagaga gcaacaagaa gttcctgcca  1680
ttccagcagt ttggccggga tatcgacgat accacagacg ccgttagaga tcccagaca   1740
ctggaaatcc tggacatcac cccttgcagc ttcggcggag tgtctgtgat cacccctggc  1800
accaacacca gcaatcaggt ggcagtgctg taccaggggcg tgaactgtac cgaagtgccc  1860
gtggccattc acgccgatca gctgacacct acatggcggt tgtactccac cggcagcaat  1920
gtgtttcaga ccagagccgg ctgtctgatc ggagccgagc acgtgaacaa tagctacgag  1980
tgcgacatcc ccatcggcgc tggcatctgt gccagctacc agacacagac aaacagccac  2040
agacgggcca gatctgtggc cagccagagc atcattgcct acacaatgtc tctgggcgcc  2100
gagaacagcg tggcctactc caacaacttc atcgctatcc ccatcaactt caccatcagc  2160
gtgaccacag atactgctgcc tgtgtccatg accaagacca gcgtggactg caccatgtac  2220
atctgcggcg attccaccga gtgctccaac ctgctgctgc agtacggcag cttctgcacc  2280
cagctgaata gagccctgac agggatcgcc gtggaacagg acaagaacac ccaagaggtg  2340
ttcgcccaag tgaagcagat ctacaagacc cctcctatca aggacttcgg cggcttcaat  2400
ttcagccaga tctctgcccga tcctagcaag cccagcaagc ggagcttcat cgaggacctg  2460
ctgttcaaca aagtgacact ggccgacgcc ggcttcatca agcagtatgg cgattgtctg  2520
ggcgacattg ccgccaggga tctgatttgc gcccagaagt taacggactg acagtgctgc  2580
cctcctctgc tgaccgatga gatgatccag cagtacacat ctgccctgct ggccggcaca  2640
atcacaagcg gctggacatt tggagctggc gccgctctgc agatccccttgcta tgcag     2700
atggcctacc ggttcaacgg catcggagtg acccagaatg tgctctacga gaaccagaag  2760
ctgatcgcca accagttcaa cagcgccatc ggcaagatcc aggacagcct gagcagcaca  2820
gcaagcgccc tgggaaaagct gcaggacgtg gtcaaccaga atgcccaggc actgaacacc  2880
ctggtcaagc agctgtcctc caacttcggc gccatcagct ctgtgctgaa cgatatcctg  2940
gccagactgg acaaggtgga agccgaggtg cagatcgaca gactgatcac cggaaggctg  3000
cagtccctgc agacctacgt tacccagcag ctgatcagag ccgccgagat tagagcctct  3060
gccaatctgg ccgccaccaa gatgtctgag tgtgtgctgg ccagagcaa gagagtggac  3120
ttcggtggca gtacgagca cctgatgagc ttccctcagt ctgcccctca cggcgtggtg  3180
tttctgcacg tgacatacgt gcccgctcaa gagaagaatt tcaccaccgc tccagccatc  3240
tgccacgacg gcaaagccca ctttcctaga aaggcgtgt cgtgtccaa cggcacccat  3300
tggttcgtga cccagcggaa cttctacgag ccccagatca tcaccaccca aacaccttc   3360
gtgtctggca actgcgacgt cgtgatcggc attgtgaaca ataccgtgta cgaccctctg  3420
cagcccgagc tggacagctt caaagaggaa ctggataagt actttaagaa ccacacaagc  3480
cccgacgtgg acctgggcga tatcagcgga atcaatgcca cgtcgtgaa catccagaaa  3540
gagatcgacc ggctgaacga ggtggccaag aatctgaacg agagcctgat cgacctgcaa  3600
gaactgggga gtacgagca gtacatcaag tggccctgct acatctggct gggctttatc  3660
gccggactga ttgccatcgt gatggtcaca atcatgctgt gttgcatgac cagctgctgt  3720
agctgcctga agggctgttg tagctgtggc agctgctgct ga                     3762
```

| SEQ ID NO: 46 | moltype = AA length = 1251 |
|---|---|
| FEATURE | Location/Qualifiers |
| REGION | 1..1251 |
| | note = Synthetic Construct |
| source | 1..1251 |
| | mol_type = protein |
| | organism = synthetic construct |

SEQUENCE: 46
```
MFVFLVLLPL VSSQCVNLTT RTQLPPAYTN SFTRGVYYPD KVFRSSVLHS TQDLFLPFFS    60
NVTWFHAISG TNGTKRFDNP VLPFNDGVYF ASTEKSNIIR GWIFGTTLDS KTQSLLIVNN   120
ATNVVIKVCE FQFCNDPFLG VYHKNNKSWM ESEFRVYSSA NNCTFEYVSQ PFLMDLEGKQ   180
GNFKNLREFV FKNIDGYFKI YSKHTPINLV RDLPQGFSAL EPLVDLPIGI NITRFQTLLA   240
LHRSYLTPGD SSSGWTAGAA AYYVGYLQPR TFLLKYNENG TITDAVDCAL DPLSETKCTL   300
KSFTVEKGIY QTSNFRVQPT ESIVRFPNIT NLCPFGEVFN ATRFASVYAW NRKRISNCVA   360
DYSVLYNSAS FSTFKCYGVS PTKLNDLCFT NVYADSFVIR GDEVRQIAPG QTGKIADYNY   420
KLPDDFTGCV IAWNSNNLDS KVGGNYNYLY RLFRKSNLKP FERDISTEIY QAGSTPCNGV   480
EGFNCYFPLQ SYGFQPTYGV GYQPYRVVVL SFELLHAPAT VCGPKKSTNL VKNKCVNFNF   540
NGLTGTGVLT ESNKKFLPFQ QFGRDIDDTT DAVRDPQTLE ILDITPCSFG GVSVITPGTN   600
TSNQVAVLYQ GVNCTEVPVA IHADQLTPTW RVYSTGSNVF QTRAGCLIGA EHVNNSYECD   660
IPIGAGICAS YQTQTNSHRR ARSVASQSII AYTMSLGAEN SVAYSNNSIA IPINFTISVT   720
TEILPVSMTK TSVDCTMYIC GDSTECSNLL LQYGSFCTQL NRALTGIAVE QDKNTQEVFA   780
QVKQIYKTPP IKDFGGFNFS QILPDPSKPS KRSFIEDLLF NKVTLADAGF IKQYGDCLGD   840
IAARDLICAQ KFNGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN QNAQALNTLV   960
KQLSSNFGAI SSVLNDILAR LDKVEAEVQI DRLITGRLQS LQTYVTQQLI RAAEIRASAN  1020
```

-continued

```
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTHNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC C           1251

SEQ ID NO: 47           moltype = DNA  length = 3819
FEATURE                 Location/Qualifiers
misc_feature            1..3819
                        note = synthetic polynucleotide for
                         Antigen_1_nCov_Spike_full_opt_h.sapiens_koz_UK_2P
source                  1..3819
                        mol_type = other DNA
                        organism = synthetic construct
CDS                     7..3819
SEQUENCE: 47
gccaccatgt tcgtgtttct ggtgctgctg cctctggtgt ccagccagtg tgtgaacctg  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct accacaagaa caacaagagc tggatggaaa gcgagttccg ggtgtacagc  480
agcgccaaca actgcacctt cgagtacgtg tcccagcctt tcctgatgga cctggaaggc  540
aagcagggca acttcaagaa cctgcgcgag ttcgtgttca agaacatcga cggctacttc  600
aagatctaca gcaagcacac ccctatcaac ctcgtgcggg atctgcctca gggcttctct  660
gctctggaac ccctggtgga tctgcccatc ggcatcaaca tcacccggtt tcagacactg  720
ctggccctgc acagaagcta cctgacacct ggcgatagca gcagcggatg gacagctggt  780
gccgccgctt actatgtggg ctacctgcag cctagaacct tcctgctgaa gtacaacgag  840
aacggcacca tcaccgacgc cgtggattgt gctctggatc ctctgagcga gacaaagtgc  900
accctgaagt ccttcaccgt ggaaaagggc atctaccaga ccagcaactt ccgggtgcag  960
cccaccgaat ccatcgtgcg gttccccaat atcaccaatc tgtgcccctt cggcgaggtg  1020
ttcaatgcca ccagattcgc ctctgtgtac gcctggaacc ggaagcggat cagcaattgc  1080
gtggccgact actccgtgct gtacaactcc gccagcttca gcaccttcaa gtgctacggc  1140
gtgtccccta ccaagctgaa cgacctgtgc ttcacaaacg tgtacgccga cagcttcgtg  1200
atccggggag atgaagtgcg gcagattgcc cctggacaga caggcaagat cgccgactac  1260
aactacaagc tgcccgacga cttcaccggc tgtgtgattg cctggaacag caacaacctg  1320
gactccaaag tcggcggcaa ctacaattac ctgtaccggc tgttccggaa gtccaatctg  1380
aagcccttcg agcgggacat ctccaccgag atctatcagg ccggcagcac cccttgtaac  1440
ggcgtggaag gcttcaactg ctacttccca ctgcagtcct acggctttca gcccacatat  1500
ggcgtgggct atcagcccta cagagtggtg gtgctgagct tcgaactgct gcatgcccct  1560
gccacagtgt gcggccctaa gaaaagcacc aatctcgtga agaacaaatg cgtgaacttc  1620
aacttcaacg gcctgaccgg caccggcgtg ctgacagaga gcaacaagaa gttcctgcca  1680
ttccagcagt ttggccggga tatcgacgat accacagacg ccgttagaga tccccagaca  1740
ctggaaatcc tggacatcac cccttgcagc ttcggcggag tgtctgtgat cacccctggc  1800
accaacacca gcaatcaggt ggcagtgctg taccagggcg tgaactgtac cgaagtgccc  1860
gtggccattc acgccgatca gctgacacct acatggcggg tgtactccac cggcagcaat  1920
gtgtttcaga ccagagccgg ctgtctgatc ggagccgagc acgtgaacaa tagctacgag  1980
tgcgacatcc ccatcggcgc tggcatctgt gccagctacc agacacagac aaacagccac  2040
agacgggcca gatctgtggc cagccagagc atcattgcct acacaatgtc tctgggcgcc  2100
gagaacagcg tggcctactc caacaactct atcgctatcc ccatcaactt caccatcagc  2160
gtgaccacag agatcctgcc tgtgtccatg accaagacca gcgtggactg caccatgtac  2220
atctgcggcg attccaccga gtgctccaac ctgctgctgc agtacggcag cttctgcacc  2280
cagctgaata gagccctgac agggatcgcc gtggaacagg acaagaacac ccaagaggtg  2340
ttcgcccaag tgaagcagat ctacaagacc cctcctatca aggacttcgg cggcttcaat  2400
ttcagccaga ttctgcccga tcctagcaag cccagcaagc ggagcttcat cgaggacctg  2460
ctgttcaaca aagtgacact ggccgacgcc ggcttcatca agcagtatgg cgattgtctg  2520
ggcgacattg ccgccaggga tctgatttgc gcccagaagt ttaacggact gacagtgctg  2580
cctcctctgc tgaccgatga gatgatcgcc cagtacacat ctgccctgct ggccggcaca  2640
atcacaagcg gctggacatt tggagctggc gccgctctgc agatcccctt tgctatgcag  2700
atggcctacc ggttcaacgg catcggagtg acccagaatg tgctgtacga gaaccagaag  2760
ctgatcgcca accagttcaa cagcgccatc ggcaagatcc aggacagcct gagcagcaca  2820
gcaagcgccc tgggaaagct gcaggacgtg gtcaaccaga atgcccaggc actgaacacc  2880
ctggtcaagc agctgtcctc caacttcggc gccatcagct ctgtgctgaa cgatatcctg  2940
gccagactgg acccgccgga agccgaggtg cagatcgaca gactgatcac cggaaggctg  3000
cagtccctgc agacctacgt tacccagcag ctgatcagag ccgccgagat tagagcctct  3060
gccaatctgg ccgccaccaa gatgtctgag tgtgtgctgg gccagagcaa gagagtggac  3120
ttttgcggca agggctacca cctgatgagc ttccctcagt ctgcccctca cggcgtggtg  3180
tttctgcacg tgacatacgt gcccgctcaa gagaagaatt tcaccaccgc tccagccatc  3240
tgccacgacg gcaaagccca ctttcctaga gaaggcgtgt tcgtgtccaa cggcacccat  3300
tggttcgtga cccagcggaa cttctacgag ccccagatca tcaccaccca caacaccttc  3360
gtgtctggca actgcgacgt cgtgatcggc attgtgaaca ataccgtgta cgaccctctg  3420
cagcccgagc tggacagctt caaagaggaa ctggataagt actttaagaa ccacacaagc  3480
cccgacgtgg acctgggcga tatcagcgga atcaatgcca gcgtcgtgaa catccagaaa  3540
gagatcgacc ggctgaacga ggtggccaag aatctgaacg agagcctgat cgacctgcaa  3600
gaactgggga agtacgagca gtacatcaag tggccctggt acatctggct gggctttatc  3660
gccggactga ttgccatcgt gatggtcaca atcatgctgt gttgcatgac cagctgctgt  3720
agctgcctga agggctgttg tagctgtggc agctgctgca agttcgacga ggacgattct  3780
gagcccgtgc tgaagggcgt gaaactgcac tacacctga                         3819
```

```
SEQ ID NO: 48          moltype = AA  length = 1270
FEATURE                Location/Qualifiers
REGION                 1..1270
                       note = Synthetic Construct
source                 1..1270
                       mol_type = protein
                       organism = synthetic construct
SEQUENCE: 48
MFVFLVLLPL VSSQCVNLTT RTQLPPAYTN SFTRGVYYPD KVFRSSVLHS TQDLFLPFFS  60
NVTWFHAISG TNGTKRFDNP VLPFNDGVYF ASTEKSNIIR GWIFGTTLDS KTQSLLIVNN  120
ATNVVIKVCE FQFCNDPFLG VYHKNNKSWM ESEFRVYSSA NNCTFEYVSQ PFLMDLEGKQ  180
GNFKNLREFV FKNIDGYFKI YSKHTPINLV RDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGKIADYNY  420
KLPDDFTGCV IAWNSNNLDS KVGGNYNYLY RLFRKSNLKP FERDISTEIY QAGSTPCNGV  480
EGFNCYFPLQ SYGFQPTYGV GYQPYRVVVL SFELLHAPAT VCGPKKSTNL VKNKCVNFNF  540
NGLTGTGVLT ESNKKFLPFQ QFGRDIDDTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSHRR ARSVASQSII AYTMSLGAEN SVAYSNNSIA IPINFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILAR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTHNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                    1270

SEQ ID NO: 49          moltype = DNA  length = 3762
FEATURE                Location/Qualifiers
misc_feature           1..3762
                       note = synthetic polynucleotide for
                        Antigen_1_nCov_Spike_full_opt_h.sapiens_koz_UK_2P_delta_Cte
                        r
source                 1..3762
                       mol_type = other DNA
                       organism = synthetic construct
CDS                    7..3762
SEQUENCE: 49
gccaccatgt tcgtgtttct ggtgctgctg cctctggtgt ccagccagtg tgtgaacctg  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct accacaagaa caacaagagc tggatggaaa gcgagttccg ggtgtacagc  480
agcgccaaca actgcacctt cgagtacgtg tcccagcctt tcctgatgga cctggaaggc  540
aagcagggca acttcaagaa cctgcgcgag ttcgtgttca agaacatcga cggctacttc  600
aagatctaca gcaagcacac ccctatcaac ctcgtgcggg atctgcctca gggcttctct  660
gctctggaac ccctggtgga tctgcccatc ggcatcaaca tcacccggtt tcagacactg  720
ctggccctgc acagaagcta cctgacacct ggcgatagca gcagcggatg gacagctggt  780
gccgccgctt actatgtggg ctacctgcag cctagaacct tcctgctgaa gtacaacgag  840
aacggcacca tcaccgacgc cgtggattgt gctctggatc ctctgagcga gacaaagtgc  900
accctgaagt ccttcaccgt ggaaaagggc atctaccaga ccagcaactt ccgggtgcag  960
cccaccgaat ccatcgtgcg gttccccaat atcaccaatc tgtgcccctt cggcgaggtg  1020
ttcaatgcca ccagattcgc ctctgtgtac gcctggaacc ggaagcggat cagcaattgc  1080
gtggccgact actccgtgct gtacaactcc gccagcttca gcaccttcaa gtgctacggc  1140
gtgtccccta ccaagctgaa cgacctgtgc ttcacaaacg tgtacgccga cagcttcgtg  1200
atccgggggag atgaagtgcg gcagattgcc cctggacaga caggcaagat cgccgactac  1260
aactacaagc tgcccgacga cttcaccggc tgtgtgattg cctggaacag caacaacctg  1320
gactccaaag tcggcggcaa ctacaattac ctgtaccggc tgttccggaa gtccaatctg  1380
aagcccttcg agcgggacat ctccaccgag atctatcagg ccggcagcac cccttgtaac  1440
ggcgtggaag gcttcaactg ctacttccca ctgcagtcct acggctttca gcccacatat  1500
ggcgtgggct atcagcccta cagagtggtg gtgctgagct tcgaactgct gcatgcccct  1560
gccacagtgt gcggccctaa gaaaagcacc aatctcgtga agaacaaatg cgtgaacttc  1620
aacttcaacg gcctgaccgg caccggcgtg ctgacagaga gcaacaagaa gttcctgcca  1680
ttccagcagt ttggccggga tatcgacgat accacagacg ccgttagaga tccccagaca  1740
ctggaaatcc tggacatcac cccttgcagc ttcggcggag tgtctgtgat cacccctggc  1800
accaacacca gcaatcaggt ggcagtgctg taccagggcg tgaactgtac cgaagtgccc  1860
gtggccattc acgccgatca gctgacacct acatggcggg tgtactccac cggcagcaat  1920
gtgtttcaga ccagagccgg ctgtctgatc ggagccgagc acgtgaacaa tagctacgag  1980
tgcgacatcc ccatcggcgc tggcatctgt gccagctacc agacacagac aaacagccac  2040
agacgggcca gatctgtggc cagccagagc atcattgcct acacaatgtc tctgggcgcc  2100
gagaacagcg tggcctactc caacaactct atcgctatcc ccatcaactt caccatcagc  2160
```

```
gtgaccacag agatcctgcc tgtgtccatg accaagacca gcgtggactg caccatgtac   2220
atctgcggcg attccaccga gtgctccaac ctgctgctgc agtacggcag cttctgcacc   2280
cagctgaata gagccctgac agggatcgcc gtggaacagg acaagaacac ccaagaggtg   2340
ttcgcccaag tgaagcagat ctacaagacc cctcctatca aggacttcgg cggcttcaat   2400
ttcagccaga ttctgcccga tcctagcaag cccagcaagc ggagcttcat cgaggacctg   2460
ctgttcaaca aagtgacact ggccgacgcc ggcttcatca gcagtatgg cgattgtctg   2520
ggcgacattg ccgccaggga tctgatttgc gcccagaagt ttaacggact gacagtgctg   2580
cctcctctgc tgaccgatga gatgatcgcc cagtacacat ctgccctgct ggccggcaca   2640
atcacaagcg gctggacatt tggagcggc gccgctctgc agatccccctt tgctatgcag   2700
atggcctacc ggttcaacgg catcggagtg acccagaatg tgctgtacga gaaccagaag   2760
ctgatcgcca accagttcaa cagcgccatc ggcaagatcc aggacagcct gagcagcaca   2820
gcaagcgccc tggaaagct gcaggacgtg gtcaaccaga atgcccaggc actgaacacc   2880
ctggtcaagc agctgtcctc caacttcggc gccatcagct ctgtgctgaa cgatatcctg   2940
gccagactgg acccgccgga agcgaggtg cagatcgaca gactgatcac cggaaggctg   3000
cagtccctgc agacctacgt tacccagcag ctgatcagaa ccgccgagat tagagcctct   3060
gccaatctgg ccgccaccaa gatgtctgag tgtgtgctgg ccagagcaa agagtggac   3120
ttttgcggca agggctacca cctgatgagc ttccctcagt ctgcccctca cggcgtggtg   3180
tttctgcacg tgacatacgt gcccgctcaa gagaagaatt tcaccaccgc tccagccatc   3240
tgccacgacg gcaaagccca cttcctaga aaggcgtgt tcgtgtccaa cggcacccat   3300
tggttcgtga cccagcggaa cttctacgag ccccagatca tcaccaccca aacaccttc   3360
gtgtctgcaa actgcgacgt cgtgatcggc attgtgaaca ataccgtgta cgaccctctg   3420
cagcccgagc tggacagctt caaagaggaa ctggataagt acttttaagaa ccacacaagc   3480
cccgacgtgg acctgggcga tatcagcgga atcaatgcca gcgtcgtgaa catccagaaa   3540
gagatcgacc ggctgaacga ggtggccaag aatctgaacg agagcctgat cgacctgcaa   3600
gaactgggga agtacgagca gtacatcaag tggcccctggt acatctggct gggctttatc   3660
gccggactga ttgccatcgt gatggtcaca atcatgctgt gttgcatgac cagctgctgt   3720
agctgcctga agggctgttg tagctgtggc agctgctgct ga                      3762

SEQ ID NO: 50          moltype = AA  length = 1251
FEATURE                Location/Qualifiers
REGION                 1..1251
                       note = Synthetic Construct
source                 1..1251
                       mol_type = protein
                       organism = synthetic construct
SEQUENCE: 50
MFVFLVLLPL VSSQCVNLTT RTQLPPAYTN SFTRGVYYPD KVFRSSVLHS TQDLFLPFFS     60
NVTWFHAISG TNGTKRFDNP VLPFNDGVYF ASTEKSNIIR GWIFGTTLDS KTQSLLIVNN    120
ATNVVIKVCE FQFCNDPFLG VYHKNNKSWM ESEFRVYSSA NNCTFEYVSQ PFLMDLEGKQ   180
GNFKNLREFV FKNIDGYFKI YSKHTPINLV RDLPQGFSAL EPLVDLPIGI NITRFQTLLA   240
LHRSYLTPGD SSSGWTAGAA AYYVGYLQPR TFLLKYNENG TITDAVDCAL DPLSETKCTL   300
KSFTVEKGIY QTSNFRVQPT ESIVRFPNIT NLCPFGEVFN ATRFASVYAW NRKRISNCVA   360
DYSVLYNSAS FSTFKCYGVS PTKLNDLCFT NVYADSFVIR GDEVRQIAPG QTGKIADYNY   420
KLPDDFTGCV IAWNSNNLDS KVGGNYNYLY RLFRKSNLKP FERDISTEIY QAGSTPCNGV   480
EGFNCYFPLQ SYGFQPTYGV GYQPYRVVVL SFELLHAPAT VCGPKKSTNL VKNKCVNFNF   540
NGLTGTGVLT ESNKKFLPFQ QFGRDIDDTT DAVRDPQTLE ILDITPCSFG GVSVITPGTN   600
TSNQVAVLYQ GVNCTEVPVA IHADQLTPTW RVYSTGSNVF QTRAGCLIGA EHVNNSYECD   660
IPIGAGICAS YQTQTNSHRR ARSVASQSII AYTMSLGAEN SVAYSNNSIA IPINFTISVT   720
TEILPVSMTK TSVDCTMYIC GDSTECSNLL LQYGSFCTQL NRALTGIAVE QDKNTQEVFA   780
QVKQIYKTPP IKDFGGFNFS QILPDPSKPS KRSFIEDLLF NKVTLADAGF IKQYGDCLGD   840
IAARDLICAQ KFNGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN QNAQALNTLV   960
KQLSSNFGAI SSVLNDILAR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTHNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC C           1251

SEQ ID NO: 51          moltype = DNA  length = 3819
FEATURE                Location/Qualifiers
misc_feature           1..3819
                       note = synthtic polynucleotide for
                       Antigen_1_nCov_Spike_full_opt_h.sapiens_koz_SA
source                 1..3819
                       mol_type = other

```
ggcttctctg ctctggaacc cctggtggat ctgcccatcg gcatcaacat cacccggttt    720
cagaccctgc acagaagcta cctgacacct ggcgatagca gcagcggatg gacagctggt    780
gccgccgctt actatgtggg ctacctgcag cctagaacct tcctgctgaa gtacaacgag    840
aacggcacca tcaccgacgc cgtggattgt gctctggatc ctctgagcga gacaaagtgc    900
accctgaagt ccttcaccgt ggaaaagggc atctaccaga ccagcaactt ccgggtgcag    960
cccaccgaat ccatcgtgcg gttccccaat atcaccaatc tgtgcccctt cggcgaggtg    1020
ttcaatgcca ccagattcgc ctctgtgtac gcctggaacc ggaagcggat cagcaattgc    1080
gtggccgact actccgtgct gtacaactcc gccagcttca gccttcaa gtgctacggc     1140
gtgtcccta ccaagctgaa cgacctgtgc ttcacaaacg tgtacgcga cagcttcgtg     1200
atccggggag atgaagtgcg gcagattgcc cctggacaga caggcaatat cgccgactac    1260
aactacaagc tgcccgacga cttcaccggc tgtgtgattg cctggaacag caacaacctg    1320
gactccaaag tcggcggcaa ctacaattac ctgtaccggc tgttccggaa gtccaatctg    1380
aagcccttcg agcgggacat ctccaccgag atctatcagg ccggcagcac cccttgtaac    1440
ggcgtgaaag gcttcaactg ctacttccca ctgcagtcct acggctttca gcccacatat    1500
ggcgtgggct atcagcccta cagagtggtg gtgctgagct tcgaactgct gcatgcccct    1560
gccacagtgt gcggccctaa gaaaagcacc aatctcgtga agaacaaatg cgtgaacttc    1620
aacttcaacg gcctgaccgg caccggcgtg ctgacagaga gcaacaagaa gttcctgcca    1680
ttccagcagt ttggccggga tatcgcagat accacagacc cgttagaca tccccagaca    1740
ctggaaatcc tggacatcac cccttgcagc ttcggcggag tgtctgtgat cacccctggc    1800
accaacacca gcaatcaggt ggcagtgctg taccagggcg tgaactgtac cgaagtgccc    1860
gtggccattc acgccgatca gctgacacct acatggcggg tgtactccac cggcagcaat    1920
gtgtttcaga ccagagccgg ctgtctgatc ggagccggaa acgtgaacaa tagctacgag    1980
tgcgacatcc ccatcggcgc tggcatctgt gccagctacc agacacagac aaacagcccc    2040
agacgggcca gatctgtggc cagccagagc atcattgcct acacaatgtc tctgggcgtc    2100
gagaacagcg tggcctactc caacaactct atcgctatcc ccaccaactt caccatcagc    2160
gtgaccacag agatcctgcc tgtgtccatg accaagacca gcgtggactg caccatgtac    2220
atctgcggcg attccaccga gtgctccaac ctgctgctgc agtacggcag cttctgcacc    2280
cagctgaata gagcccctga agggatcgcc gtgaacagg acaagaacac ccaagaggtg    2340
ttcgcccaag tgaagcagat ctacaagacc ctcctatca aggacttcgg cggcttcaat    2400
ttcagccaga ttctgcccga tcctagcaag cccagcaagc ggagcttcat cgaggacctg    2460
ctgttcaaca aagtgacact ggccgacgcc ggcttcatca gcagtatgg cgattgtctg    2520
ggcgacattg ccgccaggga tctgatttgc gcccagaagt taacggact gacagtgctg    2580
cctcctctgc tgaccgatga gatgatcgcc cagtacacat tgcccctgct ggccggcaca    2640
atcacaagcg gctggacatt tggagctggc gccgctctgc agatccccctt tgctatgcag    2700
atggcctacc ggttcaacgg catcggagtg acccagaatg tgctgtacga gaaccagaag    2760
ctgatcgcca accagttcaa cagcgccatc ggcaagatcc aggacagcct gagcagcaca    2820
gcaagcgccc tgggaaagct gcaggacgtg gtcaaccaga tgcccaggc actgaacacc    2880
ctggtcaagc agctgtcctc caacttcggc gccatcagct ctgtgctgaa cgatatcctg    2940
agcagactgg acaaggtgga agccgaggtg cagatcgaca gactgatcac cggaaggctg    3000
cagtccctgc agacctacgt tacccagcag ctgatcagag ccgccgagat tagagcctct    3060
gccaatctgg ccgccaccaa gatgtctgag tgtgtgctgg gccagagcaa gagagtggac    3120
ttttgcggca agggctacca cctgatgagc ttccctcagt ctgcccctca cggcgtggtg    3180
tttctgcacg tgacatacgt gcccgctcaa gagaagaatt tcaccaccgc tccagcactc    3240
tgccacgacg gcaaagccca cttttcctaga aaggcgtgt cgtgtccaa cggcacccat    3300
tggttcgtga cccagcggaa cttctacgag ccccagatca tcaccaccga caacaccttc    3360
gtgtctgcca actgcgacgt cgtgatcggc attgtgaaca taccgtgta cgaccctctg    3420
cagcccgaac tggacagctt caaagaggaa ctggacaagt actttaagaa ccacacaagc    3480
cccgacgtgg acctgggcga tatcagcgga atcaatgcca gcgtcgtgaa catccagaaa    3540
gagatcgacc ggctgaacga ggtggccaag aatctgaacg agagcctgat cgacctgcaa    3600
gaactgggga gtacgagca gtacatcaag tggcccgtgt acatctggct gggctttatc    3660
gccggactga ttgccatcgt gatggtcaca atcatgctgt gttgcatgac cagctgctgt    3720
agctgcctga aaggctgttg tagctgtggc agctgtctca agttcgacga ggacgattct    3780
gagcccgtgc tgaagggcgt gaaactgcac tacacctga                           3819
```

```
SEQ ID NO: 52          moltype = AA   length = 1270
FEATURE                Location/Qualifiers
REGION                 1..1270
                       note = Synthetic Construct
source                 1..1270
                       mol_type = protein
                       organism = synthetic construct
SEQUENCE: 52
MFVFLVLLPL VSSQCVNFTT RTQLPPAYTN SFTRGVYYPD KVFRSSVLHS TQDLFLPFFS    60
NVTWFHAIHV SGTNGTKRFA NPVLPFNDGV YFASTEKSNI IRGWIFGTTL DSKTQSLLIV    120
NNATNVVIKV CEFQFCNDPF LGVYYHKNNK SWMESEFRVY SSANNCTFEY VSQPFLMDLE    180
GKQGNFKNLR EFVFKNIDGY FKIYSKHTPI NLVRGLPQGF SALEPLVDLP IGINITRFQT    240
LHRSYLTPGD SSSGWTAGAA AYYVGYLQPR TFLLKYNENG TITDAVDCAL DPLSETKCTL    300
KSFTVEKGIY QTSNFRVQPT ESIVRFPNIT NLCPFGEVFN ATRFASVYAW NRKRISNCVA    360
DYSVLYNSAS FSTFKCYGVS PTKLNDLCFT NVYADSFVIR GDEVRQIAPG QTGNIADYNY    420
KLPDDFTGCV IAWNSNNLDS KVGGNYNYLY RLFRKSNLKP FERDISTEIY QAGSTPCNGV    480
KGFNCYFPLQ SYGFQPTYGV GYQPYRVVVL SFELLHAPAT VCGPKKSTNL VKNKCVNFNF    540
NGLTGTGVLT ESNKKFLPFQ QFGRDIADTT DAVRDPQTLE ILDITPCSFG GVSVITPGTN    600
TSNQVAVLYQ GVNCTEVPVA IHADQLTPTW RVYSTGSNVF QTRAGCLIGA EHVNNSYECD    660
IPIGAGICAS YQTQTNSPRR ARSVASQSII AYTMSLGVEN SVAYSNNSIA IPTNFTISVT    720
TEILPVSMTK TSVDCTMYIC GDSTECSNLL LQYGSFCTQL NRALTGIAVE QDKNTQEVFA    780
QVKQIYKTPP IKDFGGFNFS QILPDPSKPS KRSFIEDLLF NKVTLADAGF IKQYGDCLGD    840
IAARDLICAQ KFNGLTVLPP LLTDEMIAQY TSALLAGTIT SGWTFGAGAA LQIPFAMQMA    900
YRFNGIGVTQ NVLYENQKLI ANQFNSAIGK IQDSLSSTAS ALGKLQDVVN QNAQALNTLV    960
KQLSSNFGAI SSVLNDILSR LDKVEAEVQI DRLITGRLQS LQTYVTQQLI RAAEIRASAN    1020
```

-continued

```
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 53           moltype = DNA  length = 3762
FEATURE                 Location/Qualifiers
misc_feature            1..3762
                        note = synthetic polynucleotide for
                         Antigen_1_nCov_Spike_full_opt_h.sapiens_koz_SA_delta_Cter
source                  1..3762
                        mol_type = other DNA
                        organism = synthetic construct
CDS                     7..3762
SEQUENCE: 53
gccaccatgt tcgtgtttct ggtgctgctg cctctggtgt ccagccagtg tgtgaacttt  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgccaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaacgac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgcgcgagt tcgtgttcaa gaacatcgac  600
ggctacttca agatctacag caagcacacc cctatcaacc tcgtgcgggg tctgcctcag  660
ggcttctctg ctctggaacc cctggtggat ctgcccatcg gcatcaacat cacccggttt  720
cagaccctgc acagaagcta cctgacacct ggcgatagca gcagcggatg gacagctggt  780
gccgccgctt actatgtggg ctacctgcag cctagaacct tcctgctgaa gtacaacgag  840
aacggcacca tcaccgacgc cgtggattgt gctctggatc ctctgagcga gacaaagtgc  900
accctgaagt ccttcaccgt ggaaaagggc atctaccaga ccagcaactt ccgggtgcag  960
cccaccgaat ccatcgtgcg gttccccaat atcaccaatc tgtgcccctt cggcgaggtg  1020
ttcaatgcca ccagattcgc ctctgtgtac gcctggaacc ggaagcggat cagcaattgc  1080
gtggccgact actccgtgct gtacaactcc gccagcttca gcaccttcaa gtgctacggc  1140
gtgtccccta ccaagctgaa cgacctgtgc ttcacaaacg tgtacgccga cagcttcgtg  1200
atccggggag atgaagtgcg gcagattgcc cctggacaga caggcaatat cgccgactac  1260
aactacaagc tgcccgacga cttcaccggc tgtgtgattg cctggaacag caacaacctg  1320
gactccaaag tcggcggcaa ctacaattac ctgtaccggc tgttccggaa gtccaatctg  1380
aagcccttcg agcgggacat ctccaccgag atctatcagg ccggcagcac cccttgtaac  1440
ggcgtgaaag gcttcaactg ctacttccca ctgcagtcct acggctttca gcccacatat  1500
ggcgtgggct atcagcccta cagagtggtg gtgctgagct tcgaactgct gcatgcccct  1560
gccacagtgt gcggccctaa gaaaagcacc aatctcgtga agaacaaatg cgtgaacttc  1620
aacttcaacg gcctgaccgg caccggcgtg ctgacagaga gcaacaagaa gttcctgcca  1680
ttccagcagt ttggccggga tatcgccgat accacagacg ccgttagaga tccccagaca  1740
ctggaaatcc tggacatcac cccttgcagc ttcggcggag tgtctgtgat cacccctggc  1800
accaacacca gcaatcaggt ggcagtgctg taccagggcg tgaactgtac cgaagtgccc  1860
gtggccattc acgccgatca gctgacacct acatggcggg tgtactccac cggcagcaat  1920
gtgtttcaga ccagagccgg ctgtctgatc ggagccgagc acgtgaacaa tagctacgag  1980
tgcgacatcc ccatcggcgc tggcatctgt gccagctacc agacacagac aaacagcccc  2040
agacgggcca gatctgtggc cagccagagc atcattgcct acacaatgtc tctgggcgtc  2100
gagaacagcg tggcctactc caacaactct atcgctatcc ccaccaactt caccatcagc  2160
gtgaccacag agatcctgcc tgtgtccatg accaagacca gcgtggactg caccatgtac  2220
atctgcggcg attccaccga gtgctccaac ctgctgctgc agtacggcag cttctgcacc  2280
cagctgaata gagccctgac agggatcgcc gtggaacagg acaagaacac ccaagaggtg  2340
ttcgcccaag tgaagcagat ctacaagacc cctcctatca aggacttcgg cggcttcaat  2400
ttcagccaga ttctgcccga tcctagcaag cccagcaagc ggagcttcat cgaggacctg  2460
ctgttcaaca aagtgacact ggccgacgcc ggcttcatca agcagtatgg cgattgtctg  2520
ggcgacattg ccgccaggga tctgatttgc gcccagaagt ttaacggact gacagtgctg  2580
cctcctctgc tgaccgatga gatgatcgcc cagtacacat ctgccctgct ggccggcaca  2640
atcacaagcg gctggacatt tggagctggc gccgctctgc agatcccctt tgctatgcag  2700
atggcctacc ggttcaacgg catcggagtg acccagaatg tgctgtacga gaaccagaag  2760
ctgatcgcca accagttcaa cagcgccatc ggcaagatcc aggacagcct gagcagcaca  2820
gcaagcgccc tgggaaagct gcaggacgtg gtcaaccaga atgcccaggc actgaacacc  2880
ctggtcaagc agctgtcctc caacttcggc gccatcagct ctgtgctgaa cgatatcctg  2940
agcagactgg acaaggtgga agccgaggtg cagatcgaca gactgatcac cggaaggctg  3000
cagtccctgc agacctacgt tacccagcag ctgatcagag ccgccgagat tagagcctct  3060
gccaatctgg ccgccaccaa gatgtctgag tgtgtgctgg gccagagcaa gagagtggac  3120
ttttgcggca agggctacca cctgatgagc ttccctcagt ctgcccctca cggcgtggtg  3180
tttctgcacg tgacatacgt gcccgctcaa gagaagaatt tcaccaccgc tccagccatc  3240
tgccacgacg gcaaagccca ctttcctaga gaaggcgtgt tcgtgtccaa cggcacccat  3300
tggttcgtga cccagcggaa cttctacgag ccccagatca tcaccaccga caacaccttc  3360
gtgtctggca actgcgacgt cgtgatcggc attgtgaaca ataccgtgta cgaccctctg  3420
cagcccgagc tggacagctt caaagaggaa ctggataagt actttaagaa ccacacaagc  3480
cccgacgtgg acctgggcga tatcagcgga atcaatgcca gcgtcgtgaa catccagaaa  3540
gagatcgacc ggctgaacga ggtgaccaag aatctgaacg agagcctgat cgacctgcaa  3600
gaactgggga agtacgagca gtacatcaag tggccctggt acatctggct gggctttatc  3660
gccggactga ttgccatcgt gatggtcaca atcatgctgt gttgcatgac cagctgctgt  3720
agctgcctga agggctgttg tagctgtggc agctgctgct ga                    3762
```

-continued

```
SEQ ID NO: 54           moltype = AA  length = 1251
FEATURE                 Location/Qualifiers
REGION                  1..1251
                        note = Synthetic Construct
source                  1..1251
                        mol_type = protein
                        organism = synthetic construct
SEQUENCE: 54
MFVFLVLLPL VSSQCVNFTT RTQLPPAYTN SFTRGVYYPD KVFRSSVLHS TQDLFLPFFS  60
NVTWFHAIHV SGTNGTKRFA NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRGLPQGF SALEPLVDLP IGINITRFQT  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGNIADYNY  420
KLPDDFTGCV IAWNSNNLDS KVGGNYNYLY RLFRKSNLKP FERDISTEIY QAGSTPCNGV  480
KGFNCYFPLQ SYGFQPTYGV GYQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSPRR ARSVASQSII AYTMSLGVEN SVAYSNNSIA IPTNFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILSR LDKVEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC C           1251

SEQ ID NO: 55           moltype = DNA  length = 3819
FEATURE                 Location/Qualifiers
misc_feature            1..3819
                        note = synthetic polynucleotide for
                         Antigen_1_nCov_Spike_full_opt_h.sapiens_koz_SA_2P
source                  1..3819
                        mol_type = other DNA
                        organism = synthetic construct
CDS                     7..3819
SEQUENCE: 55
gccaccatgt tcgtgtttct ggtgctgctg cctctggtgt ccagccagtg tgtgaacttt  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgccaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaacgac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgcgcgagt tcgtgttcaa gaacatcgac  600
ggctacttca agatctacag caagcacacc cctatcaacc tcgtgcgggg tctgcctcag  660
ggcttctctg ctctggaacc cctggtggat ctgcccatcg gcatcaacat cacccggttt  720
cagaccctgc acagaagcta cctgacacct ggcgatagca gcagcggatg gacagctggt  780
gccgccgctt actatgtggg ctacctgcag cctagaacct tcctgctgaa gtacaacgag  840
aacggcacca tcaccgacgc cgtggattgt gctctggatc ctctgagcga gacaaagtgc  900
accctgaagt ccttcaccgt ggaaaagggc atctaccaga ccagcaactt ccgggtgcag  960
cccaccgaat ccatcgtgcg gttccccaat atcaccaatc tgtgcccctt cggcgaggtg  1020
ttcaatgcca ccagattcgc ctctgtgtac gcctggaacc ggaagcggat cagcaattgc  1080
gtggccgact actccgtgct gtacaactcc gccagcttca gcaccttcaa gtgctacggc  1140
gtgtccccta ccaagctgaa cgacctgtgc ttcacaaacg tgtacgccga cagcttcgtg  1200
atccggggag atgaagtgcg gcagattgcc cctggacaga caggcaatat cgccgactac  1260
aactacaagc tgcccgacga cttcaccggc tgtgtgattg cctggaacag caacaacctg  1320
gactccaaag tcggcggcaa ctacaattac ctgtaccggc tgttccggaa gtccaatctg  1380
aagcccttcg agcgggacat ctccaccgag atctatcagg ccggcagcac cccttgtaac  1440
ggcgtgaaag gcttcaactg ctacttccca ctgcagtcct acggctttca gcccacatat  1500
ggcgtgggct atcagcccta cagagtggtg gtgctgagct tcgaactgct gcatgcccct  1560
gccacagtgt gcggccctaa gaaaagcacc aatctcgtga agaacaaatg cgtgaacttc  1620
aacttcaacg gcctgaccgg caccggcgtg ctgacagaga gcaacaagaa gttcctgcca  1680
ttccagcagt ttggccggga tatcgccgat accacagacg ccgttagaga tccccagaca  1740
ctggaaatcc tggacatcac cccttgcagc ttcggcggag tgtctgtgat cacccctggc  1800
accaacacca gcaatcaggt ggcagtgctg taccagggcg tgaactgtac cgaagtgccc  1860
gtggccattc acgccgatca gctgacacct acatggcggg tgtactccac cggcagcaat  1920
gtgtttcaga ccagagccgg ctgtctgatc ggagccgagc acgtgaacaa tagctacgag  1980
tgcgacatcc ccatcggcgc tggcatctgt gccagctacc agacacagac aaacagcccc  2040
agacgggcca gatctgtggc cagccagagc atcattgcct acacaatgtc tctgggcgtc  2100
gagaacagcg tggcctactc caacaactct atcgctatcc ccaccaactt caccatcagc  2160
gtgaccacag agatcctgcc tgtgtccatg accaagacca gcgtggactg caccatgtac  2220
atctgcggcg attccaccga gtgctccaac ctgctgctgc agtacggcag cttctgcacc  2280
```

-continued

```
cagctgaata gagccctgac agggatcgcc gtggaacagg acaagaacac ccaagaggtg  2340
ttcgcccaag tgaagcagat ctacaagacc cctcctatca aggacttcgg cggcttcaat  2400
ttcagccaga ttctgcccga tcctagcaag cccagcaagc ggagcttcat cgaggacctg  2460
ctgttcaaca aagtgacact ggccgacgcc ggcttcatca agcagtatgg cgattgtctg  2520
ggcgacattg ccgccaggga tctgatttgc gcccagaagt ttaacggact gacagtgctg  2580
cctcctctgc tgaccgatga gatgatcgcc cagtacacat ctgccctgct ggccggcaca  2640
atcacaagcg gctggacatt tggagctggc gccgctctgc agatcccctt tgctatgcag  2700
atggcctacc ggttcaacgg catcggagtg acccagaatg tgctgtacga gaaccagaag  2760
ctgatcgcca accagttcaa cagcgccatc ggcaagatcc aggacagcct gagcagcaca  2820
gcaagcgccc tgggaaagct gcaggacgtg gtcaaccaga atgcccaggc actgaacacc  2880
ctggtcaagc agctgtcctc caacttcggc gccatcagct ctgtgctgaa cgatatcctg  2940
agcagactgg acccgccgga agccgaggtg cagatcgaca gactgatcac cggaaggctg  3000
cagtccctgc agacctacgt tacccagcag ctgatcagag ccgccgagat tagagcctct  3060
gccaatctgg ccgccaccaa gatgtctgag tgtgtgctgg gccagagcaa gagagtggac  3120
ttttgcggca agggctacca cctgatgagc ttccctcagt ctgcccctca cggcgtggtg  3180
tttctgcacg tgacatacgt gcccgctcaa gagaagaatt tcaccaccgc tccagccatc  3240
tgccacgacg gcaaagccca ctttcctaga gaaggcgtgt tcgtgtccaa cggcacccat  3300
tggttcgtga cccagcggaa cttctacgag ccccagatca tcaccaccga caacaccttc  3360
gtgtctggca actgcgacgt cgtgatcggc attgtgaaca ataccgtgta cgaccctctg  3420
cagcccgagc tggacagctt caaagaggaa ctggataagt actttaagaa ccacacaagc  3480
cccgacgtgg acctgggcga tatcagcgga atcaatgcca gcgtcgtgaa catccagaaa  3540
gagatcgacc ggctgaacga ggtggccaag aatctgaacg agagcctgat cgacctgcaa  3600
gaactgggga agtacgagca gtacatcaag tggccctggt acatctggct gggctttatc  3660
gccggactga ttgccatcgt gatggtcaca atcatgctgt gttgcatgac cagctgctgt  3720
agctgcctga agggctgttg tagctgtggc agctgctgca agttcgacga ggacgattct  3780
gagcccgtgc tgaagggcgt gaaactgcac tacacctga                         3819

SEQ ID NO: 56           moltype = AA  length = 1270
FEATURE                 Location/Qualifiers
REGION                  1..1270
                        note = Synthetic Construct
source                  1..1270
                        mol_type = protein
                        organism = synthetic construct
SEQUENCE: 56
MFVFLVLLPL VSSQCVNFTT RTQLPPAYTN SFTRGVYYPD KVFRSSVLHS TQDLFLPFFS  60
NVTWFHAIHV SGTNGTKRFA NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRGLPQGF SALEPLVDLP IGINITRFQT  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGNIADYNY  420
KLPDDFTGCV IAWNSNNLDS KVGGNYNYLY RLFRKSNLKP FERDISTEIY QAGSTPCNGV  480
KGFNCYFPLQ SYGFQPTYGV GYQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSPRR ARSVASQSII AYTMSLGVEN SVAYSNNSIA IPTNFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 57           moltype = DNA  length = 3762
FEATURE                 Location/Qualifiers
misc_feature            1..3762
                        note = synthetic polynucleotide for
                         Antigen_1_nCov_Spike_full_opt_h.sapiens_koz_SA_2P_delta_Cte
                         r
source                  1..3762
                        mol_type = other DNA
                        organism = synthetic construct
CDS                     7..3762
SEQUENCE: 57
gccaccatgt tcgtgtttct ggtgctgctg cctctggtgt ccagccagtg tgtgaacttt  60
accaccagaa cacagctgcc tccagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgccaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaacgac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgcgcgagt tcgtgttcaa gaacatcgac  600
```

```
ggctacttca agatctacag caagcacacc cctatcaacc tcgtgcgggg tctgcctcag    660
ggcttctctg ctctggaacc cctggtggat ctgcccatcg gcatcaacat cacccggttt    720
cagaccctgc acagaagcta cctgacacct ggcgatagca gcagcggatg gacaggtggt    780
gccgccgctt actatgtggg ctacctgcag cctagaacct tcctgctgaa gtacaacgag    840
aacggcacca tcaccgacgc cgtggattgt gctctggatc ctctgagcga gacaaagtgc    900
accctgaagt ccttcaccgt ggaaaagggc atctaccaga ccagcaactt ccgggtgcag    960
cccaccgaat ccatcgtgcg gttccccaat atcaccaatc tgtgccccct cggcgaggtg   1020
ttcaatgcca ccagattcgc ctctgtgtac gcctggaacc ggaagcggat cagcaattgc   1080
gtggccgact actccgtgct gtacaactcc gccagcttca gcacctttaa gtgctacggc   1140
gtgtccccta ccaagctgaa cgacctgtgc ttcacaaacg tgtacgccga cagcttcgtg   1200
atccggggag atgaagtgcg gcagattgcc cctggacaga caggcaatat cgccgactac   1260
aactacaagc tgcccgacga cttcaccggc tgtgtgattg cctggaacag caacaacctg   1320
gactccaaag tcggcggcaa ctacaattac ctgtaccggc tgttccggaa gtccaatctg   1380
aagcccttcg agcgggacat ctccaccgag atctatcagg ccggcagcac cccttgtaac   1440
ggcgtgaaag gcttcaactg ctacttccca ctgcagtcct acggctttca gcccacatat   1500
ggcgtgggct atcagcccta cagagtggtg gtgctgagct tcgaactgct gcatgcccct   1560
gccacagtgt gcggccctaa gaaaagcacc aatctcgtga gaaacaaatg cgtgaacttc   1620
aacttcaacg gcctgaccgg caccggcgtg ctgacagaga acaacaagaa gttcctgcca   1680
ttccagcagt ttggccggga tatcgccgat accacagacg ccgttagaga tccccagaca   1740
ctggaaatcc tggacatcac cccttgcagc ttcggcggag tgtctgtgat cacccctggc   1800
accaacacca gcaatcaggt ggcagtgctg taccagggcg tgaactgtac cgaagtgccc   1860
gtggccattc acgccgatca gctgacacct acatggcgcg tgtactccac cggcagcaat   1920
gtgtttcaga ccagagcggc tgtctgatc ggagccgagc acgtgaacaa tagctacgag   1980
tgcgacatcc ccatcggcgc tggcatctgt gccagctacc agacacagac aaacagcccc   2040
agacgggcca gatctgtggc cagccagagc atcattgcct acacaatgtc tctgggcgtc   2100
gagaacagcg tggcctactc caacaactct atcgctatcc ccaccaactt caccatcagc   2160
gtgaccacag agatcctgcc tgtgtccatg accaagacca gcgtggactg caccatgtac   2220
atctgcggcg attccaccga gtgctccaac ctgctgctgc agtacggcag cttctgcacc   2280
cagctgaata gagcctgac agggatcgcc gtggaacagg acaagaacac caagaggtg   2340
ttcgcccaag tgaagcagat ctacaagacc cctcctatca aggacttcgg cggcttcaat   2400
ttcagccaga tcctgcccga tcctagcaag cccagcaagc ggagcttcat cgaggacctg   2460
ctgttcaaca aagtgacact ggccgacgcc ggcttcatca gcagtatgg cgattgtctg   2520
ggcgacattg ccgccaggga tctgatttgc gcccagaagt taacggact gacagtgctg   2580
cctcctctgc tgaccgatga gatgatcgcc cagtacacat ctgccctgct ggccggcaca   2640
atcacaagcg gctggacatt tggagctggc gccgctctgc agatccctt tgctatgcag   2700
atggcctacc ggttcaacgg catcggagtg acccagaatg tgctgtacga aaaccagaag   2760
ctgatcgcca accagttcaa cagcgccatc ggcaagatcc aggacagcct gagcagcaca   2820
gcaagcgccc tgggaaagct gcaggacgtg gtcaaccaga tgcccaggc actgaacacc   2880
ctggtcaagc agctgtcctc caacttcggc gccatcagct ctgtgctgaa cgatatcctg   2940
agcagactgg acccgccgga agccgaggtg cagatcgaca gactgatcac cggaaggctg   3000
cagtccctgc agacctacgt tacccagcag ctgatcagac ccgccgagat tagagcctct   3060
gccaatctgg ccgccaccaa gatgtctgag tgtgtgctgg ccagagcaa gagagtggac   3120
ttcggggca agggctacca cctgatgagc ttccctcagt ctgccccctca cggcgtggtg   3180
tttctgcacg tgacatacgt gcccgctcaa gagaagaatt tcaccaccgc tccagccatc   3240
tgccacgacg gcaaagccca cttcctaga aaggcgtgt tcgtgccaa cggcacccat   3300
tggttcgtga cccagcggaa cttctacgag ccccagatca tcaccaccga caacaccttc   3360
gtgtctggca actgcgacgt cgtgatcggc attgtgaaca ataccgtgta cgaccctctg   3420
cagcccgagc tggacagctt caaagaggaa ctgataagt actttaagaa ccacacaagc   3480
cccgacgtgg acctgggcga tatcagcgga atcaatgcca gcgtcgtgaa catccagaaa   3540
gagatcgacc ggctgaacga ggtggccaag aatctgaacg agagcctgat cgacctgcaa   3600
gaactgggga gtacagca gtacatcaag tggccctggt acatctggct gggctttatc   3660
gccggactga ttgccatcgt gatggtcaca atcatgctgt gttgcatgac cagctgctgt   3720
agctgcctga agggctgttg tagctgtggc agctgctgct ga                      3762
SEQ ID NO: 58           moltype = AA   length = 1251
FEATURE                 Location/Qualifiers
REGION                  1..1251
                        note = Synthetic Construct
source                  1..1251
                        mol_type = protein
                        organism = synthetic construct
SEQUENCE: 58
MFVFLVLLPL VSSQCVNFTT RTQLPPAYTN SFTRGVYYPD KVFRSSVLHS TQDLFLPFFS    60
NVTWFHAIHV SGTNGTKRFA NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRGLPQGF SALEPLVDLP IGINITRFQT   240
LHRSYLTPGD SSSGWTAGAA AYYVGYLQPR TFLLKYNENG TITDAVDCAL DPLSETKCTL   300
KSFTVEKGIY QTSNFRVQPT ESIVRFPNIT NLCPFGEVFN ATRFASVYAW NRKRISNCVA   360
DYSVLYNSAS FSTFKCYGVS PTKLNDLCFT NVYADSFVIR GDEVRQIAPG QTGNIADYNY   420
KLPDDFTGCV IAWNSNNLDS KVGGNYNYLY RLFRKSNLKP FERDISTEIY QAGSTPCNGV   480
KGFNCYFPLQ SYGFQPTYGV GYQPYRVVVL SFELLHAPAT VCGPKKSTNL VKNKCVNFNF   540
NGLTGTGVLT ESNKKFLPFQ QFGRDIADTT DAVRDPQTLE ILDITPCSFG GVSVITPGTN   600
TSNQVAVLYQ GVNCTEVPVA IHADQLTPTW RVYSTGSNVF QTRAGCLIGA EHVNNSYECD   660
IPIGAGICAS YQTQTNSPRR ARSVASQSII AYTMSLGVEN SVAYSNNSIA IPTNFTISVT   720
TEILPVSMTK TSVDCTMYIC GDSTECSNLL LQYGSFCTQL NRALTGIAVE QDKNTQEVFA   780
QVKQIYKTPP IKDFGGFNFS QILPDPSKPS KRSFIEDLLF NKVTLADAGF IKQYGDCLGD   840
IAARDLICAQ KFNGLTVLPP LLTDEMIAQY TSALLAGTIT SGWTFGAGAA LQIPFAMQMA   900
YRFNGIGVTQ NVLYENQKLI ANQFNSAIGK IQDSLSSTAS ALGKLQDVVN QNAQALNTLV   960
KQLSSNFGAI SSVLNDILSR LDPPEAEVQI DRLITGRLQS LQTYVTQQLI RAAEIRASAN  1020
```

-continued

```
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC C           1251

SEQ ID NO: 59          moltype = DNA  length = 3828
FEATURE                Location/Qualifiers
misc_feature           1..3828
                       note = synthetic polynucleotide for
                        Antigen_1_nCov_Spike_full_opt_h.sapiens_koz_Br
source                 1..3828
                       mol_type = other DNA
                       organism = synthetic construct
CDS                    7..3828
SEQUENCE: 59
gccaccatgt tcgtgtttct ggtgctgctg cctctggtgt ccagccagtg tgtgaacttt  60
accaacagaa cacagctgcc ttcagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgacaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaactac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgagtgagt tcgtgttcaa gaacatcgac  600
ggctacttca agatctacag caagcacacc cctatcaacc tcgtgcggga tctgcctcag  660
ggcttctctg ctctggaacc cctggtggat ctgcccatcg gcatcaacat cacccggttt  720
cagacactgc tggccctgca cagaagctac ctgacacctg gcgatagcag cagcggatgg  780
acagctggtg ccgccgctta ctatgtgggc tacctgcagc ctagaacctt cctgctgaag  840
tacaacgaga acggcaccat caccgacgcc gtggattgtg ctctggatcc tctgagcgag  900
acaaagtgca ccctgaagtc cttcaccgtg gaaaagggca tctaccagac cagcaacttc  960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtccctac caagctgaac gacctgtgct tcacaaacgt gtacgccgac  1200
agcttcgtga tccggggaga tgaagtgcgg cagattgccc ctggacagac aggcacgatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga agcccttcga gcgggacatc tccaccgaga tctatcaggc cggcagcacc  1440
ccttgtaacg gcgtgaaagg cttcaactgc tacttcccac tgcagtccta cggctttcag  1500
cccacatatg gcgtgggcta tcagccctac agagtggtgg tgctgagctt cgaactgctg  1560
catgccccctg ccacagtgtg cggccctaag aaaagcacca atctcgtgaa gaacaaatgc  1620
gtgaacttca acttcaacgg cctgaccggc accggcgtgc tgacagagag caacaagaag  1680
ttcctgccat tccagcagtt tggccgggat atcgccgata ccacagacgc cgttagagat  1740
ccccagacac tggaaatcct ggacatcacc ccttgcagct tcggcggagt gtctgtgatc  1800
acccctggca ccaacaccag caatcaggtg gcagtgctgt accagggcgt gaactgtacc  1860
gaagtgcccg tggccattca cgccgatcag ctgacaccta catggcgggt gtactccacc  1920
ggcagcaatg tgtttcagac cagagccggc tgtctgatcg gagccgagta cgtgaacaat  1980
agctacgagt gcgacatccc catcggcgct ggcatctgtg ccagctacca gacacagaca  2040
aacagcccca gacgggccag atctgtggcc agccagagca tcattgccta cacaatgtct  2100
ctgggcgccg agaacagcgt ggcctactcc aacaactcta tcgctatccc caccaacttc  2160
accatcagcg tgaccacaga gatcctgcct gtgtccatga ccaagaccag cgtggactgc  2220
accatgtaca tctgcggcga ttccaccgag tgctccaacc tgctgctgca gtacggcagc  2280
ttctgcaccc agctgaatag agccctgaca gggatcgccg tggaacagga caagaacacc  2340
caagaggtgt tcgcccaagt gaagcagatc tacaagaccc ctcctatcaa ggacttcggc  2400
ggcttcaatt tcagccagat tctgcccgat cctagcaagc ccagcaagcg gagcttcatc  2460
gaggacctgc tgttcaacaa agtgacactg gccgacgccg gcttcatcaa gcagtatggc  2520
gattgtctgg gcgacattgc cgccagggat ctgatttgcg cccagaagtt taacggactg  2580
acagtgctgc ctcctctgct gaccgatgag atgatcgccc agtacacatc tgccctgctg  2640
gccggcacaa tcacaagcgg ctggacattt ggagctggcg ccgctctgca gatccccttt  2700
gctatgcaga tggcctaccg gttcaacggc atcggagtga cccagaatgt gctgtacgag  2760
aaccagaagc tgatcgccaa ccagttcaac agcgccatcg gcaagatcca ggacagcctg  2820
agcagcacag caagcgccct gggaaagctg caggacgtgg tcaaccagaa tgcccaggca  2880
ctgaacaccc tggtcaagca gctgtcctcc aacttcggcg ccatcagctc tgtgctgaac  2940
gatatcctga gcagactgga caaggtggaa gccgaggtgc agatcgacag actgatcacc  3000
ggaaggctgc agtccctgca gacctacgtt acccagcagc tgatcagagc cgccgagatt  3060
agagcctctg ccaatctggc cgccatcaag atgtctgagt gtgtgctggg ccagagcaag  3120
agagtggact tttgcggcaa gggctaccac ctgatgagct tccctcagtc tgcccctcac  3180
ggcgtggtgt ttctgcacgt gacatacgtg cccgctcaag agaagaattt caccaccgct  3240
ccagccatct gccacgacgg caaagcccac tttcctagag aaggcgtgtt cgtgtccaac  3300
ggcacccatt ggttcgtgac ccagcggaac ttctacgagc cccagatcat caccaccgac  3360
aacaccttcg tgtctggcaa ctgcgacgtc gtgatcggca ttgtgaacaa taccgtgtac  3420
gaccctctgc agcccgagct ggacagcttc aaagaggaac tggataagta ctttaagaac  3480
cacacaagcc ccgacgtgga cctgggcgat atcagcggaa tcaatgccag cttcgtgaac  3540
atccagaaag agatcgaccg gctgaacgag gtggccaaga atctgaacga gagcctgatc  3600
gacctgcaag aactggggaa gtacgagcag tacatcaagt ggccctggta catctggctg  3660
ggctttatcg ccggactgat tgccatcgtg atggtcacaa tcatgctgtg ttgcatgacc  3720
agctgctgta gctgcctgaa gggctgttgt agctgtggca gctgctgcaa gttcgacgag  3780
gacgattctg agcccgtgct gaagggcgtg aaactgcact acacctga            3828
```

```
SEQ ID NO: 60          moltype = AA  length = 1273
FEATURE                Location/Qualifiers
REGION                 1..1273
                       note = Synthetic Construct
source                 1..1273
                       mol_type = protein
                       organism = synthetic construct
SEQUENCE: 60
MFVFLVLLPL VSSQCVNFTN RTQLPSAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNYPF LGVYYHKNNK SWMESEFRVY SSANNCTFEY VSQPFLMDLE  180
GKQGNFKNLS EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGTIAD  420
YNYKLPDDFT GCVIAWNSNN LDSKVGGNYN YLYRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEYVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAAIKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASFVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 61          moltype = DNA  length = 3771
FEATURE                Location/Qualifiers
misc_feature           1..3771
                       note = synthetic polynucleotide for
                        Antigen_1_nCov_Spike_full_opt_h.sapiens_koz_Br_delta_Cter
source                 1..3771
                       mol_type = other DNA
                       organism = synthetic construct
CDS                    7..3771
SEQUENCE: 61
gccaccatgt tcgtgtttct ggtgctgctg cctctggtgt ccagccagtg tgtgaacttt  60
accaacagaa cacagctgcc ttcagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgacaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaactac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgagtgagt tcgtgttcaa gaacatcgac  600
ggctacttca agatctacag caagcacacc cctatcaacc tcgtgcggga tctgcctcag  660
ggcttctctg ctctggaacc cctggtggat ctgcccatcg gcatcaacat cacccggttt  720
cagacactgc tggccctgca cagaagctac ctgacacctg gcgatagcag cagcggatgg  780
acagctggtg ccgccgctta ctatgtgggc tacctgcagc ctagaacctt cctgctgaag  840
tacaacgaga acggcaccat caccgacgcc gtggattgtg ctctggatcc tctgagcgag  900
acaaagtgca ccctgaagtc cttcaccgtg gaaaagggca tctaccagac cagcaacttc  960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtcccctac caagctgaac gacctgtgct tcacaaacgt gtacgccgac  1200
agcttcgtga tccggggaga tgaagtgcgg cagattgccc ctggacagac aggcacgatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga agcccttcga gcgggacatc tccaccgaga tctatcaggc cggcagcacc  1440
ccttgtaacg gcgtgaaagg cttcaactgc tacttcccac tgcagtccta cggctttcag  1500
cccacatatg gcgtgggcta tcagccctac agagtggtgg tgctgagctt cgaactgctg  1560
catgcccctg ccacagtgtg cggccctaag aaaagcacca atctcgtgaa gaacaaatgc  1620
gtgaacttca acttcaacgg cctgaccggc accggcgtgc tgacagagag caacaagaag  1680
ttcctgccat tccagcagtt tggccgggat atcgccgata ccacagacgc cgttagagat  1740
ccccagacac tggaaatcct ggacatcacc ccttgcagct tcggcggagt gtctgtgatc  1800
acccctggca ccaacaccag caatcaggtg gcagtgctgt accagggcgt gaactgtacc  1860
gaagtgcccg tggccattca cgccgatcag ctgacaccta catggcgggt gtactccacc  1920
ggcagcaatg tgtttcagac cagagccggc tgtctgatcg gagccgagta cgtgaacaat  1980
agctacgagt gcgacatccc catcggcgct ggcatctgtg ccagctacca gacacagaca  2040
aacagcccca gacgggccag atctgtggcc agccagagca tcattgccta cacaatgtct  2100
ctgggcgccg agaacagcgt ggcctactcc aacaactcta tcgctatccc caccaacttc  2160
accatcagcg tgaccacaga gatcctgcct gtgtccatga ccaagaccag cgtggactgc  2220
```

-continued

```
accatgtaca tctgcggcga ttccaccgag tgctccaacc tgctgctgca gtacggcagc  2280
ttctgcaccc agctgaatag agccctgaca gggatcgccg tggaacagga caagaacacc  2340
caagaggtgt tcgcccaagt gaagcagatc tacaagaccc tcctcatcaa ggacttcggc  2400
ggcttcaatt tcagccagat tctgcccgat cctagcaagc cagcaagcg gagcttcatc  2460
gaggacctgc tgttcaacaa agtgacactg gccgacgccg gcttcatcaa gcagtatggc  2520
gattgtctgg gcgacattgc cgccagggat ctgatttgcg cccagaagtt taacggactg  2580
acagtgctgc ctcctctgct gaccgatgag atgatcgccc agtacacatc tgccctgctg  2640
gccggcacaa tcacaagcgg ctggacattt ggagctggcg ccgctctgca gatccccttt  2700
gctatgcaga tggcctaccg gttcaacggc atcggagtga cccagaatgt gctgtacgag  2760
aaccagaagc tgatcgccaa ccagttcaac agcgccatcg gcaagatcca ggacagcctg  2820
agcagcacag caagcgccct gggaaagctg caggacgtgg tcaaccagaa tgcccaggca  2880
ctgaacaccc tggtcaagca gctgtcctcc aacttcggcg ccatcagctc tgtgctgaac  2940
gatatcctga gcagactgga caaggtggaa gccgaggtgc agatcgacag actgatcacc  3000
ggaaggctgc agtccctgca gacctacgtt acccagcagc tgatcagcgc cgccgagatt  3060
agagcctctg ccaatctggc cgccatcaag atgtctgagt gtgtgctggg ccagagcaag  3120
agagtggact tttgcggcaa gggctaccac ctgatgagct tccctcagtc tgcccctcac  3180
ggcgtggtgt tctgcacgt gacatacgtg cccgctcaag agaagaattt caccaccgct  3240
ccagccatct gccacgacgg caaagcccac tttcctagca aggcgtgtt cgtgtccaac  3300
ggcacccatt ggttcgtgac ccagcggaac ttctacgagc cccagatcat caccaccgac  3360
aacacctcg tgtctggcaa ctgcgacgtc gtgatcggca ttgtgaacaa taccgtgtac  3420
gaccctctgc agcccgagct ggacagcttc aagaggaac tggataagta ctttaagaac  3480
cacacaagcc ccgacgtgga cctgggcgat atcagcgaca tcaatgccag cttcgtgaac  3540
atccagaaag atcgaccg gctgaacgag gtgccaaga atctgaacga gagcctgatc  3600
gacctgcaag aactggggaa gtacgagcag tacatcaagt ggccctgta catctggctg  3660
ggctttatcg ccggactgat tgccatcgtg atggtcacaa tcatgctgtg ttgcatgacc  3720
agctgctgta gctgcctgaa gggctgttgt agctgtggca gctgctgctg a  3771
```

| | | |
|---|---|---|
| SEQ ID NO: 62 | moltype = AA length = 1254 | |
| FEATURE | Location/Qualifiers | |
| REGION | 1..1254 | |
| | note = Synthetic Construct | |
| source | 1..1254 | |
| | mol_type = protein | |
| | organism = synthetic construct | |

SEQUENCE: 62

```
MFVFLVLLPL VSSQCVNFTN RTQLPSAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNYPF LGVYYHKNNK SWMESEFRVY SSANNCTFEY VSQPFLMDLE  180
GKQGNFKNLS EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGTIAD  420
YNYKLPDDFT GCVIAWNSNN LDSKVGGNYN YLYRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEYVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAAIKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASFVNIQ KEIDRLNEVA KNLNESLIDL 1200
QELGKYEQYI KWPWYIWLGF IAGLIAIVMV TIMLCCMTSC CSCLKGCCSC GSCC         1254
```

| | | |
|---|---|---|
| SEQ ID NO: 63 | moltype = DNA length = 3828 | |
| FEATURE | Location/Qualifiers | |
| misc_feature | 1..3828 | |
| | note = synthetic polynucleotide for | |
| | Antigen_1_nCov_Spike_full_opt_h.sapiens_koz_Br_2P | |
| source | 1..3828 | |
| | mol_type = other DNA | |
| | organism = synthetic construct | |
| CDS | 7..3828 | |

SEQUENCE: 63

```
gccaccatgt tcgtgtttct ggtgctgctg cctctggtgt ccagccagtg tgtgaacttt   60
accaacagaa cacagctgcc ttcagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc acgtgtccg gcaccaatgg caccaagaga  240
ttcgacaacc ccgtgctgcc cttcaacgac ggggtgtact ttgccagcac cgagaagtcc  300
aacatcatca gaggctggat cttcggcacc acactgaca gcaagaccca gagcctgctg  360
atcgtgaaca acgccacaa cgtgtgcatc aagtgtgac agttccagtt ctgcaactac  420
cccttcctgg gcgtctacta ccacaagaac aacaagagct ggatggaaag cgagttccga  480
gtgtacagca gcgccaacaa ctgcaccttc gagtacgtgt cccagccttt cctgatggac  540
ctggaaggca gcagggcaa cttcaagaac ctgagtgagt tcgtgttcaa gaacatcgac  600
ggctactca gatctacag caagcacacc cctatcaacc tcgtgcggga tctgcctcag  660
ggcttctctg ctctggaacc cctggtggat ctgcccatcg gcatcaacat cacccggttt  720
```

```
cagacactgc tggccctgca cagaagctac ctgacacctg gcgatagcag cagcggatgg   780
acagctggtg ccgccgctta ctatgtgggc tacctgcagc ctagaacctt cctgctgaag   840
tacaacgaga acggcaccat caccgacgcc gtggattgtg ctctggatcc tctgagcgag   900
acaaagtgca ccctgaagtc cttcaccgtg aaaagggca tctaccagac cagcaacttc   960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtcccctac caagctgaac gacctgtgct tcacaaacgt gtacgccgac  1200
agcttcgtga tccggggaga tgaagtgcgg cagatgcccc tggacagac aggcacgatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga gcccttcga gcgggacatc tccaccgaga tctatcaggc cggcagcacc  1440
ccttgtaacg gcgtgaaagg cttcaactgc tacttccac tgcagtccta cggctttcag  1500
cccacatatg gcgtgggcta tcagcctac agagtggtgg tgctgagctt cgaactgctg  1560
catgcccctg ccacagtgtg cggccctaag aaaagcacca atctcgtgaa gaacaaatgc  1620
gtgaacttca acttcaacgg cctgaccggc accggcgtgc tgacagagag caacaagaag  1680
ttcctgccat tccagcagtt tggccgggat atcgccgata ccagacgc cgttagagat  1740
ccccagacac tggaaatcct ggacatcacc ccttgctcgg cggctgtg tgtctgtaca  1800
acccctggca ccaacaccag caatcaggtg gcagtgctgt accagggcgt gaactgtacc  1860
gaagtgcccg tggccattca cgccgatcag ctgacaccta catggcgggt gtactccacc  1920
ggcagcaatg tgtttcagac cagagccggc tgtctgatcg gagccgagta cgtgaacaat  1980
agctacgagt gcgacatccc catcggcgct ggcatctgtg ccagctacca gacacagaca  2040
aacagcccca gacgggccag atctgtggcc agcagagca tcattgccta cacaatgtct  2100
ctgggcgccg agaacagcgt ggcctactcc aacaactcta tcgctatccc caccaacttc  2160
accatcagcg tgaccacaga gatcctgcct gtgtccatga ccaagaccag cgtggactgc  2220
accatgtaca tctcgggcga ttccaccgag tgctccaacc tgctgctgca gtacggcagc  2280
ttctgcaccc agctgaatag agccctgaca gggatcgccg tggaacagga caagaacacc  2340
caagaggtgt tcgcccaagt gaagcagatc tacaagaccc ctccatcaa ggacttcggc  2400
ggcttcaatt tcagccagat tctgcccgat cctagcaagc cagcaagcg agcttcatc  2460
gaggacctgc tgttcaacaa agtgacactg gccgacgccg gcttcatcaa gcagtatggc  2520
gattgtctgg gcgacattgc cgccagggat ctgatttgcg cccagaagtt taacggactg  2580
acagtgctgc ctcctctgct gaccgatgag atgatcgccc agtacacatc tgccctgctg  2640
gccggcacaa tcacaagcgg ctggacattt ggagctggcg ccgctctgca gatccccttt  2700
gctatgcaga tggcctaccg gttcaacggc atcggagtga cccagaatgt gctgtacgag  2760
aaccagaagc tgatcgccaa ccagttcaac agcgccatcg gcaagatcca ggacagcctg  2820
agcagcacag caagcgccct gggaaagctg caggacgtgg tcaaccagaa tgcccaggca  2880
ctgaacaccc tggtcaagca gctgtcctcc aacttcggcg ccatcagctc tgtgctgaac  2940
gatatcctga gcagactgga cccgccggaa gccgaggtgc agatcgacag actgatcacc  3000
ggaaggctgc agtccctgca gacctacgtt acccagcagc tgatcagagc cgccgagattt  3060
agagcctctg ccaatctggc cgccatcaag atgtctgagt gtgtgctggg ccagagcaag  3120
agagtggact tttgcggcaa gggctaccac ctgatgagct tccctcagtc tgcccctcac  3180
ggcgtggtgt ttctgcacgt gacatacgtg cccgctcaag agaagaattt caccaccgct  3240
ccagccatct gccacgacgg caaagcccac tttcctagag aaggcgtgtt cgtgtccaac  3300
ggcacccatt ggttcgtgac ccagcggaac ttctacgagc cccagatcat caccaccgac  3360
aacaccttcg tgtctggcaa ctgcgacgtc gtgatcggca ttgtgaacaa taccgtgtac  3420
gaccctctga gcccgagct ggacagcttc aaagaggaac tggataagta ctttaagaac  3480
cacacaagcc ccgacgtgga cctgggcgat atcagcggaa tcaatgccag cgttgtgaac  3540
atccagaaag agatcgaccg gctgaacgag gtggccaaga atctgaacga gagcctgatc  3600
gacctgcaag aactggggaa gtacgagcag tacatcaagt ggccctggta catctggctg  3660
ggctttatcg ccggactgat tgccatcgtg atggtcacaa tcatgctgtg ttgcatgacc  3720
agctgctgta gctgcctgaa gggctgttgt agctgtggca gctgctgcaa gttcgacgag  3780
gacgattctg agcccgtgct gaagggcgtg aaactgcact acacctga             3828

SEQ ID NO: 64          moltype = AA  length = 1273
FEATURE                Location/Qualifiers
REGION                 1..1273
                       note = Synthetic Construct
source                 1..1273
                       mol_type = protein
                       organism = synthetic construct
SEQUENCE: 64
MFVFLVLLPL VSSQCVNFTN RTQLPSAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNYPF LGVYYHKNNK SWMESEFRVY SSANNCTFEY VSQPFLMDLE   180
GKQGNFKNLS EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGTIAD   420
YNYKLPDDFT GCVIAWNSNN LDSKVGGNYN YLYRLFRKSN LKPFERDIST EIYQAGSTPC   480
NGVKGFNCYF PLQSYGFQPT YGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQGVNCTEV PVAIHADQLT PTWRVYSTGS NVFQTRAGCL IGAEYVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDPPEAE VQIDRLITGR LQSLQTYVTQ QLIRAAEIRA  1020
SANLAAIKMS ECVLGQSKRV DFCGKGYHLM SFPQSAPHGV VFLHVTYVPA QEKNFTTAPA  1080
```

-continued

```
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASFVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 65           moltype = DNA  length = 3771
FEATURE                 Location/Qualifiers
misc_feature            1..3771
                        note = synthetic polynucleotide for
                         Antigen_1_nCov_Spike_full_opt_h.sapiens_koz_Br_2P_delta_Cte
                         r
source                  1..3771
                        mol_type = other DNA
                        organism = synthetic construct
CDS                     7..3771
SEQUENCE: 65
gccaccatgt tcgtgtttct ggtgctgctg cctctggtgt ccagccagtg tgtgaacttt  60
accaacagaa cacagctgcc ttcagcctac accaacagct ttaccagagg cgtgtactac  120
cccgacaagg tgttcagatc cagcgtgctg cactctaccc aggacctgtt cctgcctttc  180
ttcagcaacg tgacctggtt ccacgccatc cacgtgtccg gcaccaatgg caccaagaga  240
ttcgacaacc ccgtgctgcc cttcaacgac ggggtgtact ttgccagcac cgagaagtcc  300
aacatcatca gaggctggat cttcggcacc acactggaca gcaagaccca gagcctgctg  360
atcgtgaaca acgccaccaa cgtggtcatc aaagtgtgcg agttccagtt ctgcaactac  420
cccttcctgg gcgtctacta ccacaagaac aacaagagct ggatggaaag cgagttccgg  480
gtgtacagca gcgccaacaa ctgcaccttc gagtacgtgt cccagccttt cctgatggac  540
ctggaaggca agcagggcaa cttcaagaac ctgagtgagt tcgtgttcaa gaacatcgac  600
ggctacttca agatctacag caagcacacc cctatcaacc tcgtgcggga tctgcctcag  660
ggcttctctg ctctggaacc cctggtggat ctgcccatcg gcatcaacat cacccggttt  720
cagacactgc tggccctgca cagaagctac ctgacacctg gcgatagcag cagcggatgg  780
acagctggtg ccgccgctta ctatgtgggc tacctgcagc ctagaacctt cctgctgaag  840
tacaacgaga acggcaccat caccgacgcc gtggattgtg ctctggatcc tctgagcgag  900
acaaagtgca ccctgaagtc cttcaccgtg gaaaagggca tctaccagac cagcaacttc  960
cgggtgcagc ccaccgaatc catcgtgcgg ttccccaata tcaccaatct gtgccccttc  1020
ggcgaggtgt tcaatgccac cagattcgcc tctgtgtacg cctggaaccg gaagcggatc  1080
agcaattgcg tggccgacta ctccgtgctg tacaactccg ccagcttcag caccttcaag  1140
tgctacggcg tgtcccctac caagctgaac gacctgtgct tcacaaacgt gtacgccgac  1200
agcttcgtga tccggggaga tgaagtgcgg cagattgccc ctggacagac aggcacgatc  1260
gccgactaca actacaagct gcccgacgac ttcaccggct gtgtgattgc ctggaacagc  1320
aacaacctgg actccaaagt cggcggcaac tacaattacc tgtaccggct gttccggaag  1380
tccaatctga agcccttcga gcgggacatc tccaccgaga tctatcaggc cggcagcacc  1440
ccttgtaacg gcgtgaaagg cttcaactgc tacttcccac tgcagtccta cggctttcag  1500
cccacatatg gcgtgggcta tcagccctac agagtggtgg tgctgagctt cgaactgctg  1560
catgcccctg ccacagtgtg cggccctaag aaaagcacca atctcgtgaa gaacaaatgc  1620
gtgaacttca acttcaacgg cctgaccggc accggcgtgc tgacagagag caacaagaag  1680
ttcctgccat tccagcagtt tggccgggat atcgccgata ccacagacgc cgttagagat  1740
ccccagacac tggaaatcct ggacatcacc ccttgcagct tcggcggagt gtctgtgatc  1800
accccctggca ccaacaccag caatcaggtg gcagtgctgt accagggcgt gaactgtacc  1860
gaagtgcccg tggccattca cgccgatcag ctgacaccta catggcgggt gtactccacc  1920
ggcagcaatg tgtttcagac cagagccggc tgtctgatcg gagccgagta cgtgaacaat  1980
agctacgagt gcgacatccc catcggcgct ggcatctgtg ccagctacca gacacagaca  2040
aacagcccca gacgggccag atctgtggcc agccagagca tcattgccta cacaatgtct  2100
ctgggcgccg agaacagcgt ggcctactcc aacaactcta tcgctatccc caccaacttc  2160
accatcagcg tgaccacaga gatcctgcct gtgtccatga ccaagaccag cgtggactgc  2220
accatgtaca tctgcggcga ttccaccgag tgctccaacc tgctgctgca gtacggcagc  2280
ttctgcaccc agctgaatag agccctgaca gggatcgccg tggaacagga caagaacacc  2340
caagaggtgt tcgcccaagt gaagcagatc tacaagaccc ctcctatcaa ggacttcggc  2400
ggcttcaatt tcagccagat tctgcccgat cctagcaagc ccagcaagcg gagcttcatc  2460
gaggacctgc tgttcaacaa agtgacactg gccgacgccg gcttcatcaa gcagtatggc  2520
gattgtctgg gcgacattgc cgccagggat ctgatttgcg cccagaagtt taacggactg  2580
acagtgctgc ctcctctgct gaccgatgag atgatcgccc agtacacatc tgccctgctg  2640
gccggcacaa tcacaagcgg ctggacattt ggagctggcg ccgctctgca gatccccttt  2700
gctatgcaga tggcctaccg gttcaacggc atcggagtga cccagaatgt gctgtacgag  2760
aaccagaagc tgatcgccaa ccagttcaac agcgccatcg gcaagatcca ggacagcctg  2820
agcagcacag caagcgccct gggaaagctg caggacgtgg tcaaccagaa tgcccaggca  2880
ctgaacaccc tggtcaagca gctgtcctcc aacttcggcg ccatcagctc tgtgctgaac  2940
gatatcctga gcagactgga cccgccggaa gccgaggtgc agatcgacag actgatcacc  3000
ggaaggctgc agtccctgca gacctacgtt acccagcagc tgatcagagc cgccgagatt  3060
agagcctctg ccaatctggc cgccatcaag atgtctgagt gtgtgctggg ccagagcaag  3120
agagtggact tttgcggcaa gggctaccac ctgatgagct tccctcagtc tgcccctcac  3180
ggcgtggtgt ttctgcacgt gacatacgtg cccgctcaag agaagaattt caccaccgct  3240
ccagccatct gccacgacgg caaagcccac tttcctagag aaggcgtgtt cgtgtccaac  3300
ggcacccatt ggttcgtgac ccagcggaac ttctacgagc cccagatcat caccaccgac  3360
aacaccttcg tgtctggcaa ctgcgacgtc gtgatcggca ttgtgaacaa taccgtgtac  3420
gaccctctgc agcccgagct ggacagcttc aaagaggaac tggataagta ctttaagaac  3480
cacacaagcc ccgacgtgga cctgggcgat atcagcggaa tcaatgccag cttcgtgaac  3540
atccagaaag agatcgaccg gctgaacgag gtggccaaga atctgaacga gagcctgatc  3600
gacctgcaag aactggggaa gtacgagcag tacatcaagt ggccctggta catctggctg  3660
ggctttatcg ccggactgat tgccatcgtg atggtcacaa tcatgctgtg ttgcatgacc  3720
agctgctgta gctgcctgaa gggctgttgt agctgtggca gctgctgctg a           3771
```

```
SEQ ID NO: 66          moltype = AA  length = 1254
FEATURE                Location/Qualifiers
REGION                 1..1254
                       note = Synthetic Construct
source                 1..1254
                       mol_type = protein
                       organism = synthetic construct
SEQUENCE: 66
MFVFLVLLPL VSSQCVNFTN RTQLPSAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNYPF LGVYYHKNNK SWMESEFRVY SSANNCTFEY VSQPFLMDLE  180
GKQGNFKNLS EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGTIAD  420
YNYKLPDDFT GCVIAWNSNN LDSKVGGNYN YLYRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEYVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA 1020
SANLAAIKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASFVNIQ KEIDRLNEVA KNLNESLIDL 1200
QELGKYEQYI KWPWYIWLGF IAGLIAIVMV TIMLCCMTSC CSCLKGCCSC GSCC       1254
```

NUCLEIC ACID VACCINE AGAINST THE SARS-COV-2 CORONAVIRUS

CROSS-REFERENCE TO RELATED APPLICATIONS

This application is a continuation U.S. application Ser. No. 17/819,187 filed on Aug. 11, 2022, which is a continuation of International Appln. PCT/EP2021/025053, filed on Feb. 12, 2021, which itself claims the benefit of U.S. provisional application 62/976,148 filed on Feb. 13, 2020, and European Appln. EP 20305140.4 filed on Feb. 13, 2020, the contents of each of which are incorporated herein by reference in their entireties for all purposes.

REFERENCE TO SEQUENCE LISTING SUBMITTED ELECTRONICALLY

The instant application contains a Sequence Listing which has been submitted electronically in XML, format and is hereby incorporated by reference in its entirety. Said XML, copy, created on Jul. 12, 2023, is named B2006132EPWOUS.xml and is 191,004 bytes in size.

FIELD OF THE INVENTION

The invention relates to an immunogenic or vaccine composition against the 2019 novel coronavirus (SARS-CoV-2, 2019-nCov or COVID-19), comprising a nucleic acid construct encoding a SARS-CoV-2 coronavirus Spike (S) protein antigen or a fragment thereof comprising the receptor-binding domain (RBD), wherein the nucleic acid construct sequence is codon-optimized for expression in human. The invention also relates to said nucleic acid construct, derived vector, antigen encoded by said nucleic acid construct and to their use for the diagnosis, prevention and treatment of SARS-CoV-2 coronavirus infection.

BACKGROUND OF THE INVENTION

In December 2019, patients presenting with viral pneumonia were reported in Wuhan, China. A novel coronavirus was subsequently identified as the causative agent, and provisionally named 2019 novel coronavirus (2019-nCov or SARS-CoV-2) (Zhu N et al., N Engl J Med., 2020 Jan. 24). The virus swiftly spread within and outside China, leading to the WHO declaring a Public Health Emergency of International Concern on Jan. 30, 2020. With the aim of rapid development of a candidate vaccine, and based on the state of the art of betacoronaviruses biology, two suitable candidate antigens based on the spike (S) protein of the virus were designed.

Coronaviruses are enveloped, positive single stranded RNA viruses. Coronaviruses have been identified in various mammalians hosts such as bats, camels, or mice, among others. Several coronaviruses are pathogenic to human, leading to varying degrees of symptoms severity (Cui et al., Nat Rev Microbiol. 2019 March; 17(3):181-92). Highly pathogenic variants include the severe acute respiratory syndrome coronavirus (SARS-Cov) that emerged in China in 2002, resulting in ~8000 human infections and 700+ deaths (Peiris et al., Nat Med., 2004 December; 10(12 Suppl): S88-97) and the Middle East respiratory syndrome coronavirus (MERS-CoV), first detected in Saudi Arabia in 2012 and responsible for 2500 human infections and 850+ deaths (Zaki et al., N Engl J Med., 2012 Nov. 8; 367(19): 1814-20; Lee et al., BMC Infect Dis. 2017 Jul. 14; 17(1): 498).

Coronaviruses genomes encode non-structural polyprotein and structural proteins, including the Spike (S), envelope, membrane and nucleocapsid proteins. As seen notably with SARS-Cov, neutralizing antibodies and/or T-cell immune responses can be raised against several proteins but mostly target the S protein, suggesting that S protein-induced specific immune responses play important parts in the natural response to coronavirus infection (Saif L J, Vet Microbiol. 1993 November; 37(3-4):285-97). The S glycoprotein has key roles in the viral cycle, as it is involved in receptor recognition, virus attachment and entry, and is thus a crucial determinant of host tropism and transmission capacity. Expressed as precursor glycoprotein, S is cleaved in two subunits (S1, which contains the receptor binding domain (RBD), and S2) by proteases.

There is a need for new vaccines to control SARS-CoV-2 virus infection.

SUMMARY OF THE INVENTION

The inventors have engineered a nucleic acid vaccine against the 2019 novel coronavirus (SARS-CoV-2 or 2019-nCov) based on its Spike (S) protein coding sequence available in sequence data bases, which has been optimized for expression in human. Various nucleic acid constructs containing either the complete SARS-CoV-2 Spike, a Spike modified at the furin site), stabilized with proline residues and/or comprising a C-terminal deletion, or only the receptor binding domain (RBD) were engineered using the optimized Spike coding sequence. To ensure that the antigen will be able to generate a broad immune response that will also result in protection against novel variants of SARS-CoV-2, inventors included point modifications of the antigen in key areas of the spike and its RBD. This notably involved modifications close to the pocket of contact with the receptor ACE2 (region 480-505), as well as regions along the spike where changes (mutations or deletion) have been noted during the natural circulation of the virus in human. Animals were vaccinated with formulation of the various nucleic acid constructs by intramuscular, intranasal, or mixed administration using various prime boost immunization regimens. Nucleic acid vaccine was able to induce neutralizing antibody production. In correlation with strong neutralizing antibody induction, nucleic acid vaccine encoding the RBD antigen was able to provide protection from a SARS-CoV-2 challenge of immunized animals, The various derivatives of the initial antigen will be used in a composition or sequentially in prime boost regimens.

Therefore, the invention relates to an immunogenic or vaccine composition against SARS-CoV-2 virus comprising a nucleic acid construct encoding a SARS-CoV-2 virus Spike (S) protein antigen having at least 90% identity with the amino acid sequence from positions 19 to 1273 of SEQ ID NO: 2 or a fragment thereof comprising the receptor-binding-domain (RBD), wherein the nucleic acid construct sequence is codon-optimized for expression in human.

In some embodiments of the composition according to the invention, the nucleic acid construct comprises a sequence chosen from SEQ ID NO: 1, SEQ ID NO: 3, and the nucleotide sequences having at least 80% identity with said sequences.

In some preferred embodiments of the composition according to the invention, said nucleic acid construct comprises a Kozak sequence.

In some preferred embodiments, the nucleic acid construct comprises a sequence selected from the group consisting of SEQ ID NO: 10, 12, 14, 16, 18, 20, 22, 24, 29, 31, 33, 35, 37, 39, 41, 43, 45, 47, 49, 51, 53, 55, 57, 59, 61, 63, 65, the nucleotide sequences having at least 80% identity with said sequences, and the RNA sequences thereof; preferably selected from the group consisting of SEQ ID NO: 14, 16, 18, 20, 22, 24, 31, 33, 35, 37, the nucleotide sequences having at least 80% identity with said sequences, and the RNA sequences thereof.

In some embodiments of the composition according to the invention, said RBD fragment comprises an amino acid sequence having at least 90% identity with SEQ ID NO: 4.

In some preferred embodiments of the composition according to the invention, said S protein antigen or RBD fragment thereof comprises a signal peptide, preferably selected from the group consisting of the sequences SEQ ID NO: 5, 6 and 7.

In some preferred embodiments of the composition according to the invention, said S protein antigen or RBD fragment thereof further comprises at least an epitope recognized by human T cells; preferably human CD4+ T-cells; more preferably a Universal Pan HLA-DR Epitope such as PADRE (SEQ ID NO: 8); preferably wherein the S protein antigen or RBD fragment thereof and the epitope are separated by a linker, preferably comprising SEQ ID NO: 9.

In some preferred embodiments of the composition according to the invention, said S protein antigen or RBD fragment thereof comprises an amino acid sequence selected from the group consisting of SEQ ID NO: 11, 13, 15, 17, 19, 21, 23, 25, 30, 32, 34; 36, 38, 40, 42, 44, 46, 48, 50, 52, 54, 56, 58, 60, 62, 64, 66 and the sequences having at least 90% identity with said sequences; preferably selected from the group consisting of SEQ ID NO: 15, 17, 19, 21, 23, 25, 32, 34, 36, 38, and the sequences having at least 90% identity with said sequences.

In some embodiments of the composition according to the invention, said nucleic acid construct is a mammalian expression cassette, preferably human expression cassette, wherein the coding sequence of said S protein antigen or RBD fragment thereof is operably linked to appropriate regulatory sequence(s) for their expression in an individual's target cells or tissue(s); preferably comprising a promoter; more preferably further comprising one or more of an enhancer, terminator or intron.

In some embodiments of the composition according to the invention, said nucleic construct is RNA or DNA. In some particular embodiments, the RNA is non-replicating or self-amplifying mRNA comprising a cap structure, 5'- and 3'-untranslated regions (UTRs), and a 3'poly(A) tail operably linked to the coding sequence of said S protein antigen or RBD fragment thereof.

In some embodiments, the composition according to the invention comprises a vector comprising said nucleic acid construct; preferably a viral vector, a plasmid, a nucleic acid delivery agent or combination thereof. In some particular embodiments, said nucleic acid construct, preferably an expression cassette, is inserted into a viral vector or a plasmid. The viral vector is advantageously selected from the group consisting of: cytomegalovirus, adenovirus, vesicular stomatitis virus, modified vaccinia virus ankara and measles virus. In some particular embodiments, the nucleic acid delivery agent comprises tetrafunctional non-ionic amphiphilic block copolymers comprising at least one hydrophilic block and at least one hydrophobic block. In some particular embodiments, the plasmid is combined with a nucleic acid delivery agent, preferably comprising tetrafunctional non-ionic amphiphilic block copolymers comprising at least one hydrophilic block and at least one hydrophobic block. In some particular embodiments, the nucleic acid delivery agent comprises a particle or vesicle, in particular lipid-based micro- or nano-vesicle or particle such as liposome or lipid nanoparticle (LNP). In some particular embodiments, the nucleic acid construct is RNA, in particular mRNA according to the present disclosure and the vector is a particle or vesicle, in particular LNP.

In some embodiments of the invention, the immunogenic or vaccine composition further comprises a pharmaceutically acceptable vehicle and/or an adjuvant.

In some embodiments of the invention, the immunogenic or vaccine composition induces humoral and cellular immune responses against said SARS-CoV-2 virus; preferably wherein the humoral immune response comprises neutralizing antibodies against said SARS-CoV-2 virus and/or the cellular immune response comprises CD4+ and/or CD8+ T-cells against said SARS-CoV-2 virus.

The invention also relates to the immunogenic or vaccine composition according to the present disclosure, for use in the prevention or treatment of SARS-CoV-2 virus infection.

The invention also relates to the nucleic construct according to the present disclosure, the vector comprising said nucleic acid construct, the SARS-CoV-2 virus S protein antigen or fragment thereof comprising the receptor binding domain encoded by said nucleic acid construct and to their use for the diagnosis, prevention and treatment of SARS-CoV-2 coronavirus infection.

DETAILED DESCRIPTION OF THE INVENTION

Nucleic Acid Construct and Vector

The invention relates to a nucleic acid construct encoding a SARS-CoV-2 virus Spike (S) protein antigen having at least 90% identity with the amino acid sequence from positions 19 to 1273 of SEQ ID NO: 2 or a fragment thereof comprising the receptor-binding-domain, wherein the nucleic acid construct sequence is codon-optimized for expression in human.

The nucleic acid construct may consist of recombinant, synthetic or semi-synthetic nucleic acid which is expressible in the individual's target cells or tissue. The nucleic acid may be DNA, RNA, mixed and may further be modified. In some embodiments, the nucleic acid construct consists of recombinant or synthetic DNA or RNA, in particular mRNA. The nucleic construct has usually a length of up to 10000 nt. Preferably up to 9000, 8000, 7000, 6000 or 5000 nt.

As used herein "individual" or "subject" refers to a human.

The terms "a", "an", and "the" include plural referents, unless the context clearly indicates otherwise. As such, the term "a" (or "an"), "one or more" or "at least one" can be used interchangeably herein.

As used herein, SARS-CoV-2 refers to any isolate, strain or variant of SARS-CoV-2.

As used herein, SARS-CoV-2 infection refers to SARS-CoV-2 infection and associated disease (Covid-19).

The nucleic acid sequences disclosed herein are provided in their DNA form. However, the present invention encompasses the RNA equivalent of any of the disclosed DNA sequences.

SEQ ID NO: 2 is the amino acid sequence of the Spike (S) protein of the 2019 novel coronavirus initially named 2019-nCov and renamed SARS-CoV-2 (Severe acute respiratory syndrome coronavirus 2). The S protein comprises a signal peptide (SP) from position 1 to 18 which is cleaved in the mature S protein. The S protein is cleaved into two subunits, S1 which contains the receptor binding domain (RBD) and S2, by proteases. S1 is from positions 19 to 661 of SEQ ID NO: 2 and S2 is from positions 662 to 1270 of SEQ ID NO: 2 (See FIG. 3). The receptor binding domain (RBD) is from positions 331 to 524 in SEQ ID NO: 2 and corresponds to SEQ ID NO: 4 in wild-type SARS-CoV-2. By simple sequence alignment with SEQ ID NO: 2, one skilled in the art can easily determine the positions of the RBD in the sequence of a S protein antigen variant or fragment thereof according to the present disclosure. The RBD from wild-type SARS-CoV-2 S protein or S protein antigen variant or fragment thereof according to the present disclosure is highly reactive to anti-S neutralizing antibodies and competitively inhibits SARS-CoV-2 virus neutralisation by said anti-S neutralizing antibodies. Therefore, the S antigen and the S antigen fragment according to the invention which comprises the RBD (RBD fragment, RBD antigen or RBD antigen fragment) are highly reactive to anti-S neutralizing antibodies and competitively inhibit SARS-CoV-2 virus neutralisation by said anti-S neutralizing antibodies. This reactivity may be tested by standard antigen/antibody binding assays such as ELISA and the like or by standard virus neutralisation assay that are well-known in the art such as those disclosed in the examples of the application. The amino acid positions are indicated according to the numbering in the sequence SEQ ID NO: 2.

The S protein antigen or S antigen according to the present disclosure has at least 90% identity with the amino acid sequence from positions 19 to 1273 of SEQ ID NO: 2. In some embodiments, the S antigen has 91%, 92%, 93%, 94%, 95%, 96%, 97%, 98%, 99% or 100% identity with the amino acid sequence from positions 19 to 1273 of SEQ ID NO: 2.

In some embodiments, said RBD antigen comprises or consists of an amino acid sequence having at least 90% identity with SEQ ID NO: 4. The RBD antigen fragment may have 91%, 92%, 93%, 94%, 95%, 96%, 97%, 98%, 99% or 100% identity with SEQ ID NO: 4. The RBD antigen fragment according to the present disclosure refers to a functional fragment which is bound by anti-S neutralizing antibodies in standard antigen/antibody binding assays such as ELISA and the like and competitively inhibit SARS-CoV-2 virus neutralisation by said anti-S neutralizing antibodies in standard virus neutralization assays. In some preferred embodiments, said RBD antigen fragment consists of the amino acid sequence SEQ ID NO: 4 or a sequence having at least 90% identity with SEQ ID NO: 4.

In some particular embodiments, the S antigen or RBD antigen fragment thereof comprises one or more mutations within the RBD selected from the group consisting of: K417N or K417T, N439N, L452R, Y453F, S477N, E484K, F490S, and N501Y, said positions being indicated according to the numbering in the sequence SEQ ID NO: 2. The S or RBD antigen may have 1, 2, 3, 4, 5, 6 or all of said mutations. In some particular embodiments, the S or RBD antigen comprises at least one mutation close to the pocket of contact with the receptor ACE2 (region 480-505) chosen from E484K, F490S, and N501Y; preferably at least the E484K and/or N501Y mutations.

In some preferred embodiments, the S or RBD antigen comprises the following mutations: N501Y; E484K and N501Y; K417T or K417N, E484K and N501Y; K417N, N439N, Y453F, S477N, E484K, F490S, and N501Y; K417N, N439N, L452R, S477N, E484K, F490S, and N501Y. In some more preferred embodiment, the S antigen comprises or consists of an amino acid sequence having at least 90% identity with any one of SEQ ID NO: 44, 46, 48, 50, 52, 54, 56, 58, 60, 62, 64 and 66, wherein said variant comprises one or more of said mutations within the RBD domain. In some more preferred embodiment, the RBD antigen comprises or consists of an amino acid sequence having at least 90% identity with any one of SEQ ID NO: 32, 34, 36 and 38, wherein said variant comprises one or more of said mutations within the RBD domain.

In some particular embodiments, the S antigen comprises a mutation which inactivates the furin cleavage site (PR-RAR; positions 681 to 685 in SEQ ID NO: 2). Examples of such furin site mutation, including deletion or substitution are well-known in the art and include the deletion of residues P681 to A684 (Johnson et al., Nature, 2021, doi.org/10.1038/s41586-021-03237-4) and the R682G, R683S and/or R685S substitutions. In some preferred embodiments, the S antigen comprises the R682G, R683S and R685S substitutions. In some more preferred embodiment, the S antigen comprises or consists of an amino acid sequence having at least 90% identity with SEQ ID NO: 30, wherein the variant comprises said furin site mutation.

In some particular embodiments, the S antigen comprises a mutation which stabilizes the Spike trimer. Such mutations which are well-known in the art include the K986P and V987P mutations (S-2P variant) and other proline substitutions, in particular F817P, A892P, A899P and A942P, which can be combined together to obtain a multiple proline variant, in particular hexaproline variant (HexaPro). In some preferred embodiments, the S antigen comprises the K986P and V987P mutations, and eventually one to four additional proline mutations selected from the group consisting of F817P, A892P, A899P and A942P. In some more preferred embodiment, the S antigen comprises or consists of an amino acid sequence having at least 90% identity with any one of SEQ ID NO: 42, 48, 50, 56, 58, 64 and 66, wherein the variant comprises at least one of said Proline mutations.

In some particular embodiments, the S antigen comprises a C-terminal deletion of 1 to 25 or more amino acids, preferably 5 to 25, 10 to 25 amino acids; more preferably 18 to 25 amino acids (18, 19, 20, 21, 22, 23, 24, 25). In some preferred embodiments, the S antigen comprises the deletion of the C-terminal residues from position K1255 (deletion K1255 to T1273). In some more preferred embodiment, the S antigen comprises or consists of an amino acid sequence having at least 90% identity with any one of SEQ ID NO: 40, 46, 50, 54, 58, 62 and 66, wherein the variant comprises said C-terminal deletion.

In some particular embodiments, the S antigen comprises one or more mutations selected from the group consisting of: the substitutions L18F, T20N, P26S, D80A, D138Y, R190S, D215G, A570D, D614G, H655Y, P681H, A701V, T716I, S982A, T1027I, D1118H and V1176F; and the deletions delta 69-70, delta 144 and delta 242-244. In some preferred embodiments, the S antigen comprises at least five of said substitutions outside the RBD, and eventually also at least one or two of said deletions. In some more preferred embodiment, the S antigen comprises or consists of an amino acid sequence having at least 90% identity with any one of SEQ ID NO: 44, 46, 48, 50, 52, 54, 56, 58, 60, 62, 64 and 66, wherein said variant comprises one or more of said mutations outside the RBD domain.

The percent amino acid or nucleotide sequence identity is defined as the percent of amino acid residues or nucleotides in a Compared Sequence that are identical to the Reference Sequence after aligning the sequences and introducing gaps if necessary, to achieve the maximum sequence identity and not considering any conservative substitution as part of the sequence identity. Sequence identity is calculated over the entire length of the Reference Sequence. Alignment for purposes of determining percent amino acid or nucleotide sequence identity can be achieved in various ways known to a person of skill in the art, for instance using publicly available computer software such as the GCG (Genetics Computer Group, Program Manual for the GCG Package, Version 7, Madison, Wisconsin) pileup program, or any of sequence comparison algorithms such as BLAST (Altschul et al., J. Mol. Biol., 1990, 215, 403-10), FASTA or CLUSTALW.

The nucleic acid construct sequence is codon-optimized for expression in human. Codon optimization is used to improve protein expression level in living organism by increasing translational efficiency of target gene. Appropriate methods and softwares for codon optimization in the desired host are well-known in the art and publically available (see for example the GeneOptimizer software suite in Raab et al., Systems and Synthetic Biology, 2010, 4, (3), 215-225). Codon optimization of the nucleic acid construct sequence relates to the coding sequences but not to the other (non-coding) sequences of the nucleic acid construct.

In some embodiments, the nucleic acid construct comprises a sequence chosen from SEQ ID NO: 1 and SEQ ID NO: 3, the nucleotide sequences having at least 80% identity with said sequences, and the RNA sequences thereof. The nucleotide sequences may have 81%, 82%, 83%, 84%, 84%, 85%, 86%, 87%, 88%, 89%, 90%, 91%, 92%, 93%, 94%, 95%, 96%, 97%, 98%, 99% or 100% identity with SEQ ID NO: 1 or SEQ ID NO: 3.

In some preferred embodiments, the nucleic acid construct comprises a Kozak consensus sequence or Kozak sequence which is a nucleic acid motif that functions as the protein translation initiation site in most eukaryotic mRNA transcripts. The Kozak sequence may be acc (in position −3 to −1) or cacc (in positions −4 to −1) relative to the atg initiation codon of the S protein antigen or antigen fragment.

In some preferred embodiments, the nucleic acid construct comprises a sequence selected from the group consisting of SEQ ID NO: 10, 12, 14, 16, 18, 20, 22, 24, 29, 31, 33, 35, 37, 39, 41, 43, 45, 47, 49, 51, 53, 55, 57, 59, 61, 63, 65, and the nucleotide sequences having at least 80% identity with said sequences, and the RNA equivalent thereof. The nucleotide sequences may have 81%, 82%, 83%, 84%, 84%, 85%, 86%, 87%, 88%, 89%, 90%, 91%, 92%, 93%, 94%, 95%, 96%, 97%, 98%, 99% or 100% identity with any one of SEQ ID NO: 10, 12, 14, 16, 18, 20, 22, 24, 29, 31, 33, 35, 37, 39, 41, 43, 45, 47, 49, 51, 53, 55, 57, 59, 61, 63 or 65. In some more preferred embodiments, the nucleic acid construct comprises a sequence selected from the group consisting of SEQ ID NO: 14, 16, 18, 20, 22, 24, 31, 33, 35, 37, the nucleotide sequences having at least 80% identity with said sequences, and the RNA sequences thereof. All the above listed sequences are codon-optimized for expression in human and comprise a Kozak sequence. The above listed variants of the listed sequences refer to sequences that are codon-optimized for expression in human and preferably comprising a Kozak sequence.

In some preferred embodiments, said S protein antigen or RBD fragment thereof comprises a signal peptide (SP) or signal sequence. The SP is at the amino terminus of a protein and is involved in transport of the protein to or through cell membranes, transport to different membranous cellular compartments, or secretion of the protein from the cell. Signal peptides are removed from the mature protein during this process by a specific peptidase. For example, the signal peptide may be the natural SP of the S protein (SEQ ID NO: 5) or the SP of a human protein such as CD5 (SEQ ID NO: 6) or IL2 (SEQ ID NO: 7). In some more preferred embodiments, the signal peptide is selected from the group consisting of the sequences SEQ ID NO: 5, 6 and 7 and the derived sequences having a C-ter deletion of 1, 2, 3 or 4 amino acids. In some embodiments, the SP of the human protein further comprises the 1 to 4 amino acid residues in positions +1 to +4 relative to the peptidase cleavage site in said human protein. In some embodiments, the SP of the SARS-CoV-2 S protein antigen (SEQ ID NO: 5) further comprises 1, 2, 3 or 4 amino acid residues at its Cter, preferably comprising V and/or A or is truncated from 1, 2, 3 or 4 amino acid residues at its Cter.

In some preferred embodiments, the S protein antigen or RBD fragment thereof further comprises at least an epitope recognized by human T cells; preferably human CD4+ T-cells; more preferably a Universal Pan HLA-DR Epitope such as PADRE. PADRE is a universal synthetic 13 amino acid peptide (SEQ ID NO: 8) that activates CD4+ T cells. As PADRE binds with high affinity to 15 of the 16 most common human HLA-DR types, it provides potent CD4+ T cell responses, and may overcome problems caused by polymorphism of HLA-DR molecules in human populations. The S protein antigen or fragment thereof and the epitope are advantageously separated by a linker, such as for example preferably a linker comprising or consisting of SEQ ID NO: 9. In some more preferred embodiments, the S protein antigen or fragment thereof comprises PADRE (SEQ ID NO: 8) and preferably further comprises the linker of SEQ ID NO: 9, corresponding to SEQ ID NO: 27. The linker and PADRE sequences are advantageously encoded by the nucleotide sequence SEQ ID NO: 26.

The S antigen and its fragment according to the present disclosure usually do not comprise any other protein moiety or domain other than those disclosed above. In particular, the S antigen and its fragment according to the present disclosure differ from the prior art antigens in that they do not comprise a protein stabilizing moiety such as an immunoglobulin Fc fragment.

In some preferred embodiments, said S protein antigen or RBD fragment thereof comprises an amino acid sequence selected from the group consisting of the sequences SEQ ID NO: 11, 13, 15, 17, 19, 21, 23, 25, 30, 32, 34, 36, 38, 40, 42, 44, 46, 48, 50, 52, 54, 56, 58, 60, 62, 64, 66 and the variant thereof having at least 90% identity (91%, 92%, 93%, 94%, 95%, 96%, 97%, 98%, 99% or 100% identity) with one of said sequences. SEQ ID NO: 11, 13, 40, 42, 44, 46, 48, 50, 52, 54, 56, 58, 60, 62, 64, 66 comprise the full length S protein (Spike) sequence including the natural SP. SEQ ID NO: 30 comprises a spike modified at the furin site (spike delta furin). SEQ ID NO: 15, 17, 25, 32, 34, 36 and 38 comprise the RBD with the natural SP at the N-terminus. SEQ ID NO: 19, 21, 23, 25 comprise the RBD with another SP at the N-terminus (SEQ ID NO: 6 or 7). SEQ ID NO: 13, 17, 21 and 25 comprise the linker (SEQ ID NO: 9) and PADRE at the C-terminus (SEQ ID NO: 27).

In some more preferred embodiments, the nucleic acid construct encodes a RBD fragment having a sequence selected from the group consisting of the sequences SEQ ID NO: 15, 17, 19, 21, 23, 25, 32, 34, 36, 38 and the variant thereof having at least 90% identity (91%, 92%, 93%, 94%, 95%, 96%, 97%, 98%, 99% or 100% identity) with one of said sequences.

A variant according to the present disclosure refers to a functional variant which is bound by anti-S neutralizing antibodies in standard antigen/antibody binding assays such as ELISA and the like and competitively inhibit SARS-CoV-2 virus neutralisation by said anti-S neutralizing antibodies in standard virus neutralization assays In some embodiments, said nucleic acid construct is a mammalian expression cassette, preferably human expression cassette, wherein the coding sequence of said S protein antigen or RBD fragment thereof is operably linked to appropriate regulatory sequence(s) for their expression in an individual's target cells or tissue(s). In some particular embodiments, the target cell(s) or tissue(s) is epithelial cell(s) or tissue(s). Such sequences which are well-known in the art include in particular a promoter, and further regulatory sequences capable of further controlling the expression of a transgene, such as without limitation, enhancer, terminator and intron. In some particular embodiments, the expression cassette comprises a promoter; preferably further comprises one or more of an enhancer, terminator or intron.

The promoter may be a tissue-specific, ubiquitous, constitutive or inducible promoter that is functional in the individual's target cells or tissue, in particular epithelial cell(s) or tissue(s). Examples of constitutive promoters which can be used in the present invention include without limitation: phosphoglycerate kinase promoter (PGK), elongation factor-1 alpha (EF-1 alpha) promoter including the short form of said promoter (EFS), viral promoters such as cytomegalovirus (CMV) immediate early enhancer and promoter (optionally with the CMV enhancer), cytomegalovirus enhancer/chicken beta actin (CAG) promoter, SV40 early promoter and retroviral 5' and 3' LTR promoters including hybrid LTR promoters. Preferred ubiquitous promoter is CMV promoter. Examples of inducible promoters which can be used in the present invention include Tetracycline-regulated promoters. The promoters are advantageously human promoters, i.e., promoters from human cells or human viruses. Such promoters are well-known in the art and their sequences are available in public sequence data bases.

In some embodiments, the nucleic acid construct encodes other antigen(s), in particular human vaccine antigen(s) from other pathogens.

In some preferred embodiments, the nucleic acid construct is DNA, wherein the coding sequence of said S protein antigen or RBD fragment thereof is operably linked to appropriate regulatory sequence(s) for their expression in an individual's target cells or tissue(s) as disclosed above. The DNA construct advantageously comprises a mammalian expression cassette as disclosed above.

In some other preferred embodiments, the nucleic acid construct is RNA, preferably mRNA, wherein the coding sequence of said S protein antigen or RBD fragment thereof is operably linked to appropriate regulatory sequence(s) for their expression in an individual's target cells or tissue(s). mRNA vaccines are well-known in the art (reviewed in Jackson et al., Vaccines, 2020, 5, 11, doi.10.1038). mRNA is delivered into the host cell cytoplasm where expression generates the antigen of interest. mRNA construct comprises a cap structure, 5' and 3'untranslated regions (UTRs), and open reading frame (ORF), and a 3'poly(A) tail. mRNA construct may be non-replicating mRNA (MRM) or self-amplifying mRNA (SAM). SAM comprises the inclusion of genetic replication machinery derived from positive-strand mRNA viruses, most commonly alphaviruses such as Sindbis and Semliki-Forest viruses. In SAM constructs, the ORF encoding viral structural protein is replaced by the transcript encoding the vaccine antigen of interest, and the viral RNA-dependent RNA polymerase is retained to direct cytoplasmic amplification of the replicon construct. Trans-replicating RNA are disclosed for example in WO 2017/162461. RNA replicon from alphavirus suitable for gene expression are disclosed in WO 2017/162460. mRNA manufacturing process uses plasmid DNA (pDNA) containing a DNA-dependent RNA polymerase promoter, such as T7, and the corresponding sequence for the mRNA construct. The pDNA is linearized to serve as a template for the DNA-dependent RNA polymerase to transcribe the mRNA, and subsequently degraded by a DNase process step. The addition of the 5' cap and the 3'poly(A) tail can be achieved during the in vitro transcription step or enzymatically after transcription. Enzymatic addition of the cap can be accomplished by using guanylyl transferase and 2'-O-methyltransferase to yield a Cap0($^{N7Me}$GpppN) or Cap 1 ($^{N7Me}$GpppN$^{2'-oMe}$) structure, respectively, while the poly-A tail can be achieved through enzymatic addition via poly-A polymerase. mRNA is then purified using standard methods suitable for mRNA purification such as high-pressure liquid chromatography (HPLC) and others. Methods for producing mRNA are disclosed for example in WO 2017/182524.

To improve translation efficiency in vaccinated subject cells, the mRNA construct according to the invention comprises a sequence which is codon-optimized for expression in human. Further improvements of the mRNA construct according to the invention to improve its stability and translation efficiency in vivo include optimization the length and regulatory element sequences of 5'-UTR and 3'UTR; base and/or sugar modifications in the cap structure to increase ribosomal interaction and/or mRNA stability; and modified nucleosides. Modified nucleosides may be in the 5'-UTR, 3'-UTR or ORF. Examples of modified nucleosides include pseudouridine and N-1-methylpseudouridine that remove intracellular signalling triggers for protein kinase R activation. Examples of modified nucleosides that reduce RNA degradation into cells are disclosed in WO 2013/039857. Modified cap structures are disclosed in WO 2011/015347 and WO 2019/175356. Optimized 3'-UTR sequences are disclosed in WO 2017/059902. Modified polyA sequences which improve RNA stability and translation efficiency are disclosed in US 2020/0392518. Modified mRNA with improved stability and translation efficiency are also disclosed in WO 2007/036366.

The invention also relates to a vector comprising the nucleic acid construct according to the present disclosure. The invention may use any vector suitable for the delivery and expression of nucleic acid into individual's cells, in particular suitable for vaccination. Such vectors that are well-known in the art include viral and non-viral vectors.

Non-viral vector includes the various (non-viral) agents which are commonly used to either introduce or maintain nucleic acid into individual's cells. Agents which are used to introduce nucleic acid into individual's cells by various means include in particular polymer-based, particle-based, lipid-based, peptide-based delivery vehicles or combinations thereof, such as with no limitations cationic polymer, dendrimer, micelle, liposome, lipopolyplex, exosome, microparticle and nanoparticle including lipid nanoparticle (LNP) and viral-like particles; and cell penetrating peptides (CPP).

In some embodiments, said nucleic-acid delivery agent comprises tetrafunctional non-ionic amphiphilic block copolymers comprising at least one hydrophilic block and at least one hydrophobic block. Such agents are disclosed in WO 2019/092002.

Agents which are used to maintain nucleic acid into individual's cells include in particular naked nucleic acid vectors such as plasmids, transposons and mini-circles. These vectors have minimal eukaryotic sequences to minimize the possibility of chromosomal integration. Examples of such vectors are the plasmids pVAX1 and pGWIS which are commercially available. In addition, these approaches can advantageously be combined to introduce and maintain the nucleic acid of the invention into individual's cells.

In some embodiments, a plasmid, preferably with minimal eukaryotic sequences, comprising an expression cassette including the nucleic acid construct according to the present disclosure is combined with a nucleic-acid delivery agent, preferably an agent comprising tetrafunctional non-ionic amphiphilic block copolymers comprising at least one hydrophilic block and at least one hydrophobic block as disclosed above.

In some embodiments, a mRNA construct according to the present invention as disclosed above is combined with a nucleic-acid delivery agent suitable for delivery of mRNA into mammalian host cells that are well-known in the art. The mRNA delivery agent may be a polymeric carrier, polycationic protein or peptide, lipid nanoparticle or other. For example, the mRNA (non-replicating or self-amplifying) may be delivered into cells using polymers, in particular cationic polymers, such as polyethylenimine (PEI), poly-L-Lysin (PEL), polyvinylamine (PVA) or polyallylamine (PAA), wherein the mRNA is preferentially present in the form of monomers, dimers, trimers or oligomers as disclosed in WO 2021/001417. Alternatively, the mRNA may be combined with polyalkyleneimine in the form of polyplex particles, suitable for intramuscular administration as disclosed in WO 2019/137999 or WO 2018/011406. The mRNA may also be combined with a polycation, in particular protamine, as disclosed in WO 2016/000792. One or more mRNA molecules may be formulated within a cationic lipid nanoparticle (LNP); for example the formulation may comprise 20-60% cationic lipid; 5-25% non-cationic lipid, 25-55% sterol and 0.5-15% PEG-modified lipid as disclosed WO 2015/164674. The mRNA may also be formulated in RNA decorated particles such as RNA decorated lipid particles, preferably RNA decorated liposomes as disclosed in WO 2015/043613.

Viral vectors are by nature capable of penetrating into cells and delivering nucleic acid(s) of interest into cells, according to a process named as viral transduction. As used herein, the term "viral vector" refers to a non-replicating, non-pathogenic virus engineered for the delivery of genetic material into cells. In viral vectors, viral genes essential for replication and virulence are replaced with an expression cassette for the transgene of interest. Thus, the viral vector genome comprises the transgene expression cassette flanked by the viral sequences required for viral vector production. As used herein, the term "recombinant virus" refers to a virus, in particular a viral vector, produced by standard recombinant DNA technology techniques that are known in the art. As used herein, the term "virus particle" or "viral particle" is intended to mean the extracellular form of a non-pathogenic virus, in particular a viral vector, composed of genetic material made from either DNA or RNA surrounded by a protein coat, called the capsid, and in some cases an envelope derived from portions of host cell membranes and including viral glycoproteins. As used herein, a viral vector refers to a viral vector particle.

A preferred viral vector for delivering the nucleic acid of the invention is a vaccine vector, preferably selected from the group consisting of poxvirus such as vaccinia virus, replication-defective alphavirus replicons, cytomegalovirus, adenovirus, modified vaccinia virus Ankara, vesicular stomatitis virus and measles virus (For a review, see Humphreys et al., Immunology, 2017, 153, 1-9). In some particular embodiment, the viral vector is selected from the group consisting of: cytomegalovirus, adenovirus, modified vaccinia virus Ankara, vesicular stomatitis virus and measles virus.

In particular embodiments, the vector is a particle or vesicle, in particular lipid-based micro- or nano-vesicle or particle such as liposome or lipid nanoparticle (LNP). In more particular embodiments, the nucleic acid is RNA, in particular mRNA and the vector is a particle or vesicle, in particular LNP as described above. The LNP:mRNA mass ratio can be around 10:1 to 30:1.

In some embodiments, vector comprises another nucleic acid construct coding another antigen, in particular human vaccine antigen(s) from other pathogens.

The nucleic acid construct, preferably comprising an expression cassette, is useful for producing recombinant SARS-CoV-2 virus S protein antigen and fragment thereof comprising the receptor-binding domain (RBD) according to the present disclosure by expression from an appropriate recombinant expression vector in a suitable cell system (eukaryotic including mammalian and insect cells or prokaryotic). For example, the vector may be a plasmid in mammalian cells or a baculovirus vector in insect cells.

Therefore, the invention also relates to a host cell (eukaryotic or prokaryotic) modified with a recombinant vector comprising the nucleic acid construct according to the present disclosure.

Immunogenic or Vaccine Composition and Therapeutic Use

The invention further provides an immunogenic or vaccine composition comprising a comprising a nucleic acid construct or vector according to the present disclosure.

The immunogenic or vaccine composition may comprise a mixture of different nucleic acid constructs or vectors according to the present invention. In particular, the composition may comprise a mixture of nucleic acid constructs or vectors encoding variants of the S antigen and/or RBD antigen as described herein. In some embodiments, the composition encodes at least two S and/or RBD antigens having different mutations within the RBD sequence and/or outside the RBD sequence as described herein. In some preferred embodiments, the pharmaceutical composition encodes at least two, three or four different RBD antigens selected from the group consisting of the sequences SEQ ID NO: 15, 32, 34, 36 and 38.

In some embodiments, the pharmaceutical composition further comprises a pharmaceutically acceptable vehicle and/or an adjuvant.

The pharmaceutical vehicles are those appropriate to the planned route of administration, which are well known in the art.

Non-limitative examples of adjuvants suitable for use in the composition of the invention include: CpG oligodeoxynucleotide, polyI:C (polyinosinc-polycytidylic acid), oil emulsion, mineral substances, bacterial extracts, saponin, aluminium salts, monophosphoryl-lipid A (MPL) and squalene.

The pharmaceutical composition comprises a therapeutically effective amount of the nucleic acid construct or vector sufficient to induce an immune response, in particular a protective immune response against SARS-CoV-2 virus infection, in the individual to whom it is administered. The pharmaceutically effective dose depends upon the composition used, the route of administration, the physical characteristics of the specific individual under consideration, concurrent medication, and other factors, that those skilled in the medical arts will recognize.

The pharmaceutical composition of the present invention is generally administered according to known procedures, at dosages and for periods of time effective to induce a beneficial effect in the individual. The administration may be by injection or by mucosal administration, in particular intranasal administration, or mixed administration. For example, the administration may be by intramuscular, intradermal, intravenous or subcutaneous injection, transdermal (such as patch) or intranasal (such as spray) applications, oral, or mixed. In some embodiments, the administration is intramuscular, intranasal or mixed intranasal and intramuscular. The pharmaceutical composition may comprise between 10 ng and 10 mg of nucleic acid construct or vector of the invention; preferably between 100 ng and 2.5 mg, more preferably between 1 µg and 500 µg. The pharmaceutical composition is administered 1 to 3 times at intervals of 2 to 25 weeks. In some embodiments, the pharmaceutical composition is administered according to a prime-boost regimen comprising 2 or 3 administrations in total, preferably intramuscular, intranasal or mixed. In some preferred embodiments the prime-boost regimen comprises 2 administrations at interval of at least 3 weeks, preferably 3, 4, 5 or 6 weeks. In some other preferred embodiments the prime-boost regimen comprises 3 administrations at intervals of up to 3 weeks, preferably 1 or 2 weeks.

In some embodiments, several pharmaceutical compositions, comprising different nucleic acid constructs or vectors according to the present invention are administered separately or sequentially. In particular, several pharmaceutical compositions encoding different variants of the S antigen and/or RBD fragment thereof are administered separately or sequentially. In some embodiments, the pharmaceutical compositions all together encode at least two different RBD antigens selected from the group consisting of the sequences SEQ ID NO: 15, 32, 34, 36 and 38.

In some embodiments of the invention, the immunogenic or vaccine composition induces humoral and cellular immune responses against said SARS-CoV-2 virus; preferably wherein the humoral immune response comprises neutralizing antibodies against said SARS-CoV-2 virus, in particular SARS-CoV-2 and/or the cellular immune response comprises CD4+ and/or CD8+ T-cells against said SARS-CoV-2 virus.

The invention also relates to the immunogenic or vaccine composition according to the present disclosure, for use in the prevention or treatment of SARS-CoV-2 virus infection.

The invention provides also a method for preventing SARS-CoV-2 virus infection in an individual, comprising: administering a therapeutically effective amount of the pharmaceutical composition according to the invention to the individual.

Antigen, Diagnostic and Therapeutic Uses

The invention also relates to the SARS-CoV-2 virus S protein antigen or fragment thereof comprising the receptor binding domain according to the present disclosure.

The SARS-CoV-2 virus Spike (S) protein antigen has at least 90% identity with the amino acid sequence from positions 19 to 1273 of SEQ ID NO: 2. The S antigen fragment comprises an amino acid sequence having at least 90% identity with SEQ ID NO: 4.

In some preferred embodiments, said S protein antigen or fragment thereof comprises a signal peptide (SP) or signal sequence. The SP is at the amino terminus of a protein and is involved in transport of the protein to or through cell membranes, transport to different membranous cellular compartments, or secretion of the protein from the cell. Signal peptides are removed from the mature protein during this process by a specific peptidase. For example, the signal peptide may be the natural SP of the S protein (SEQ ID NO: 5) or the SP of a human protein such as CD5 (SEQ ID NO: 6) or IL2 (SEQ ID NO: 7). In some more preferred embodiments, the signal peptide is selected from the group consisting of the sequences SEQ ID NO: 5, 6 and 7.

In some preferred embodiments, the S protein antigen or fragment thereof further comprises at least an epitope recognized by human T cells; preferably human CD4+ T-cells; more preferably a Universal Pan HLA-DR Epitope such as PADRE. PADRE is a universal synthetic 13 amino acid peptide (SEQ ID NO: 8) that activates CD4+ T cells. As PADRE binds with high affinity to 15 of the 16 most common human HLA-DR types, it provides potent CD4+ T cell responses, and may overcome problems caused by polymorphism of HLA-DR molecules in human populations. The S protein antigen or fragment thereof and the epitope are advantageously separated by a linker, such as for example preferably a linker comprising or consisting of SEQ ID NO: 9. In some more preferred embodiments, the S protein antigen or fragment thereof comprises PADRE (SEQ ID NO: 8) and preferably further comprises the linker of SEQ ID NO: 9, corresponding to SEQ ID NO: 27.

The S antigen and its fragment according to the present disclosure usually do not comprise any other protein moiety or domain other than those disclosed above. In particular, the S antigen and its fragment according to the present disclosure differ from the prior art antigens in that they do not comprise a protein stabilizing moiety such as an immunoglobulin Fc fragment.

In some preferred embodiments, said S protein antigen or fragment thereof comprises an amino acid sequence selected from the group consisting of the sequences SEQ ID NO: 11, 13, 15, 17, 19, 21, 23, 25, 30, 32, 34, 36, 38, 40, 42, 44, 46, 48, 50, 52, 54, 56, 58, 60, 62, 64, 66, and the variant thereof having at least 90% identity (91%, 92%, 93%, 94%, 95%, 96%, 97%, 98%, 99% or 100% identity) with one of said sequences. SEQ ID NO: 11, 13, 40, 42, 44, 46, 48, 50, 52, 54, 56, 58, 60, 62, 64, 66 comprise the full length S protein sequence including the natural SP. SEQ ID NO: 30 comprises a spike modified at the furin site (spike delta furin). SEQ ID NO: 15, 17, 25, 32, 34, 36 and 38 comprise the RBD with the natural SP at the N-terminus. SEQ ID NO: 19, 21, 23, 25 comprise the RBD with another SP at the N-terminus (SEQ ID NO: 6 or 7). SEQ ID NO: 13, 17, 21 and 25 comprise the linker (SEQ ID NO: 9) and PADRE at the C-terminus (SEQ ID NO: 27). A variant according to the present disclosure refers to a functional variant which is bound by anti-S neutralizing antibodies in standard antigen/antibody binding assays such as ELISA and the like.

The SARS-CoV-2 virus S protein antigen and fragment thereof comprising the receptor binding domain according to the present disclosure are useful as reagent for the detection or diagnosis of SARS-CoV-2 virus.

In some aspects, the method of detection or diagnosis of SARS-CoV-2 virus comprises determining the presence of antibodies against said virus or thereto in a sample.

The detection or diagnosis is generally performed by immunoassay. Immunoassays are well-known techniques for antibody detection which rely on the detection of antigen-antibody complexes using an appropriate label. The method of the invention may use any immunoassay such as with no limitations, immunoblotting, immunoprecipitation, ELISA, immunocytochemistry or immunohistochemistry, and immunofluorescence like flow cytometry assay, and FACS. The method of the invention may use any appropriate label used in immunoassays such as enzymes, biotin, fluorescent dyes/proteins or others.

In some embodiments, the method of detection or diagnosis of SARS-CoV-2 virus infection comprises the step of:
incubating the SARS-CoV-2 virus S protein antigen or fragment thereof comprising the receptor binding domain according to the present disclosure with the biological sample to form a mixture; and
detecting antigen-antibody complexes in the mixture.

The sample for anti-SARS-CoV-2 virus antibody detection is preferably body fluid from the individual, in particular serum.

The antigen is preferably labeled and the antigen-antibody complexes are detected by measuring the signal from the label by any appropriate means available for that purpose as disclosed above.

In some embodiments, the detecting step comprises the determination of the amount of bound antibody in the mixture, and optionally, comparing the amount of bound antibody in the mixture with at least one predetermined value.

The detection of the antibody in a sample from the individual using the methods of the invention is indicative of whether the individual is suffering from SARS-CoV-2 virus past or present infection.

Therefore, the above methods of the invention are useful for the diagnosis of SARS-CoV-2 virus infection in an individual, in particular the diagnosis of the disease caused by SARS-CoV-2 virus, ranging from febrile illness to severe acute respiratory syndrome.

In some embodiments, the above methods comprise the step of deducing therefrom whether the individual is suffering from SARS-CoV-2 virus infection i and in particular from a disease caused by SARS-CoV-2 virus.

In some embodiments in connection with this aspect of the invention, the above methods comprise a further step of administering an appropriate treatment to the individual depending on whether or not the individual is diagnosed with SARS-CoV-2 virus virus infection and in particular with a disease caused by SARS-CoV-2 virus.

Another aspect of the invention is a kit for the diagnosis or detection of SARS-CoV-2 virus, comprising at least one antigen for the detection of SARS-CoV-2 virus antibody, as defined above, preferably further including a detectable label.

Another aspect of the invention, relates to an immunogenic or vaccine pharmaceutical composition comprising, as active substance a SARS-CoV-2 virus S protein antigen or a fragment thereof comprising the receptor binding domain according to the present disclosure, in association with at least one pharmaceutically acceptable vehicle.

The pharmaceutical vehicles are those appropriate to the planned route of administration, which are well known in the art.

The pharmaceutical composition may further comprise a carrier and/or adjuvant. Non-limitative examples of carriers suitable for use in the composition of the invention include uni- or multi-lamellar liposomes, ISCOMS, virosomes, viral pseudo-particles, saponin micelles, saccharid (poly(lactide-co-glycolide)) or gold microspheres, and nanoparticules. Non-limitative examples of adjuvants suitable for use in the composition of the invention include: CpG oligodeoxynucleotide, polyI:C (polyinosinc-polycytidylic acid), oil emulsion, mineral substances, bacterial extracts, saponin, aluminium salts, monophosphoryl-lipid A and squalene.

The pharmaceutical composition comprises a therapeutically effective amount of the antigen sufficient to induce a protective immune response against SARS-CoV-2 virus infection in the individual to whom it is administered. The pharmaceutically effective dose depends upon the composition used, the route of administration, the physical characteristics of the specific human under consideration, concurrent medication, and other factors, that those skilled in the medical arts will recognize.

The invention provides also a SARS-CoV-2 virus S protein antigen or a fragment thereof comprising the receptor binding domain according to the present disclosure for use as a medicament.

The invention provides also a SARS-CoV-2 virus S protein antigen or a fragment thereof comprising the receptor binding domain according to the present disclosure or pharmaceutical composition according to the invention for use in the prevention or treatment of SARS-CoV-2 virus infection and associated disease.

The invention provides also a method for preventing or treating SARS-CoV-2 virus infection and associated disease, comprising: administering a therapeutically effective amount of the pharmaceutical composition according to the invention to the individual.

The pharmaceutical composition of the present invention is generally administered according to known procedures, at dosages and for periods of time effective to induce a beneficial effect in the individual. The administration may be by injection or mucosal administration, in particular respiratory such as intranasal administration.

The practice of the present invention will employ, unless otherwise indicated, conventional techniques which are within the skill of the art. Such techniques are explained fully in the literature.

The invention will now be exemplified with the following examples, which are not limitative, with reference to the attached drawings in which:

FIGURE LEGENDS

FIG. 1. Phylogenetic analysis of representative Betacoronaviruses and SARS-CoV-2 based on full length genome sequences.

The tree is midpoint rooted for ease of visualization, and high bootstrap values are indicated at key nodes.

Figure 2A:
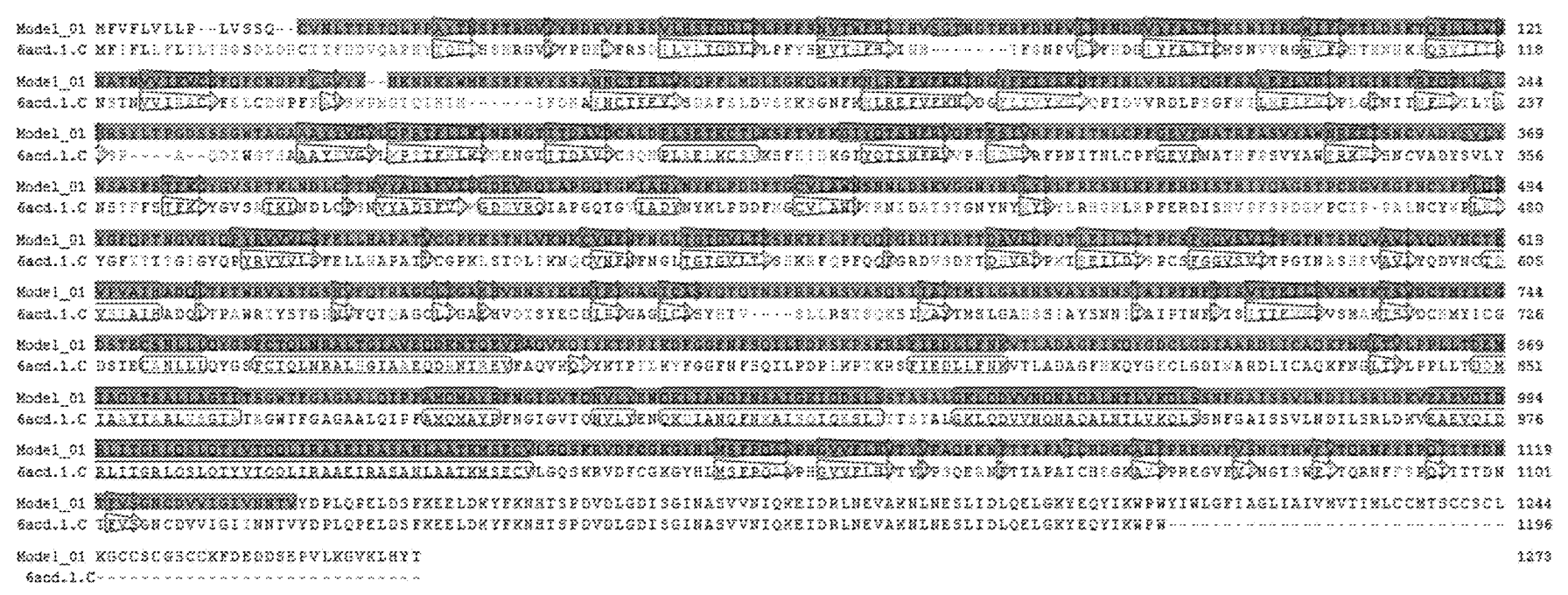
Figure 2B:

FIG. 2A-B. Homology modelling of the S protein of SARS-CoV-2 using the Swiss-Model tool (FIG. 2A) and showing the model based on the top-hit (PDB ID: 6ACD) (FIG. 2B).

In FIG. 2A, the alignment of Model_01(SEQ ID NO:2) and 6acd.1.C (SEQ ID NO:28) is shown. The putative RBD is highlighted with a black box in the alignment. The QMEAN score reflects the modelling quality. Similar results were obtained using Phyre2.

Figure 3:
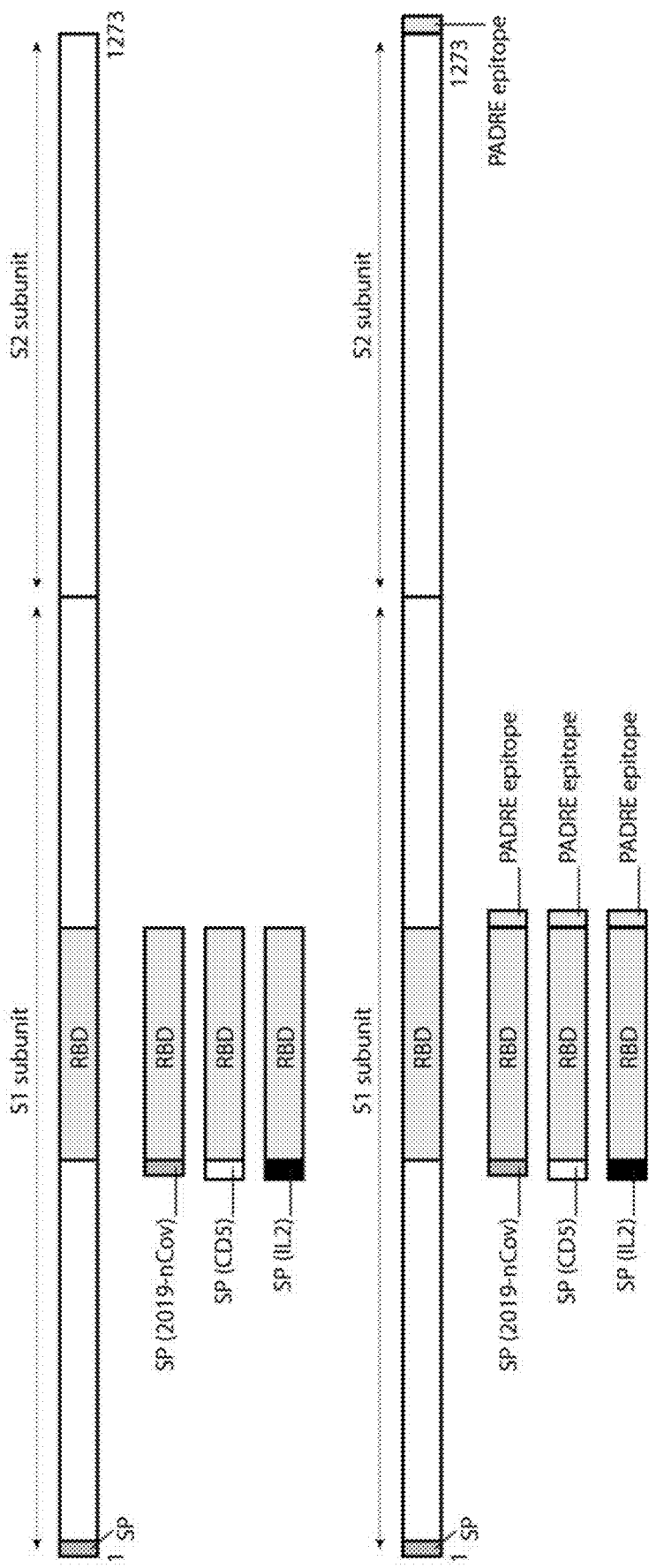
Figure 4C:
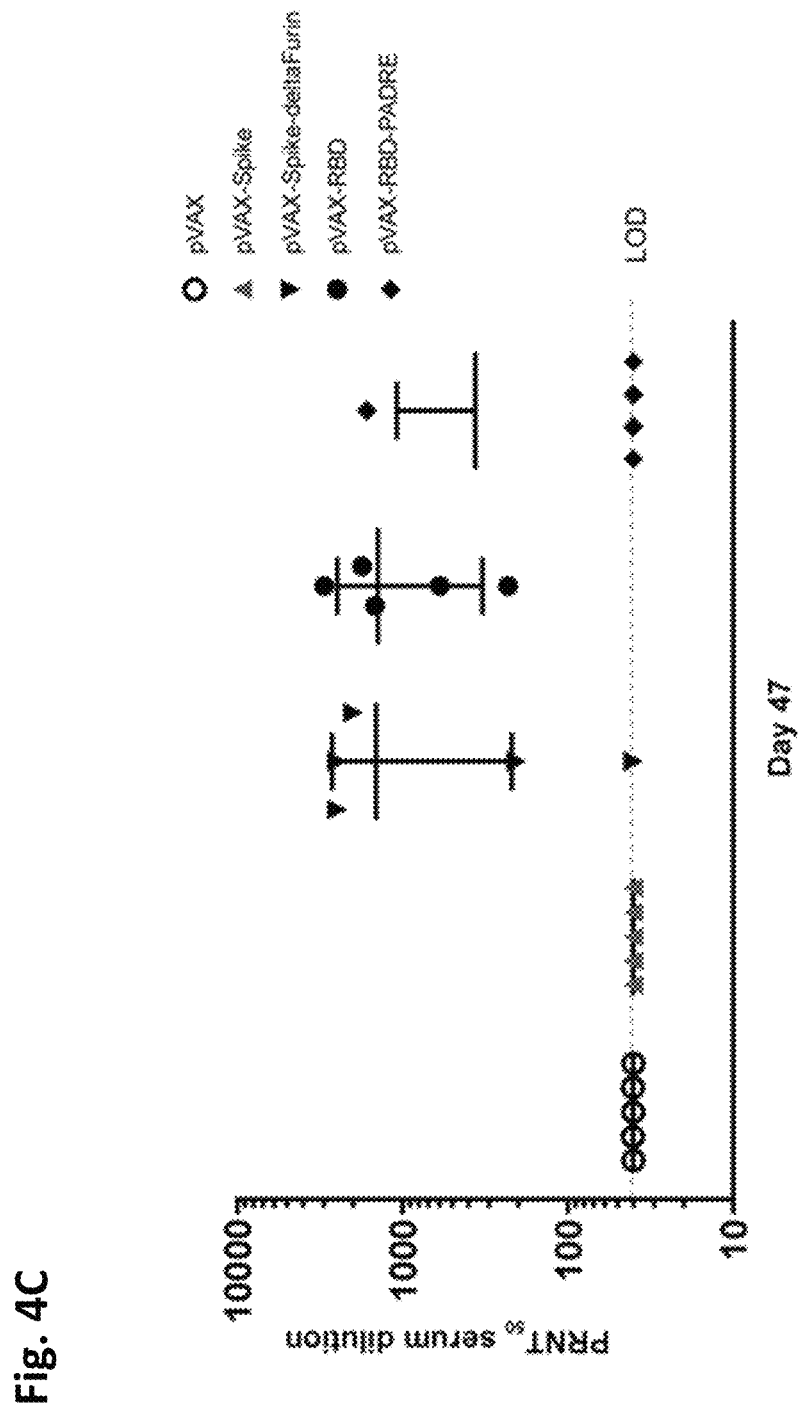

FIG. 3. Schematic representation of the selected antigens.
SP: Signal Peptide. RBD: Receptor Binding Domain.
FIG. 4A-C. SARS-CoV-2 neutralizing antibody titers in immunized BALB/c mice.

FIG. 4A Immunization scheme. Groups of 5 female Balb/c mice were immunized intra muscularly with 100 μg of pVAX vector containing the sequence of either the SARS-CoV-2 spike (pVAX-Spike), the spike with a mutated furin cleavage site (pVAX-Spike-deltaFurin), the receptor binding domain with the signal peptide of the spike (pVAX-RBD), the same RBD antigen with the PADRE sequence in 3' (pVAX-RBD-PADRE), or an empty vector (pVAX).

FIG. 4B Neutralizing antibody titers against SARS-CoV-2 at day 27 post immunization (prime), determined by plaque reduction neutralizing test ($PRNT_{50}$).

FIG. 4C Neutralizing antibody titers against SARS-CoV-2 at day 47 post immunization (prime-boost), determined by $PRNT_{50}$.

FIG. 5A-D. Immunogenicity and protective efficacy.

Groups of 5-8 female Balb/c mice were immunized intra muscularly (i.m.) with 100 pg of pVAX vector containing the sequence of the spike receptor binding domain with the signal peptide of the spike (pVAX-RBD) or an empty vector (pVAX). The immunization route was either i.m., intra nasal (i.n.) or a mix of i.m. for prime then i.n. for boosts, at 7-10 days intervals. At day 42 post initial immunization, mice were challenged i.n. with $1.10^5$ PFU of a mouse adapted SARS-CoV-2 strain. Viral load in the lungs was assessed at day 3 post infection.

FIG. 5A Immunization and challenge scheme.

FIG. 5B Neutralizing antibody titers against SARS-CoV-2 at day 42 post immunization (prime-boost-boost), determined by plaque reduction neutralizing test ($PRNT_{50}$).

Figure 5C:
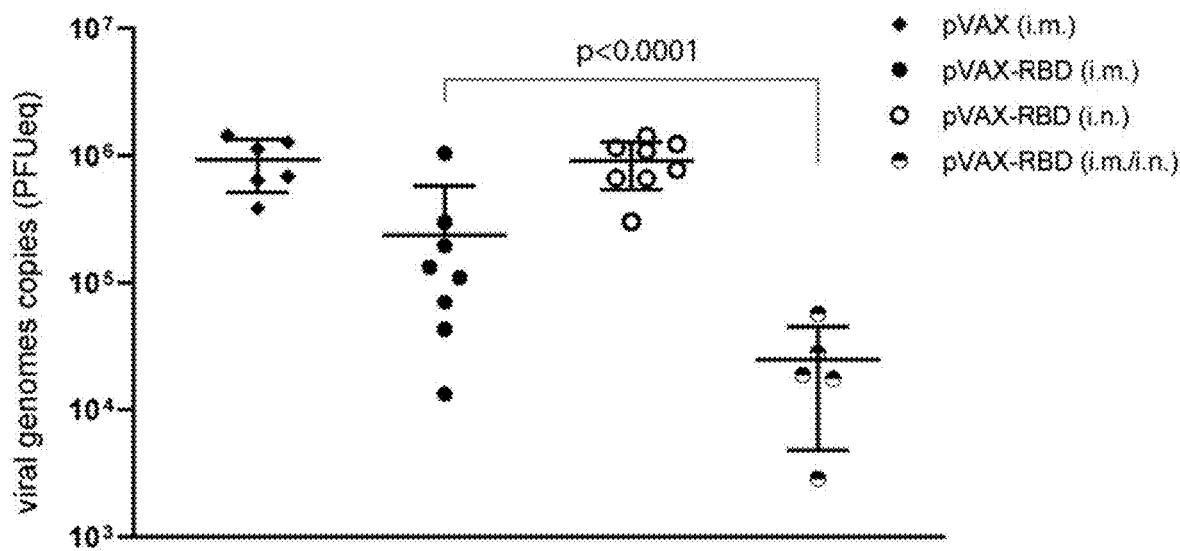

FIG. 5C Viral load (genomes copies as PFU equivalents) measured in the lungs at day 3 post challenge.

Figure 5D:
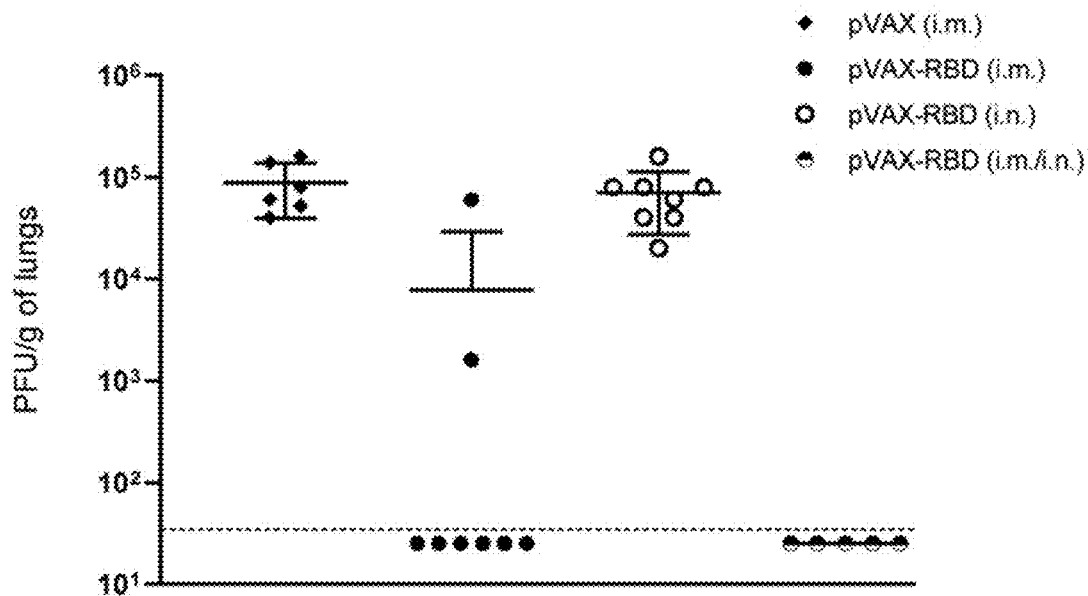

FIG. 5D Viral load (PFU per g of tissue) measure in the lungs at day 3 post challenge.

Figure 6:
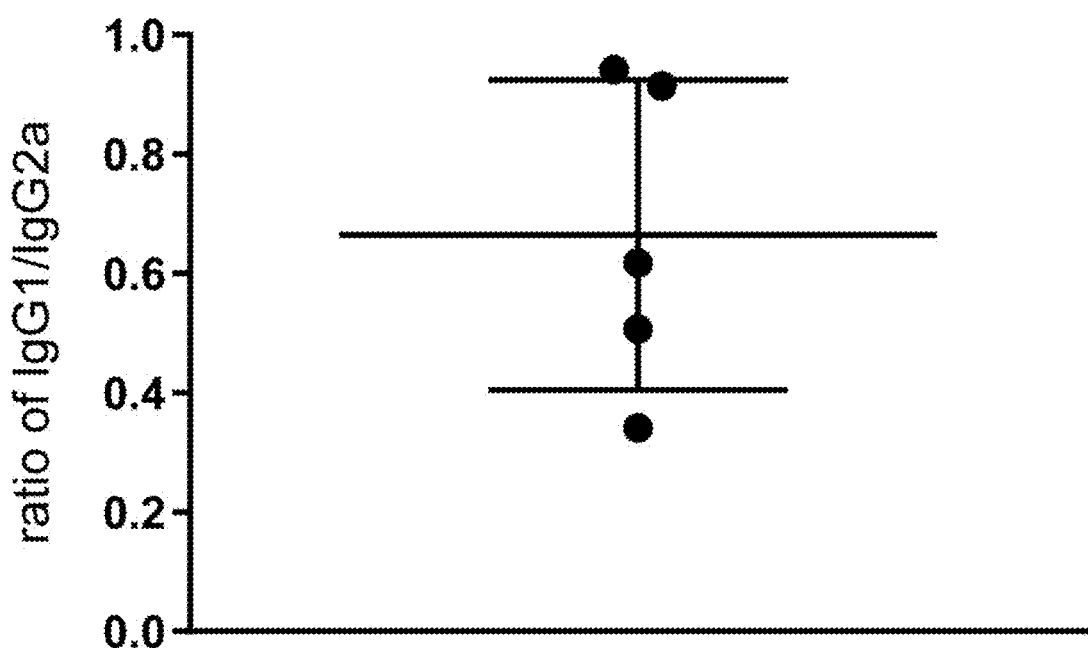

FIG. 6. ratio of IgG2a/IgG1 or Th1/Th2 responses.

The content of sera of Balb/c mice immunized with the receptor binding domain with the signal peptide of the spike (pVAX-RBD) using an i.m. prime-boost protocol were assessed by isotype specific ELISA against the SARS-CoV-2 RBD.

EXAMPLES

Material and Methods
1. Design of the Antigens

Phylogenetic analysis of publicly available SARS-CoV-2 (2019-nCov) full-length sequences (NCBI sequence data base) with representative sequences for the genus Betacoronavirus indicates that SARS-CoV-2 is part of a well-defined Sarbecovirus Glade that includes viruses sampled in bats (FIG. 1).

It is significantly different from the well-known human sarbecovirus SARS-Cov with only 79% identity at the nucleotide level over the full length of the genome. This value drops to 72.7% for S in nucleotides, and 76.2% in amino acids. However structural modelling using the Swiss-Model program (Waterhouse et al., Nucleic Acids Res., 2018 Jul. 2; 46(W1): W296-W303) or Phyre2 (Kelley et al., Nat Protoc. 2015 June; 10(6):845-58) and a representative sequence of the S protein of 2019-nCov (SARS-CoV-2) as query suggest a similar structural organization to the S protein of SARS-Cov, with core sections showing stronger sequence or structure conservation and modeling quality, and variation (with modelling uncertainty) mostly in the surface residues (FIG. 2).

In particular, a putative RBD of SARS-CoV-2 can be defined with, like for SARS-Cov (SARS-CoV-1), a core and an external subdomain. As it has been shown for other coronaviruses (Embemovirus MHV, HCov-229E or SARS-Cov), the RDB is highly reactive to anti-S neutralizing antibodies, and could comprise the key epitopes of the neutralizing response.

Based on the state of the art of betacoronaviruses biology, and in particular building on the structural similarity with SARS-Cov, the S protein is the most relevant antigen to include regardless of the delivery strategy. Two antigens have thus been designed (FIG. 3). One corresponds to the complete S protein, and the second, smaller (minimal) antigen, for ease of expression and production, correspond to the SARS-CoV-2 RBD of the S protein. To ensure secretion of the RBD antigen, 3 signal peptides (SP) have been selected.

Specifically, antigen 1 consists of 1273 amino acids or 3822 nucleotides, and the sequence has been codon-optimized for expression in *Homo sapiens*. Antigen 2 consists of 194 amino acids or 582 nucleotides, and the sequence has been codon-optimized for expression in *Homo sapiens*. Antigen 2 is combined with one of 3 SP (from the SARS-CoV-2) S protein; from the human CD5 or from the human IL-2). Other versions of Antigen 2 having SP variants according to the present disclosure are also engineered, one with a SP lacking SA in positions 20-21 of SEQ ID NO: 23; one with a SP lacking RLVA in positions 25 to 28 of SEQ ID NO: 19; and one with a SP lacking A in positions 20 of SEQ ID NO: 15.

These antigens can be delivered as nucleic acid immunogens, formulated with appropriate non-viral agent such as amphiphilic block copolymer or in a viral vector.

The antigens were also combined with a universal Pan HLA-DR Epitope termed PADRE. PADRE is a universal synthetic 13 amino acid peptide that activates CD4+ T cells. As PADRE binds with high affinity to 15 of the 16 most common human HLA-DR types, it provides potent CD4+ T cell responses and may overcome problems caused by polymorphism of HLA-DR molecules in human populations.

2. Plasmid Construction

The various cDNA sequences designed from 2019-nCov (SARS-CoV-2 or SARS2) sequences were codon-optimized for *Homo sapiens* expression, synthesized (Thermo-Fisher Scientific), and cloned into the pVAX-1 plasmid (Thermo-Fisher) under the control of a CMV promoter and containing a Kozak sequence. The cDNA sequences correspond to SEQ ID NO: 10, 12, 14, 16, 18, 20, 22, 24, 29, 31, 33, 35 in the attached sequence listing and encode r a protein antigen corresponding to the amino acid sequences SEQ ID NO: 11, 13, 15, 17, 19, 23, 25, 30, 32, 34 and 36, respectively in the attached sequence listing. pVAX-Spike comprises the cDNA of SEQ ID NO: 10 encoding a Spike of SEQ ID NO: 11. VAX-Spike-deltaFurin comprises the cDNA of SEQ ID NO: 29 encoding a Spike-deltaFurin of SEQ ID NO: 30. pVAX-RBD comprises the cDNA of SEQ ID NO: 14 encoding a RBD of SEQ ID NO: 15. pVAX-RBD-PADRE comprises the cDNA of SEQ ID NO: 16 encoding a RBD-PADRE of SEQ ID NO: 17. All pVAX derived plasmids were amplified in *Escherichia coli* and plasmid DNA was purified on EndoFree plasmid purification columns using the Nucleo-Bond Xtra Maxi EF Kit (Macherey Nagel). The constructs were verified by enzymatic digestion and by SANGER sequencing.

3. Formulation

The SARS-2 DNA vaccine is formulated by mixing equal volumes of ABC stock solution (Nanotaxi®, provided by In-Cell-Art; disclosed on page 13 to 17 of WO 2019/092002) in water and plasmid DNA solution at the desired concentration in 2× buffer solution, immediately prior to intramuscular injection. The mixing of ABC Nanotaxi® and plasmid DNA is a self-assembly process that results from hydrogen bonding, hydrophobic, and electrostatic interactions between ABC and DNA.

4. Antigen Expression/Western Blot Analysis 293 cells are transfected with plasmids expressing the antigens. After 24h, cell lysates and supernatant are harvested. Samples are fractionated by SDS-PAGE and transferred to cellulose membranes to be probed with anti-S antibodies or sera. A goat anti-mouse immunoglobulin G (IgG)-horseradish peroxidase (HRP) conjugate is used as secondary antibody. Peroxidase activity is visualized with an enhanced chemiluminescence detection kit (Thermo Fisher Scientific).

5. Animal Vaccination

Animal experiments are performed according to institutional, French and European ethical guidelines (Directive EEC 86/609/and Decree 87-848 of 19 Oct. 1987) subsequent to approval by the Institut Pasteur Safety, Animal Care and Use Committee, protocol agreement delivered by the local ethical committee and the Ministry of High Education and Research. Groups of at least 5 female Balb/c, transgenic K18-ACE2 (McCray et al., J. Virol., 2007, 81(2), 813-821), or other mice type, including C57BL/6C mice and interferon deficient mice such as IFNAR mice were housed under specific pathogen-free conditions in individually ventilated cages during the immunization period at the Institut Pasteur animal facilities. Mice were vaccinated with different constructs using a prime/boost regimen. Formulations was injected bilaterally into both tibial anterior muscles using an 8-mm, 30-gauge syringe (intra muscular (i.m.)), or intranasally (i.n.) at different time intervals. Mice were anesthetized by isoflurane before injection. A group of five unvaccinated mice, housed alongside the treated mice was used as controls. Sera were collected at various time points post-immunization to monitor the immune responses.

6. Cell Culture

Vero C10008 clone E6 (CRL-1586, ATCC) cells were maintained in Dulbecco's modified Eagle medium (DMEM) complemented with 10% heat-inactivated serum, 100 U/mL penicillin and 100 µg/mL streptomycin and were incubated at 37° C. and 5% CO2.

7. ELISA

Measurement of anti-S IgG antibody titers in serum of vaccinated mice is performed using either a commercial kit or an in house assay. Recombinant SARS-CoV-2 RBD were coated on 96-well MAXISORP plates. Coated plates were incubated overnight at 4° C. The plates were washed 3 times with PBS-0.05% Tween, then blocked 1 h at 37° C. with PBS-0.05% Tween-3% BSA. Serum samples from immunized mice were serially diluted and incubated for 1 h at 37° C. on the plates. HRP-conjugated isotype-specific (IgG1 or IgG2a) secondary antibodies were used to reveal the specific and relative amounts of IgG isotypes. Endpoint titers for each individual serum were calculated as the reciprocal of the last dilution giving twice the absorbance of the negative control sera.

8. Plaque Reduction Neutralization Test (PRNT)

For plaque reduction neutralization titer (PRNT) assays, Vero-E6 cells are seeded onto a 24-well plate and incubated at 37° C. for 12-24 h to 90% confluency. Two-fold serial dilutions of heat-inactivated serum samples are mixed with 50 PFU of SARS-CoV-2 for 1 h at 37 C, then added to cells for 2 h at 37° C. Virus/serum mix are then aspirated, and cells washed with PBS and overlaid with 1 mL of DMEM supplemented with with 5% fetal calf serum and and 1.5% carboxymethylcellulose. The plates were incubated for 3 days at 37° C. with 5% CO2. Viruses were then inactivated and cells fixed and stained with a 30% crystal violet solution containing 20% ethanol and 10% formaldehyde. Serum titer was measured as the dilution that reduced SARS-CoV-2 plaques by 50% ($PRNT_{50}$). This test was performed on several SARS-CoV-2 lineages as seen in the circulation in human. The SARS-CoV-2 lineages included in particular Glade L, Glade G (GISAID) and lineages B.1.1.7 (UK variant), B.1.351 (South Africa variant) and P.1 (Brazil variant).

9. SARS-CoV-2 Challenge

Animals were transferred to an isolator in BioSafety Level 3 animal facilities of Institut Pasteur. Mice were anesthetized by intra peritoneal (i.p.) injection of a mixture of Ketamine and Xylazine, transferred into a biosafety cabinet 3 where they were inoculated i.n. with either $1.10^5$ PFU of a mouse adapted strain of SARS-CoV-2 (MaCo3) for wild type Balb/C mice or $1.10^4$ PFU of a low passage clinical isolate (BetaCoV/France/GES-1973/2020) for the transgenic K18-ACE2 mice. The isolate BetaCoV/France/GES-1973/2020 was supplied by the National Reference Centre for Respiratory Viruses hosted at Institut Pasteur (Paris, France) and headed by Pr. Sylvie van der Werf.

Three days after challenge, mice were sacrificed and lung samples were collected aseptically, weighted, and mechanically homogenized in ice-cold PBS. The presence of SARS-CoV-2 in the lung was detected by titration on VeroE6 cells and by detecting viral RNA using a RT-qPCR (nCoV_IP4) targeting the RdRp gene, as described on the WHO website (https://www.who.int/docs/default-34 source/coronaviruse/real-time-rt-pcr-assays-for-the-detection-of-sars-cov-2-institut-35pasteur-paris.pdf?sfvrsn=3662fcb6_2).

As SARS-CoV-2 infection is lethal for K18-ACE2 mice, symptoms and weights were monitored for 14 days after challenge.

10. Lung Histopathology

Samples from the lung were fixed in formalin for at least 7 days and embedded in paraffin for histopathological examination.

Results

A prime-boost protocol with 4 weeks intervals between immunizations was first used to evaluate the immunogenicity of the different constructs. 100 µg of the pVAX plasmid containing either the complete SARS-CoV-2 spike, a spike modified at the furin site (spike delta furin), only the receptor binding domain (RBD) with the native signal peptide of the spike or the RBD with the PADRE sequence in 3' (RBD-PADRE) was injected intra-muscularly (i.m.) The plasmid DNA was mixed with an amphiphilic bloc copolymer for delivery.

The neutralizing potential of the sera was evaluated at day 27 (prior to the second immunization), and 20 days later (FIG. 4A). The neutralization plaque reduction neutralizing tests ($PRNT_{50}$) on the different constructs revealed that the smallest antigen (RBD) with the native signal peptide of the spike and without the PADRE sequence resulted in an early response already detectable 4 weeks after the prime (FIG. 4B), and which was more homogenously and consistently boosted by the second immunization in comparison to the other constructs (FIG. 4C).

Using the RBD construct, an accelerated protocol of a prime with two boosts, administered at 7-10 days intervals was next used (FIG. 5A). At day 42, the neutralizing potential of sera elicited using i.m, intra nasal (i.n.) and a mix of i.m. prime followed by boosts using the i.n. route was compared.

However, the challenge with a mouse adapted strain of SARS-CoV-2 inoculated i.n. revealed that the mixed protocol of i.m. and i.n. resulted in a lower viral load in the lungs of the animals in terms of viral RNA copies (FIG. 5C) and no infectious particles could be detected by titration. As expected from the PRNT results, mice immunized only by the i.n. route presented viral loads comparable to the mock vaccinated (empty vector pVAX) group (FIG. 5D). This shows that an accelerated immunization scheme over a short period of time can lead to strong neutralizing antibody titers.

As IgG isotype switching can serve as indirect indicators of Th1 and Th2 responses, the SARS-CoV-2 RBD-specific IgG1 and IgG2a isotype titers were determined in the sera of Balc/c mice immunized with the RBD antigen. Significantly higher IgG2a antibody titers than IgG1 were observed, reflecting a predominant Th1-type immune response (FIG. 6).

In conclusion, this study indicates that the RBD antigen is able to provide protection from a SARS-CoV-2 challenge of immunized animals, correlating with strong neutralizing antibody induction.

The invention claimed is:

1. An endotoxin-free preparation of a DNA plasmid construct encoding an mRNA encoding a SARS-CoV-2 virus Spike (S) protein antigen comprising a signal peptide comprising the amino acid sequence of SEQ ID NO:5, wherein said DNA construct comprises a sequence having at least 90% identity with the nucleotide sequence of SEQ ID NO:10, and wherein said DNA construct comprises a Kozak sequence comprising the sequence GCCACC in positions −6 to −1 relative to the ATG initiation codon of the S protein antigen.

2. The DNA construct of claim 1, wherein the S protein antigen comprises an amino acid sequence having at least 90% identity with SEQ ID NO: 4.

3. The DNA construct of claim 1, wherein the S protein antigen has at least 95% identity with the amino acid sequence from positions 19 to 1273 of SEQ ID NO:2.

4. The DNA construct of claim 1, wherein the S protein antigen has at least 97% identity with the amino acid sequence from positions 19 to 1273 of SEQ ID NO:2.

5. The DNA construct of claim 1, wherein the S protein antigen has at least 99% identity with the amino acid sequence from positions 19 to 1273 of SEQ ID NO:2.

6. The DNA construct of claim 1, wherein the S protein antigen has 100% identity with the amino acid sequence from positions 19 to 1273 of SEQ ID NO:2.

7. The DNA construct of claim 1, wherein said DNA construct comprises a sequence having the nucleotide sequence of SEQ ID NO: 10.

8. The DNA construct of claim 1, wherein said DNA construct comprises a sequence having at least 91% identity with the nucleotide sequence of SEQ ID NO:10.

9. The DNA construct of claim 1, wherein said DNA construct comprises a sequence having at least 93% identity with the nucleotide sequence of SEQ ID NO:10.

10. The DNA construct of claim 1, wherein said DNA construct comprises a sequence having at least 95% identity with the nucleotide sequence of SEQ ID NO:10.

11. The DNA construct of claim 1, wherein said DNA construct comprises a sequence having at least 97% identity with the nucleotide sequence of SEQ ID NO:10.

12. The DNA construct of claim 1, wherein said DNA construct comprises a sequence having at least 98% identity with the nucleotide sequence of SEQ ID NO:10.

13. The DNA construct of claim 1, wherein said DNA construct comprises a sequence having at least 99% identity with the nucleotide sequence of SEQ ID NO:10.

* * * * *